(12) United States Patent
Kruse et al.

(10) Patent No.: US 11,219,646 B2
(45) Date of Patent: Jan. 11, 2022

(54) CHIMERIC ANTIGEN RECEPTOR THERAPY WITH REDUCED CYTOTOXICITY FOR VIRAL DISEASE

(71) Applicant: Baylor College of Medicine, Houston, TX (US)

(72) Inventors: Robert Layne Kruse, Houston, TX (US); Karl-Dimiter Bissig, Houston, TX (US); Stephen M. G. Gottschalk, Houston, TX (US); Thomas C. T. Shum, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 6 days.

(21) Appl. No.: 16/334,712

(22) PCT Filed: Sep. 29, 2017

(86) PCT No.: PCT/US2017/054556
§ 371 (c)(1),
(2) Date: Mar. 19, 2019

(87) PCT Pub. No.: WO2018/064602
PCT Pub. Date: Apr. 5, 2018

(65) Prior Publication Data
US 2019/0307798 A1    Oct. 10, 2019

Related U.S. Application Data

(60) Provisional application No. 62/473,668, filed on Mar. 20, 2017, provisional application No. 62/402,731, filed on Sep. 30, 2016.

(51) Int. Cl.
| | |
|---|---|
| *A61K 35/17* | (2015.01) |
| *A61P 1/16* | (2006.01) |
| *A61P 31/20* | (2006.01) |
| *C07K 14/725* | (2006.01) |
| *C07K 14/705* | (2006.01) |
| *C07K 16/08* | (2006.01) |
| *C12N 15/11* | (2006.01) |

(52) U.S. Cl.
CPC ............... *A61K 35/17* (2013.01); *A61P 1/16* (2018.01); *A61P 31/20* (2018.01); *C07K 14/7051* (2013.01); *C07K 14/70521* (2013.01); *C07K 16/082* (2013.01); *C12N 15/11* (2013.01); *C07K 2317/21* (2013.01); *C07K 2317/53* (2013.01); *C07K 2317/622* (2013.01); *C07K 2319/03* (2013.01); *C07K 2319/33* (2013.01)

(58) Field of Classification Search
CPC ...... A61K 35/17; A61K 39/12; A61K 39/245; A61K 2039/5254; A61P 1/16; A61P 31/20; A61P 31/22; C07K 14/7051; C07K 14/70521; C07K 16/082; C07K 2317/53; C07K 2317/21; C07K 2319/03; C07K 2319/33; C07K 2317/622; C12N 15/11; C12N 7/00; C12N 7/04; C12N 15/86; C12N 2710/16043; C12N 2710/16443; C12N 2710/16434; C12N 2710/16452; C12N 2740/10043; C12N 2710/16034; C12N 2710/16062

See application file for complete search history.

(56) References Cited

U.S. PATENT DOCUMENTS

| | | | |
|---|---|---|---|
| 2015/0038684 A1 * | 2/2015 | Jensen .................... | A61K 35/17 |
| | | | 530/391.9 |
| 2015/0246948 A1 | 9/2015 | Yuan et al. | |
| 2016/0297884 A1 * | 10/2016 | Kuo ........................ | A61P 37/04 |
| 2019/0225673 A1 * | 7/2019 | Kruse .................... | A61P 31/20 |

FOREIGN PATENT DOCUMENTS

| | | | | |
|---|---|---|---|---|
| WO | WO-03028722 A1 * | 4/2003 | ............. | A61K 39/42 |
| WO | WO-2015036606 A1 * | 3/2015 | ................ | A61P 1/16 |
| WO | WO-2015075469 A1 * | 5/2015 | ........ | C07K 14/70589 |
| WO | WO-2016073755 A2 * | 5/2016 | ............. | A61K 35/17 |
| WO | WO-2016196388 A1 * | 12/2016 | ........... | C12N 15/111 |
| WO | WO-2016201300 A1 * | 12/2016 | ........ | A61K 47/6803 |

OTHER PUBLICATIONS

Pfeiffer A, Thalheimer FB, Hartmann S, Frank AM, Bender RR, Danisch S, Costa C, Wels WS, Modlich U, Stripecke R, et al. In vivo generation of human CD19-CAR T cells results in B-cell depletion and signs of cytokine release syndrome. EMBO Mol Med. 2018; 10:e9158.*

Smith TT, Stephan SB, Moffett HF, McKnight LE, Ji W, Reiman D, Bonagofski E, Wohlfahrt ME, Pillai SPS, Stephan MT. In situ programming of leukaemia-specific T cells using synthetic DNA nanocarriers. In Nat Nanotechnol. 2017;813-820.*

Bohne F, Chmielewski M, Ebert G, Wiegmann K, Kürschner T, Schulze A, Urban S, Krönke M, Abken H, Protzer U. T cells redirected against hepatitis B virus surface proteins eliminate infected hepatocytes. Gastroenterology. Jan. 2008;134(1):239-47. doi: 10.1053/j.gastro.2007.11.002. Epub Nov. 4, 2007.*

Bonne F, et al. [97] T Cells Redirected Against Hepatitis B Virus Surface Proteins Eliminate Infected Hepatocytes. J Hepatology. V. 46, Iss. Supp.1. S43, Apr. 2007.*

Neumann AU, Phillips S, Levine I, Ijaz S, Dahari H, Eren R, Dagan S, Naoumov NV. Novel mechanism of antibodies to hepatitis B virus in blocking viral particle release from cells. Hepatology. Sep. 2010;52(3):875-85. (Year: 2010).*

(Continued)

*Primary Examiner* — Rachel B Gill
(74) *Attorney, Agent, or Firm* — Perkins Coie LLP

(57) ABSTRACT

Embodiments of the disclosure encompass immunotherapy for Hepatitis B viral (HBV) infection in an individual in need thereof. The immunotherapy comprises one or more chimeric antigen receptors (CAR) that target a HBV antigen, including CAR molecules that utilize specific scFv antibodies. In certain cases, the CAR comprises one or more mutations to reduce binding to Fc receptors. In specific aspects, cells that express the CAR(s) have reduced cytotoxicity that is safer and/or beneficial to individuals that are immunocompromised.

35 Claims, 32 Drawing Sheets

Specification includes a Sequence Listing.

(56) References Cited

OTHER PUBLICATIONS

Kim N, Kim M, Yun S, Doh J, Greenberg PD, Kim TD, Choi I. MicroRNA-150 regulates the cytotoxicity of natural killers by targeting perforin-1. J Allergy Clin Immunol. Jul. 2014;134(1):195-203. Epub Mar. 31, 2014. (Year: 2014).*
Jonnalagadda M, Mardiros A, Urak R, Wang X, Hoffman LJ, Bernanke A, Chang WC, Bretzlaff W, et al. Chimeric antigen receptors with mutated IgG4 Fc spacer avoid fc receptor binding and improve T cell persistence and antitumor efficacy. Mol Ther. Apr. 2015; 23(4)757-68. Epub Nov. 4, 2014. (Year: 2015).*
Michailidis E, Kirby KA, Hachiya A, Yoo W, Hong SP, Kim SO, Folk WR, Sarafianos SG. Antiviral therapies: focus on hepatitis B reverse transcriptase. Int J Biochem Cell Biol. Jul. 2012;44(7):1060-71. Epub Apr. 16, 2012 (Year: 2012).*
Krebs et al., "T cells expressing a chimeric antigen receptor that binds hepatitis B virus envelope proteins control virus replication in mice" Gastroenterology, Aug. 2013, vol. 145, No. 2, pp. 456-465.
Tan et al., "A phage-displayed cyclic peptide that interacts tightly with the immunodominant region of hepatitis B surface antigen" J Clinical Virology, Sep. 2005, vol. 34, No. 1, pp. 35-41.
Rachel Eren, et al; "Preclinical Evaluation of Two Human Anti-Hepatitis B Virus (HBV) Monoclonal Antibodies in the HBV-Trimera Mouse Model and in HBV Chronic Carrier Chimpanzees"; Hepatology vol. 32, No. 3, 2000.
Felix Bohne, et al; "T Cells Redirected Against Hepatitis B Virus Surface Proteins Eliminate Infected Hepatocytes" Gastroenterology 2008; 134:239-247.
Sarene Koh, et al; Targeted Therapy of Hepatitis B Virus-Related Hepatocellular Carcinoma: Present and Future Diseases 2016, 4, 10, pp. 1-7.
Michael Hudecek, et al; "The Non-Signaling Extracellular Spacer Domain of Chimeric Antigen Receptors is Decisive for In Vivo Antitumor Activity"; Cancer Immunol Res., Feb. 2015; 3(2); 125-135.
Eithan Galun, et al; "Clinical Evaluation (Phase 1) of a Combination of Two Human Monoclonal Antibodies to HBV: Safety and Antiviral Properties"; Hepatology, vol. 35, No. 3; 2002; 673-679.
Karin Krebs, et al; "T Cells Expressing a Chimeric Antigen Receptor that Binds Hepatitis B Virus Envelope Proteins Control Virus Replication in Mice"; Gastroenterology 2013; 145:456-465.
Andeltje B. van Nunen, et al; "Efficacy and Safety of an Intravenous Monoclonal Anti-HBs n Chronic Hepatitis B Patients"; Liver 2001: 21: 207-212.
Ehud Ilan, et al; "TheHepatitis B Virus-Trimera Mouse: A Model for Human HBV Infection and Evaluation of Anti-HBV Therapeutic Agents"; Hepatology vol. 29, No. 2, 1999; 553-562.
Janine Kah, et al: "Lymphocytes Transiently Expressing Virus-Specific T Cell Receptors Reduce Hepatitis B Virus Infection"; The Journal of Clinical Investigation; Aug. 20, 2017; 1-12.
Haso et al. "Anti-CD22-chimeric antigen receptors targeting B-cell precursoracute lymphoblastic leukemia", Blood. Feb. 14, 2013; 121(7): 1165-1174.
Hudecek et al., "Receptor Affinity and Extracellular Domain Modifications Affect Tumor Recognition by ROR1-Specific Chimeric Antigen Receptor T Cells", Clin Cancer Res 2013;19:3153-3164. Published OnlineFirst Apr. 25, 2013, American Association for Cancer Research.
James et al., "Antigen Sensitivity of CD22-Specific Chimeric TCR Is Modulated by Target Epitope Distance from the Cell Membrane", J Immunol 2008; 180:7028-7038.
Krenciute et al. "Characterization and Functional Analysis of scFv-based Chimeric Antigen Receptors to Redirect T Cells to IL13R?2-positive Glioma", Molecular Therapy vol. 24 No. 2 Feb. 2016, pp. 354-363.

\* cited by examiner

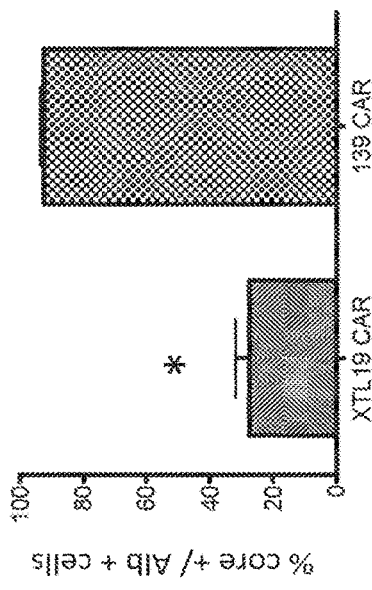
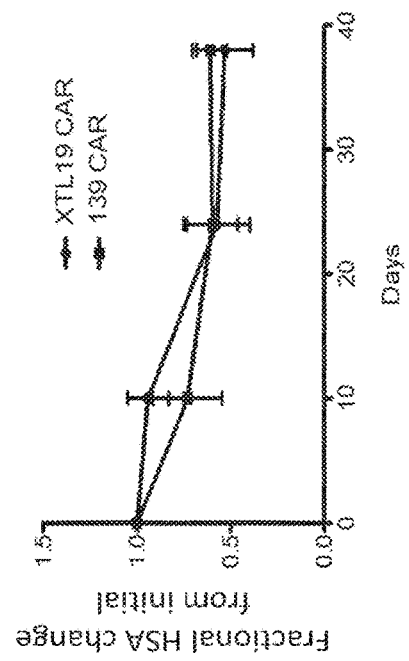
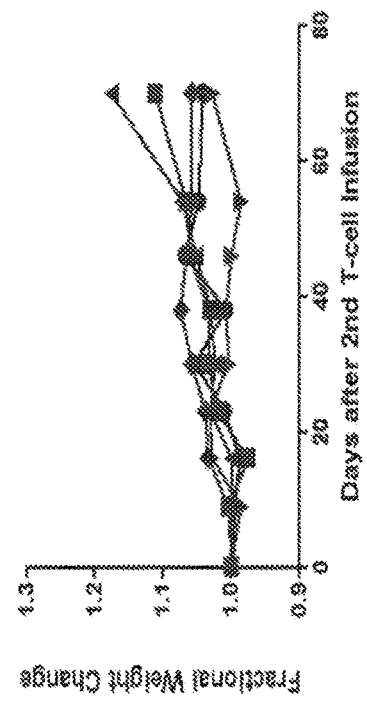
FIGS. 11C-11F

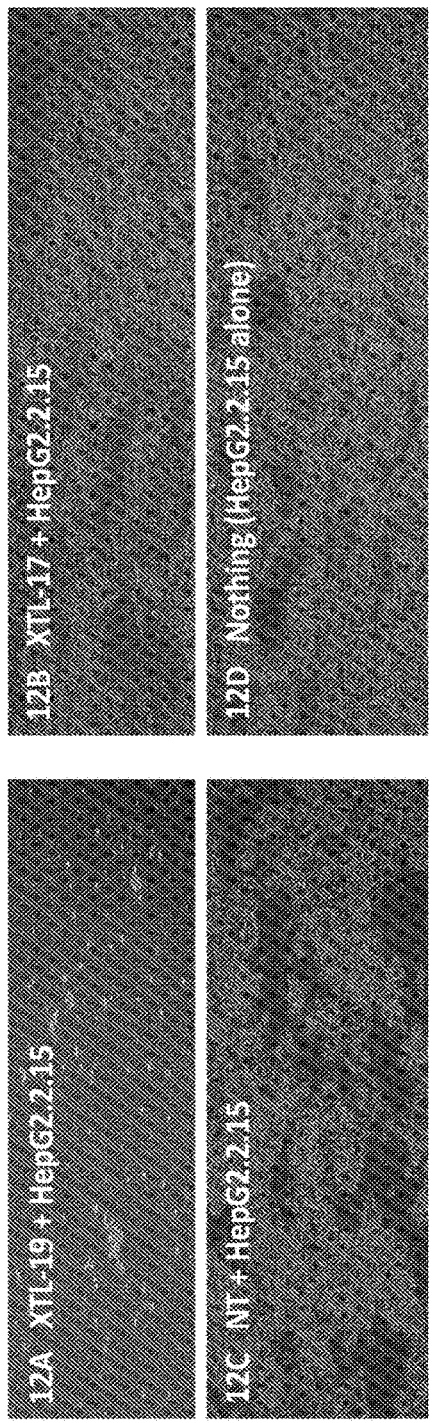
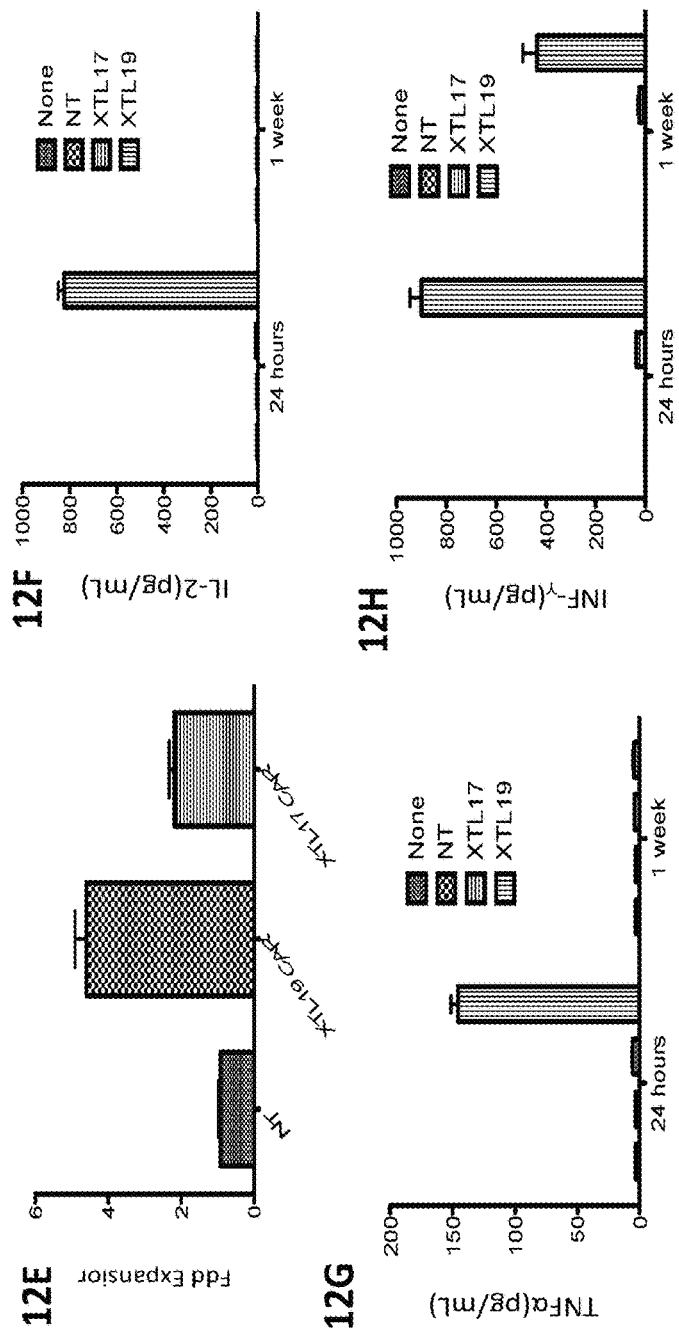
FIGS. 12A-12H

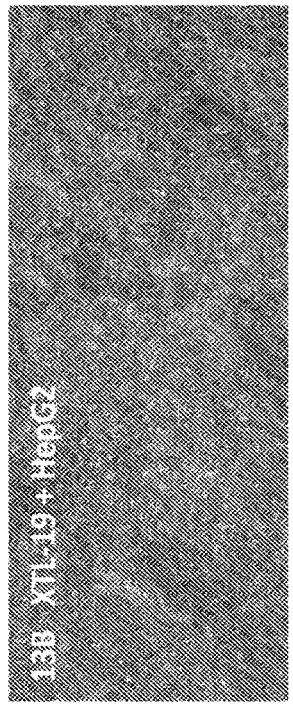
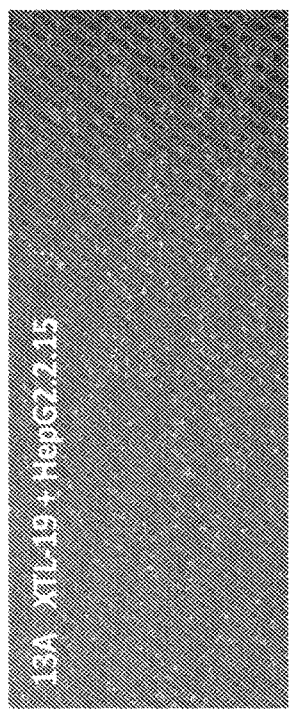
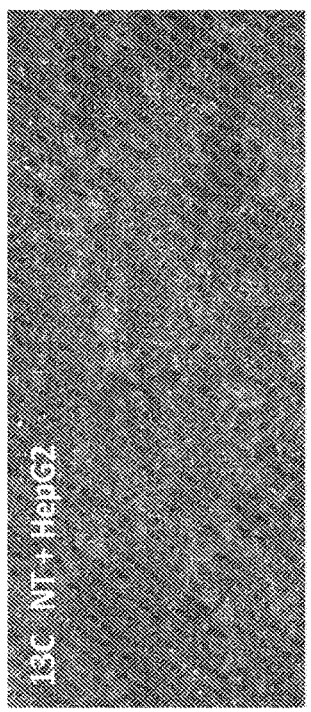
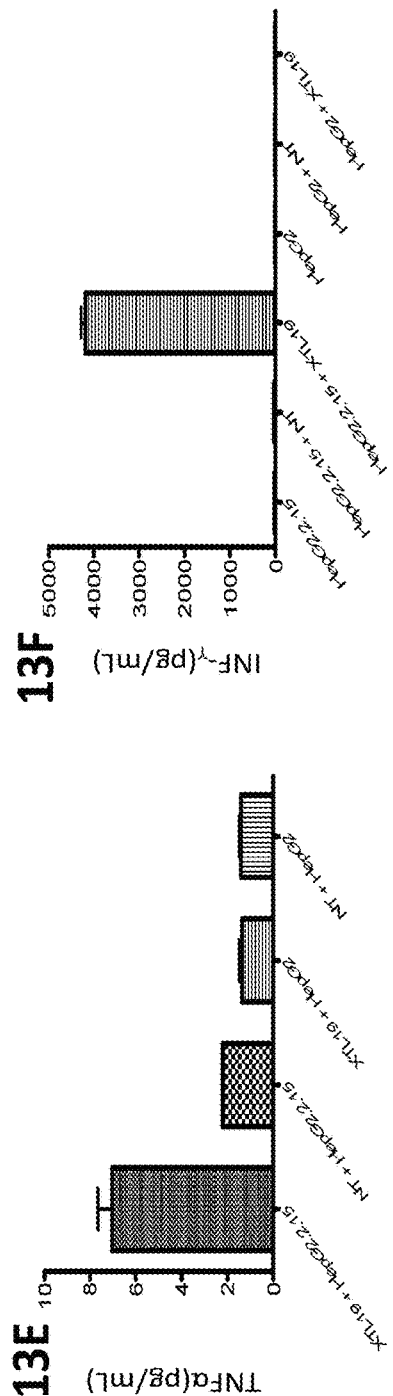
FIGS. 13A-13F

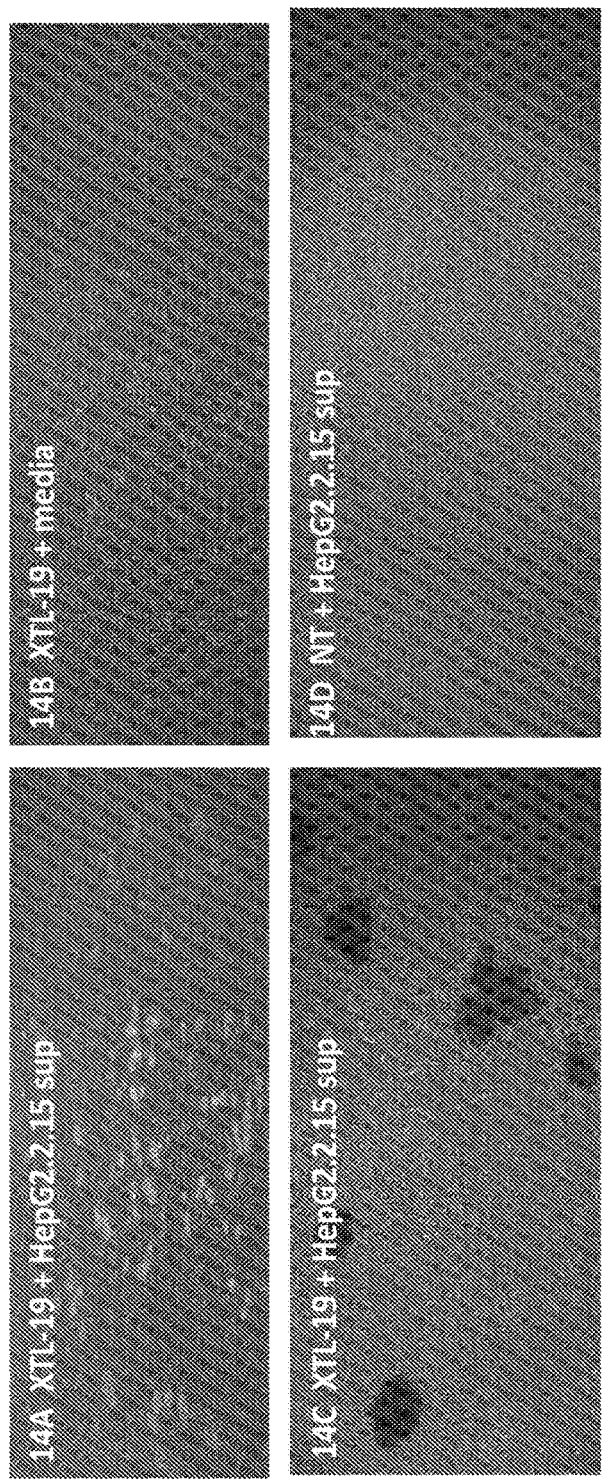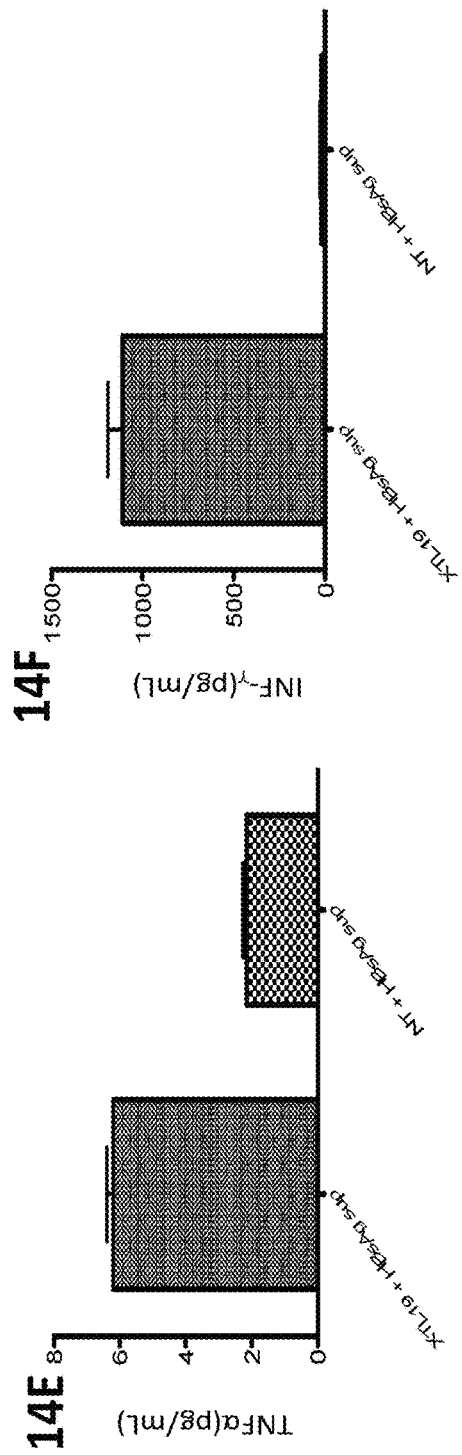
FIGS. 14A-14F

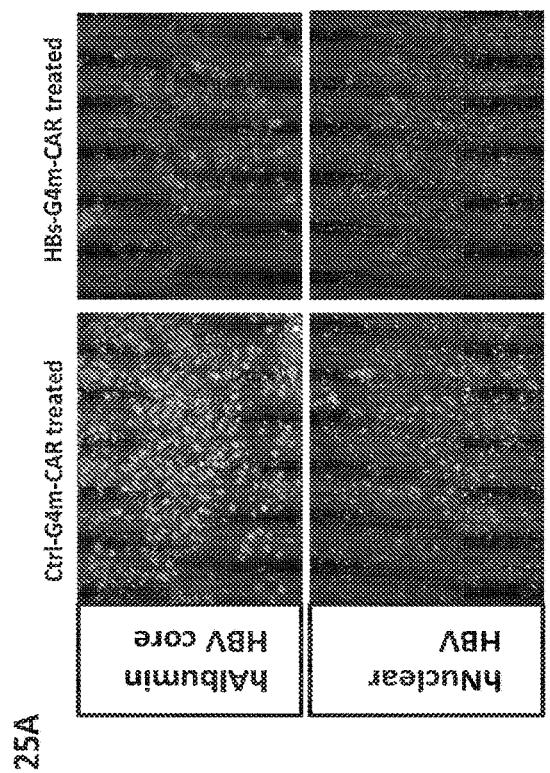
FIGS. 25A-25C

Ctrl-G4m-CAR treated | HBs-G4m-CAR treated

Human CD3 stain

CHIMERIC ANTIGEN RECEPTOR THERAPY WITH REDUCED CYTOTOXICITY FOR VIRAL DISEASE

This application is a national phase application under 35 U.S.C. § 371 that claims priority to International Application No. PCT/US2017/054556 filed Sep. 29, 2017, which claims priority to U.S. Provisional Patent Application Ser. No. 62/402,731, filed Sep. 30, 2016, and also to U.S. Provisional Patent Application Ser. No. 62/473,668, filed Mar. 20, 2017, all of which are incorporated herein by reference in their entirety.

TECHNICAL FIELD

Embodiments of the disclosure are directed at least to the fields of immunology, cell biology, molecular biology, and medicine.

BACKGROUND

Hepatitis B virus (HBV) therapies have currently remained limited to reverse transcriptase (RT) inhibitors and recombinant interferon alpha derivatives, the former of which only suppresses HBV DNA levels and the latter of which causes significant side effects in patients and only induces HBsAg seroconversion in a small percentage of patients. It is known during the HBV-specific immune response, that infiltrating T cells can rapidly purge the liver of virus within a matter of weeks. In chronic HBV patients, however, there is a deficiency in HBV-specific T cells in numbers and functionality.

The present disclosure satisfies a long-felt need in the art to provide effective treatments for HBV infection in mammals.

BRIEF SUMMARY

Embodiments of the disclosure include methods and compositions useful in treating one or more medical conditions with immunotherapy. In particular embodiments, the immunotherapy is directed to one or more particular antigens that may be expressed on a cell affected by the medical condition, such as a viral antigen on a host cell. In particular embodiments the medical condition affects the liver, and in specific embodiments the medical condition is viral infection that affects the liver. In particular cases the medical condition is Hepatitis B (HBV) infection of any serotype or genotype.

The present disclosure provides compositions and methods for the treatment of Hepatitis B virus (HBV) infection. In particular, the disclosure provides immune cells, for example T-lymphocytes (T-cells) or natural killer (NK) cells that express a chimeric antigen receptor (CAR) that targets one or more HBV antigens, and immunotherapy, methods of using, and methods of treatment incorporating, such CARS and such T cells.

In particular embodiments, the immunotherapy comprises immune cells engineered to target one or more certain HBV antigens expressed on affected cells of an individual in need of the immunotherapy, such as an individual seropositive for HBV, diagnosed with HBV, exposed to HBV, or at risk for HBV. Such targeting by the engineered immune cells may occur in any particular manner, but in specific embodiments the immune cells express a chimeric receptor capable of binding the one or more certain HBV antigens.

In particular embodiments, immune cells expressing chimeric antigen receptors (CARs) that target one or more HBV antigens are given to an individual in need thereof. The CARs may comprise one or more specific domains that target at least one Hepatitis B virus antigen. In certain embodiments, the specific domain(s) is an antibody, e.g., a single chain variable fragment (scFv) or a single chain antibody.

In particular embodiments, immune cells expressing the CAR molecules are modified such that they have reduced cytotoxicity compared to the level of cytotoxicity of unmodified cells. For example, the immune cells may be modified to have reduced levels of certain molecules (such as perforin, granzyme A, granzyme B, and so forth) that render the cells to have reduced cytotoxicity. Such modifications include genetic knockouts by nuclease or recombination strategies, siRNA-treated cells, shRNA-treated cells, and so forth. In other cases, particular CAR configurations inherently have a reduced level of cytotoxicity compared to other CAR configurations because of unique properties of the epitopes targeted and intrinsic characteristics of the CAR molecule. In some cases, the cells are modified to lack or have reduced levels of native T cell receptors. Cells encompassed by the disclosure may be irradiated prior to use in vivo.

In some cases, the CAR molecule is modified such that it has reduced or no binding affinity for a Fc receptor, including for any cell expressing a Fc receptor. Such modification(s) may be to an IgG Fc region of the CAR, in at least some examples.

In one embodiment, provided herein is a polynucleotide encoding a chimeric antigen receptor (CAR), wherein the CAR comprises one or more agents that target one or more Hepatitis B antigens (including one or more agents that target hepatitis B small surface antigen, hepatitis B middle surface antigen, hepatitis B large surface antigen, hepatitis B core antigen, or hepatitis B e antigen). In certain embodiments, the one or more agents is not C8 single chain variable fragment (scFv) or 5a19 scFv. In particular embodiments, the one or more agents that target a hepatitis B antigen is a single chain antibody, single chain variable fragment (scFv), peptide, camelid variable domain, shark IgNAR variable domain, single domain antibody, affimer or VHH antibody. In certain cases, the scFv is derived from monoclonal antibody 19.79.5 (Eren et al., 2000), 17.1.41 (Eren et al., 2000), OST 577 (Ehrlich et al., 1992), A5 (Bose et al., 2003), VHH-S4, VHH-S5, HzKR127 (Yang et al., 2007), KR359 (Maeng et al., 2000), 2B6 (Gao et al., 1997), 2D9 (Sankhyan et al., 2016), 2E7 (Sankhyan et al., 2016), 2G3 (Sankhyan et al., 2016), ADRI-2F3 (Cerino et al., 2015), E6F6 (Zhang et al., 2016), HB-C7A (Shin et al., 2007) or 1C9. In cases wherein the agent is a peptide, the peptide may be one targeting hepatitis B antigen that is Peptide A5, Peptide ETGAKPH, Peptide P7, Peptide pC, Peptide p2, Peptide p5, Peptide p18, Peptide 4B10, or Peptide SRLLYGW. In cases wherein the agent is a CAR, the CAR may comprise a linker region of at least two immunoglobulin domains. An immunoglobulin domain may comprise an immunoglobulin domain selected from the group consisting of extracellular regions of human proteins CD80, CD86, CD8, CD22, CD19, CD28, CD79, CD278, CD7, CD2, LILR, KIR, and CD4. The linker region may comprise an IgG Fc region, such as one from IgG1, IgG2, or IgG4. In certain cases, the IgG Fc region comprises one or more mutations (for example, in the glycosylation site of the IgG Fc domain or in the hinge domain). In certain embodiments, the CAR has reduced binding to an Fc Receptor as a result of these mutations. In certain embodiments, the IgG Fc region lacks the CH2 domain, has a CH2 domain from a different IgG than its natural IgG, or comprises an immunoglobulin domain from a different human protein (such as CD4, for example) such that the antibody can otherwise not bind to Fc receptors. In specific cases, the IgG Fc region is the IgG2 Fc region that comprises the IgG4 CH2 domain instead of the native IgG2 CH2 domain.

The CAR may comprise CD3 zeta chain and one or more co-stimulatory domains, such as those obtained or derived from a functional signaling domain derived from a protein selected from the group consisting of a MHC class I molecule, TNF receptor proteins, Immunoglobulin-like proteins, cytokine receptors, integrins, signaling lymphocytic activation molecules (SLAM proteins), activating NK cell receptors, EphA2, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In cases wherein the agent is a CAR, the CAR may comprise a linker region of a specific length, such as one between 100 and 500 amino acids in length. In some cases, the linker in the CAR is between an antigen binding domain and an transmembrane domain. The CAR may lack one or more signaling endodomains that trigger perforin secretion or granzyme secretion and/or the CAR may lack the zeta chain and/or the CD16 gamma chain. The CAR may also have mutations in these signaling domains that weaken subsequent cytotoxic signaling. Specific embodiments of a CAR may comprise the following: (1) one or more scFvs selected from the group consisting of 19.79.5, 17.1.41, OST577, A5, VHH-54, VHH-S5, HzKR127, KR359, 2B6, 2D9, 2E7, 2G3, ADRI-2F3, E6F6, 1C9, and HB-C7A; (2) a linker comprising at least one IgG Fc region from IgG1, IgG2, IgG3, or IgG4 that has a mutation that renders it unable to bind a Fc receptor (or have reduced binding compared to wild-type); (3) one or more endodomains.

In certain cases, the polynucleotide is further defined as an expression vector, including a viral vector or a non-viral vector. In specific cases, the expression vector expresses a shRNA, siRNA, or miRNA, such as one that targets perforin, granzyme A, granzyme B, granzyme C, granzyme D, Fas receptor, Fas ligand, TNF-alpha, beta-2 microglobulin, MHC class I molecules, MHC class II molecules, or TRAIL.

Cells that comprise polynucleotides that express the CAR are provided herein. In specific embodiments, the cells may be allogeneic or autologous with respect to an individual to whom the cell(s) are to be administered. In some cases, the cells are hematopoietic cells or progenitor cells or are immune cells (such as a T cell, NK cell, NK T cell, macrophage, or monocyte). The cells (including immune cells) may be a continuously growing and/or transformed cell line. In certain embodiments, the cells are present in a plurality of cells that lack CD45RA-positive cells. In specific embodiments, the cells are T cells that lack native T-cell receptors or have reduced expression of native T-cell receptors compared to a normal T cell. The cells may be genetically modified, for example, by a CRISPR/Cas9, TALE nuclease, meganuclease, homing endonuclease, or a zing finger nuclease system or by homologous recombination strategy to lack native T-cell receptors or have reduced level of native T-cell receptors. In specific embodiments, the cells are genetically modified to lack or have a reduced expression of one or more genes that encode one or more components of TCRalpha, TCRbeta, or both. In some specific cases, the cell has reduced expression or lacks detectable expression of one or more of perforin, one or more granzymes, Fas receptor, Fas ligand, TNF-alpha, beta macroglobulin, MHC class I molecules, MHC class II molecules, TRAIL, or a combination thereof. In certain cases, the cell has been irradiated. Cells may derive from a stem cell, which may be an induced pluripotent stem cell or an embryonic stem cell.

In particular embodiments, the disclosure provides cells that comprise an engineered receptor that is different from the main HBV-specific CAR receptor and that comprises one or more agents that target one or more Hepatitis B antigens. The engineered receptor may itself be a CAR, chimeric cytokine receptor, or αβT cell receptor and/or in other cases lack any signaling endodomains itself. The engineered receptor may bind to a different epitope of an HBV antigen not targeted by the receptor encoded by the polynucleotide, in order to create synergistic affinity. The engineered receptor and the receptor encoded by the polynucleotide may associate with each other via dimerization of hinge domains (ex: Fc-Fc homodimerization) in order to generate synergistic affinity and afford downstream signaling. In specific embodiments, the engineered receptor comprises one or more agents that target a Hepatitis B antigen. In certain cases for any receptor encompassed by the disclosure, a first agent is a peptide, affimer, single domain antibody, single chain variable fragment, or single chain antibody that binds one epitope of HBV antigen and the second agent is a single chain variable fragment, peptide, single domain antibody, or single chain antibody that binds a different antigen, thereby affording complementary binding potency with agents in tandem on the same receptor molecule.

Cells of the disclosure may comprise an inducible safety switch (means for killing the cells in the presence of a particular compound) for cell death, such as one wherein the inducible safety switch comprises part or all of Fas, caspase 8, or caspase 9. In other embodiments, the safety switch may be a second co-expressed epitope or protein on the cell surface that can be targeted by antibody drugs, including but not limited to CD20 or EGFR, for example.

The cells can be a primary cell isolate from an individual in need of therapy for Hepatitis B infection. In particular aspects, the cell is an immune cell capable of continuous growth while having anti-pathogen characteristics similar to a host immune cell line. Specifically, the cell may be from a NK-92, NKL, or NK-YS cell line of natural killer lineage. The cell may be from a TALL-104 or C-Cure 707 cell line of T cell lineage. In specific cases, the cell is an allogeneic NK-T cell with restricted T cell receptor to CD1d. The cell may comprise a knockout of MHC class II expression, such as a knockout of RFX and/or CIITA.

In certain cases, the cells comprise a second polynucleotide, other than the one that encodes the CAR that comprises one or more agents that target one or more Hepatitis B antigens, that is an expression vector that is different from the expression vector. The second polynucleotide may encode a shRNA, siRNA, or miRNA, such as one that targets perforin, granzyme A, granzyme B, granzyme C, granzyme D, Fas receptor, Fas ligand, TNF-alpha, TRAIL, MHC class I molecules, MCH class II molecules, and/or beta-2 microglobulin.

In one embodiment, there is a method of treating an individual for hepatitis B, comprising the step of delivering to the individual a therapeutically effective amount of cells encompassed by the disclosure and/or polynucleotides encompassed by the disclosure. In specific embodiments, the individual is immunocompromised. The individual may have cirrhotic HBV infection, allograft infection or chronic kidney disease, for example. In specific embodiments, the cells are T cells that lack native T-cell receptors or have reduced levels of native T-cell receptors compared to normal T cells. The individual may be lymphodepleted prior to administration of the cells. The cells may be irradiated prior to a delivering step.

In certain embodiments of the disclosure, the cells further comprise or express one or more agents that reduce cytotoxicity by modulating expression of a cytotoxicity-associated protein, such as perform, granzyme A, granzyme B, granzyme C, granzyme D, Fas receptor, Fas ligand, TRAIL, TNF-alpha, beta-2 microglobulin, MHC class II molecules, and/or MHC class I molecules or polynucleotides such as microRNAs, siRNAs, shRNAs or lncRNAs. In specific cases, the microRNA is human microRNA-150, human microRNA-27a*, microRNA-378, microRNA-30e, microRNA-139, microRNA-342, microRNA-378, or microRNA-23a. In some cases, the agent to reduce or eliminate expression comprises using CRISPR/Cas9, TALE nucleases, homing endonucleases, zing finger nucleases, or another site directed DNA nuclease or alternatively by homologous recombination strategies.

In particular embodiments of the method, the cells are allogeneic or autologous to the individual. The cells may comprise an engineered receptor other than the receptor encoded by the polynucleotide, such as a CAR, chimeric cytokine receptor, or αβT cell receptor. These two receptors may or may not dimerize together by their hinge domains to produce synergistic binding. In specific embodiments, the HBV-targeting CAR and the engineered receptor target different antigens or target different epitopes of the same antigen. The agent may be a single chain antibody is derived from a monoclonal antibody selected from the group consisting of 19.79.5, 17.1.41, OST577, A5, VHH-S4, VHH-S5, HzKR127, KR359, 2B6, 2D9, 2E7, 2G3, ADRI-2F3, E6F6, 1C9, and HB-C7A.

In certain embodiments, the liver is targeted by the HBV-targeting CAR and the cells are attenuated for toxicity. In the methods, the cell may comprise an inducible safety switch for cell death. The inducible safety switch may be a fusion protein with a first component binding a small molecule inducer and a second component that comprises part or all of Fas, caspase 8, or caspase 9. The inducible safety switch may comprise the expression of an extracellular domain that can be targeted with a monoclonal antibody to deplete therapeutic cells.

In specific aspects of the methods, the individual may be given multiple deliveries of the therapeutically effective amount of the cells, such as multiple deliveries separated by 1, 2, 3, 4, 5, 6, 7, 10, 14, 21, 28, 35, 42, 49, 56, or 63 days, or any range there between, for example. In some cases, the individual may be given an additional therapy for Hepatitis B infection. In specific cases, prior to, during, and/or after the delivery of the cells the individual is given a therapeutically effective amount of one or more antibodies that recognize a Hepatitis B antigen. Prior to, during, and/or after the delivery of the cells the individual may be given a therapeutically effective amount of one or more reverse transcriptase inhibitors (examples: lamivudine, adefovir dipivoxil, telbivudine, tenofovir alafenamide, tenofovir, and entecavir). The individual may be determined to have or remedied anti-HBsAg antibodies to have a baseline serum or plasma value of HBV surface antigen from 1,000 or 5,000 ng/mL or lower, that is otherwise predictive of higher therapeutic efficacy with HBsAg directed CAR T cells. Administration of Hepatitis B immunoglobulin may be useful in achieving HBsAg levels in this range. The individual may be administered an effective amount of one or more checkpoint modulating agents, such as anti-PD1, anti-PDL1, and/or anti-CTLA4 antibodies. The individual may be administered an effective amount of recombinant human interferon alfa-1, interferon alfa-2, interferon beta-1, interferon gamma-1, IL-2, IL-11, G-CSF, GM-CSF after the cell delivery. In specific cases, the cells are delivered by catheter via a portal vein or hepatic artery.

In one embodiment, there is a method of generating HBV-targeting CAR-positive cells in an individual, comprising the step of administering a vector that expresses an HBV-targeting CAR directly into the bone marrow of the individual (for example, to transduce patient hematopoietic stem cells or other immune effectors, where afterwards they or their descendent cells in multiple immune lineages (ex: T cell, NK cell, monocyte) express the chimeric antigen receptor molecule(s)) against HBV. The vector may be a viral vector (such as a lentiviral vector or retroviral vector) or non-viral vector.

Other and further objects, features, and advantages would be apparent and eventually more readily understood by reading the following specification and be reference to the accompanying drawings forming a part thereof, or any examples of the presently preferred embodiments of the invention given for the purpose of the disclosure.

BRIEF DESCRIPTION OF THE DRAWINGS

FIGS. 11A-11F. CAR-T cells mediate the decline of HBV levels over time in humanized mice. (11A) Serum viral levels of harvested mice before and after infusion. (11B) Livers were stained for human albumin (green) to identify hepatocytes, and human nuclear (green) to identify hepatocytes and T cells. HBV core (red) indicates HBV-infected cells contrasted with DAPI (blue). In control (139 CAR)-treated mice, almost every human hepatocyte co-stained with core. (11C) Infected and non-infected cell numbers were quantified across multiple sections, and ratio determined to approximate HBV-free cells. Note, human nuclear (11D) adds infiltrating CAR-T contribution, further lowering the ratio. (11E) Human serum albumin ELISA showed a similar decline in both groups, suggested a lack of direct cytotoxicity during this time. (11F) Weights of treated mice were measured, with a decline suggesting GVHD, but no weight loss was observed.

FIGS. 12A-12H show verification of the activation of CAR-T cells in vitro. (12A-12D) XTL19 CAR-T cells were co-cultured with HepG2.2.15 cells for one week. Cells were washed and remaining cells imaged. XTL19 exhibited no adherent HepG2.2.15 cells remaining, while XTL17, Non-transduced (NT) T cells, and media conditions still had abundant remaining HepG2.2.15 cells. (12E) T cells from the same co-culture were counted at the end of 7 days, and levels compared to the original 1 million cells per well dose. Greatest expansion was seen with XTL-19 CAR, with lesser expansion with XTL-17 CAR. (12F-12H) Supernatant was collected at 24 hours and at 1 week, and cytokine release assessed for IL-2, TNF-alpha, and IFN-γ. Only the XTL-19 CAR exhibited significant increases in cytokine release across all three biomarkers.

FIG. 13A-13F demonstrates CAR-T specificity for HBsAg. (13A-13D) XTL19 CAR-T cells or non-transduced T cells were co-cultured with HepG2.2.15 and HepG2 cells for one week. Cells were washed at one week and remaining cells imaged. XTL19 CAR exhibit no killing of HepG2 cells negative for HBsAg, indicating the effect is specific (13E) T cells from the same co-culture were counted at the end of 7 days, and levels compared to the original 1 million cells per well dose. XTL19 CAR-T cells exhibited significant expansion only when co-cultured with HepG2.2.15 cells and not with HBV-negative HepG2 cells. (13F) Similarly, supernatant collected at 24 hours across all conditions and assessed by ELISA for IFN-gamma secretion. Only XTL19 CAR demonstrated high levels of IFN-gamma secretion, indicative of CAR-T cell activation.

FIGS. 14A-14F show that testing in vitro of T cells expressing a modified hinge region replicated an original functionality in proliferation assays (the ability of the CAR to mediate signaling events to yield cell proliferation) upon comparing the hinge region and intact IgG1 and Fc receptor binding with a mutated Fc domain having those regions interrupted. (14A-14B) XTL-19 CAR-T were incubated with supernatant from HepG2.2.15 cells, containing authentic virions and HBsAg particles of different sizes, mimicking the natural infection, or with T cell media. Images taken at day 3 after setting up the incubation demonstrated pronounced activation of XTL-19 CART cells, as assessed by large clusters of cells. These same clusters were absent XTL-19 CAR-T cells were incubated with media alone. (14C-14D) Another experiment tested whether the HepG2.2.15 supernatant could activate T cells independent of CAR. XTL-19 CAR-T cells and non-transduced T cells were incubated with HepG2.2.15 supernatant, T cell activation and clustering was only observed in the CAR transduced T cells at Day 3. (14E) Expansion of XTL-19 CAR-T cells was assessed by comparing the T cell levels after the end of one week of incubation to the original 1 million per well dose. It was found that XTL-19 CAR-T cells exhibited significant higher expansion when non-transduced T cells incubated with HBsAg-containing media. (14F) Supernatant was also collected from this incubation at 24 hours and assessed by ELISA for INF-gamma secretion, indicative of T cell activation. Only XTL-19 CAR-T cells exhibited significant IFN-gamma secretion compared to non-transduced T cells, consistent with CAR-T activation function.

FIG. 25A-25C show that HBs-G4m-CAR T-cells decrease the percentage of HBV core-positive human hepatocytes. (25A) Immunofluorescence of liver sections for hAlbumin (green), HBV-Core (red), and DAPI (blue) or human nucleus (green), HBV-Core (red), and DAPI (blue), scale bar=50 (25B, 25C) HBV-Core+, hAlbumin+, and human nuclear+ hepatocytes were quantified. Ratio of HBV-Core+ to hAlbumin+, and HBV-Core+ to human nuclear+ cells is shown (***$p<0.0001$, n=4 fields). Unpaired, one-tailed t-tests determined significance.

DETAILED DESCRIPTION

Figure 1:
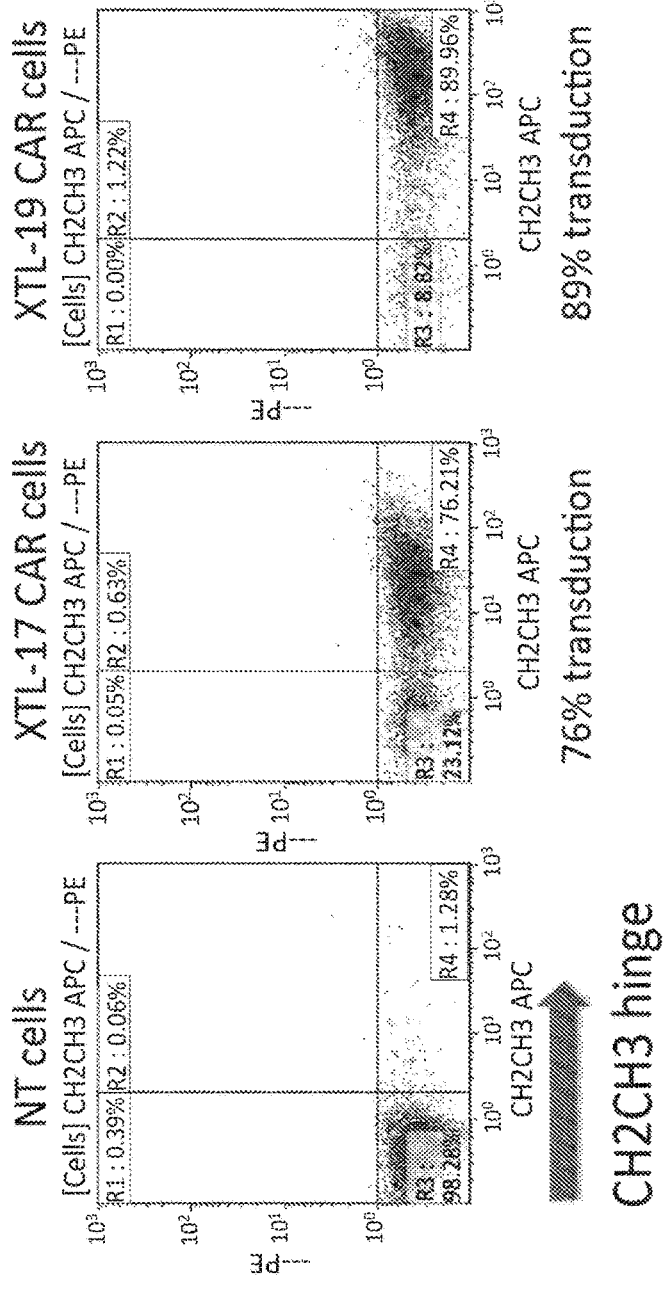
FIG. 1 is a representation of chimeric antigen receptor (CAR) T cell generation using XTL-19 or XTL-17 as particular scFvs for the CAR.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

I. General Embodiments

The present disclosure discloses a novel immunotherapy therapy platform that is useful in treating viral diseases in individuals. In a specific embodiment, the disclosure concerns therapy for hepatitis B virus (HBV). In particular aspects the HBV therapy comprises immunotherapy using one or more chimeric antigen receptors (CARs).

In specific embodiments, the CAR comprises one or more specific elements that facilitate its use for HBV therapy. Particular single chain antibodies described herein are suitable for function in the CAR, in specific embodiments. For example, in some cases an optimal length for the spacer domain of the CAR is utilized in order to target a certain viral surface antigen, as well as some embodiments that utilize mutations and designs in the molecule in order to make the CAR inert and avoid binding of off-target receptors, namely the Fc receptor. The disclosure further describes methods of targeting multiple viral antigens or epitopes in order to maximize the diversity of serotypes/genotypes covered by a single therapeutic product. In other embodiments, there are methods of tailoring the CAR therapy to a desired outcome, for example either a cytopathic T cell response, or a non-cytopathic cytokine driven T cell response. Regarding the latter, the inventors have designed strategies to suppress or knockout particular proteins (for example perform, granzymes, Fas, TNF-alpha) in cytotoxic function, thereby producing T cells that have reduced, or no, cytotoxic function. This is useful for reducing liver toxicity in HBV wherein target organ damage should be minimized, allowing it to be a safer therapy, lending to a more off-the-shelf strategy. The disclosure also concerns the combination of CAR therapy with safety systems in order to avoid tissue damage in certain clinical scenarios.

II. Examples of Chimeric Antigen Receptors (CARs)

Embodiments of the disclosure utilize one or more CAR compositions that target one or more HBV antigens. The CARs in both polynucleotide form and protein form are encompassed herein, including as they may reside in a cell in either form, for example. The CAR is chimeric, non-natural and engineered at least in part by the hand of man. The one or more components of the CAR facilitate targeting or binding of a cell that expresses it to the desired antigen-comprising tissue, cell, or soluble particle and/or molecule.

The CAR may be of any kind, including first generation (e.g., a CAR comprising a primary signaling domain such as CD3ζ), second generation (e.g., a CAR comprising a primary signaling domain such as CD3ζ, in combination with a co-stimulatory domain), or third generation (e.g., a CAR comprising a primary signaling domain such as CD3ζ, in combination with two or more co-stimulatory domains). In particular embodiments, the CAR comprises one or more agents that target one or more hepatitis B antigens. In some cases the CAR targets multiple antigens or epitopes because it comprises as the agent(s) two or more antigen binding domains on the same ectodomain. The one or more agents may be of any kind, but in specific aspects they are one of a single chain antibody, a single chain variable fragment (scFv), peptide, a single domain, camelid antibody, single domain or VHH antibody. Specific scFv molecules may or may not be utilized. In specific aspects, the CARs described herein do not comprise antibody C8 or 5a19, or a binding portion of C8 or 5a19, e.g., a C8 scFv or a 5a19 scFv. In certain specific aspects provided herein is any of the CARs described herein that comprises C8 scFv or 5a19 scFv. In particular embodiments, a CAR provided herein comprises an scFv from antibodies 19.79.5 19.79.5 scFv, 17.1.41 scFv, and/or OST577 scFv are employed in the CAR. In specific embodiments, human scFvs are utilized in CAR molecules, because multiple infusions would cause an immunogenic reaction to any mouse scFvs or any peptide strategies (as examples). In an alternative embodiment, non-human scFvs (ex: mouse, rat, rabbit) are utilized. In some cases, peptide strategies are utilized.

In specific embodiments, CARs using a hinge domain that is from derivatives of Fc receptors are utilized, and they may possess inherent dimeric binding of two single CAR molecules, as mediated through the disulfide bond formation in the flexible hinge domain of the Fc fragment, as well as hydrophobic interactions between the two CH3 domains. In particular embodiments, when two different CAR molecules both with Fc based domains are expressed in the same cell, they could either pair with each other, or with themselves in forming the steady state dimeric CAR molecule. This may be considered random pairing then, because it is uncontrollable, but in specific embodiments of the disclosure it is advantageous because engaging multiple epitopes on a viral HBsAg particle improves affinity, thereby helping to prevent viral escape. Thus, in some embodiments the CAR complex is a heterologously paired CAR formed from two molecules yielding a dimer, wherein two different CARs are co-expressed, allowing random pairing of their antibody linkers, creating enhanced affinity for target infected cell or pathogen.

In particular aspects, the CAR comprises a linker that operably links one or more ectodomains of the CAR (that comprise the one or more agents that target HBV) with one or more endodomains. The linker comprises one or more (including at least two) immunoglobulin domains, in certain cases, and in specific embodiments the linker comprises at least one IgG Fc region. The IgG Fc region may be of any kind, but in specific embodiments it is from IgG1, IgG2, IgG3, or IgG4. Although in some cases the IgG Fc region is wild type and thereby allows the CAR molecule to bind Fc receptors, in some cases it is desired to prevent binding to Fc receptors or at least to have reduced binding to Fc receptors compared to standard conditions. Such reduction in binding allows the cells expressing the CARs to have improved persistence in vivo. Thus, in certain embodiments, the IgG Fc region comprises one or more mutations that render it unable to bind a Fc receptor. Although the mutation may be of any kind and could be tested for Fc receptor binding using routine methods in the art, in specific embodiments the mutation is in the antibody hinge domain, CH2 domain, CH3 domain, or both, and/or in certain cases the mutation is in a glycosylation site of the IgG Fc region (for example, of $Asn^{297}$ in CH2 domain). In certain cases, a CH2 domain that is different from the CH2 domain of the IgG Fc region being used in the CAR is employed. For example, one may exchange a CH2 domain of IgG4 with the CH2 domain of IgG2. The CH2 domain may be removed, or the CH2 and CH3 domains are removed. In these cases, they may be replaced with immunoglobulin-like domains from other human proteins.

In certain embodiments, one or more endodomains, for example cytoplasmic signaling domains, such as those derived from the T cell receptor zeta-chain, are employed as at least part of the CAR in order to produce stimulatory signals for cell proliferation and effector function following engagement of the CAR with the target antigen. Certain co-stimulatory domains or combinations thereof may be employed. Examples would include, but are not limited to, endodomains from co-stimulatory molecules such as CD28, 4-1BB, OX40, CD27, DAP10, or ICOS. In particular embodiments, co-stimulatory molecules are employed to enhance the activation, proliferation, and cytotoxicity of T cells produced by the CAR after antigen engagement. In at least certain cases the CAR employs the CD3 zeta chain, whereas in other cases it lacks the CD3 zeta chain and/or the CD16 gamma chain.

In particular aspects the linker of the CAR is of a certain length, for example, to allow sufficient access to the antigen to which the CAR is targeting. An appropriate length may be determined by one of skill in the art using methods as described herein, for example. In particular embodiments the linker is at least a certain number of amino acids in length and/or in is no more than a certain number of amino acids in length. In particular aspects the linker is greater than 100 amino acids and/or less than 500 amino acids in length. In some cases, the linker is at least or no more than 50, 75, 100, 125, 150, 175, 200, 225, 250, 275, 300, 325, 350, 375, 400, 425, 450, 475, or 500 amino acids in length.

In particular embodiments, the CAR comprises one or more of a linker region that is between 100-500 amino acids in length, a CD8 alpha stalk, an IgG Fc region, and/or comprised one or more immunoglobulin domains. In specific aspects, the IgG Fc region comprises a) one or more mutations to disrupt FcR binding, b) a deletion of the CH2 domain, and/or c) replacement of the CH2 domain, for example with another immunoglobulin domain from a different human protein (such as an immunoglobulin from an alternative human protein selected from human CD4 domains D2 through D4). Mutations that disrupt FcR binding may be located in the hinge region and/or glycosylation site of IgG Fc domain (including IgG1 Fc domain, IgG2 Fc domain, or IgG4 Fc domain, for example.

Also provided herein are polynucleotides that encode the HBsAg-specific CARs disclosed herein. In certain embodiments, the polynucleotide is comprised within an expression vector. The expression vector may be either a viral vector or non-viral vector (such as a plasmid). Viral vectors that can be used to express the CARs provided herein include adenoviral vectors, lentiviral vectors, retroviral vectors, and adeno-associated viral vectors, for example. The expression vector may or may not also comprise a region that encodes a gene product other than the CAR, such as another type of engineered receptor (another CAR, a chimeric cytokine receptor, membrane-bound antibody, or an αβ T cell receptor, for example) and/or one or more siRNAs or shRNAs or miRNAs to knock down, or knock out, expression of one or more genes in an immune cell expressing the CAR, and so forth. In some cases the siRNA or shRNA or miRNA targets a gene associated with the endogenous T cell receptor (including component genes of TCRalpha, TCRbeta, or both, such as to prevent graft versus host disease in allogeneic T cell products. Specific examples of siRNA or shRNA targets include perforin, granzyme A, granzyme B, granzyme C, granzyme D, Fas receptor, Fas ligand, TRAIL, MHC class I molecules, MHC Class II molecules, and/or beta-2 microglobulin. When the expression vector expresses both the CAR and a second region that encodes a gene product other than the CAR, the regulation of the two coding regions may or may not occur through the same regulatory region. One or both of the encoded products may or may not be labeled.

In a particular embodiment, the components of the CAR in the polynucleotide that encodes it are in a particular order so that the expressed CAR protein has the corresponding domains in a particular order. For example, in particular embodiments the transmembrane domain is configured between the ectodomain (for example, the scFv domain) and the endodomain, and all components are operably linked. In specific embodiments, the order of the domains in the encoded CAR protein is N-terminus-antibody-transmembrane domain-endodomain-C terminus, although in certain cases the order of the domains in the encoded CAR protein is N-terminal-endodomain-transmembrane domain-antibody-C terminus. Of course, other domains may be inserted within this configuration, with care being taken to place it on the appropriate side of the transmembrane domain to be located inside the cell or on the surface of the cell. Those domains that need to be intracellular need to be on the flank of the transmembrane domain in the protein that the endodomain is located, for example. Those domains that need to be extracellular need to be on the flank of the transmembrane domain in the protein that the antibody is located.

In certain embodiments, a CAR that directs an immune cell or stem cell to one or more HBV antigens comprises (1) an extracellular antigen-binding domain that binds to the HBV antigen, and (2) an intracellular domain that comprises a primary signaling moiety, e.g., a CD3ζ chain, that provides a primary T cell activation signal, and optionally one or more costimulatory moieties, e.g., a CD28 polypeptide and/or a 4-1BB (CD137) polypeptide. In particular cases, the CAR is specific for one or more HBV antigens, and in certain embodiments, the present disclosure provides chimeric immune cells (such as T cells) specific for the HBV antigen by joining an extracellular antigen-binding domain derived from a HBV antigen-specific antibody to cytoplasmic signaling domain(s) derived from the T-cell receptor ζ-chain, with the endodomain(s) of certain costimulatory molecules (CD28 and OX40, for examples). This CAR is expressed in human cells and the targeting of HBV-positive cells or tissue is encompassed in the disclosure. In particular embodiments, a CAR specific for one or more HBV antigens refers to a CAR having at least one single chain antibody that recognizes an HBV antigen. In specific cases a CAR comprises 1) an ectodomain with affinity toward a HBV protein, 2) a linker region, and 3) an endodomain with one or more activation motifs (and may comprise multiple different endodomains in various combinations). In specific embodiments, the ectodomain comprises a peptide, a single chain antibody, a single chain variable fragment, or a camelid antibody. In some embodiments, there may be two or more ectodomains that target HBV antigens within a single CAR molecule. In certain aspects, the endodomain comprises one or more of a zeta signaling domain, a CD16 gamma chain, a CD28 signaling region, a 4-1BB signaling region, and/or an OX40 endodomain, although in other cases some of these elements are lacking. See, e.g., Yagyu et al., *Mol. Ther.* 23(9):1475-1485 (2015).

In particular embodiments, an expression vector comprises an inducible safety switch for cell death, such as a protein (e.g., Fas, caspase 8, or caspase 9, or variants thereof for example) that is dimerizable, and activated upon dimerization, using, e.g., a small molecule compound such as FK506 (tacrolimus) or a variant thereof, a divalent receptor, an antibody, or the like. In particular embodiments, an expression vector comprises an inducible safety switch encompassing a fusion protein with one component binding a small molecule inducer and the second component comprises part or all of Fas, caspase 8, or caspase 9 in order to trigger apoptosis.

Peptides can also be used as the agent targeting a CAR disclosed herein to HBV, e.g., to HBsAg. In certain embodiments, the CARs provided herein comprise one of the peptides listed below as an HBV targeting agent:

```
Peptide A5 (targets PreS1, Reference PMID:
24966187):
SGSGLKKKWST                 (SEQ ID NO: 1)

Peptide ETGAKPH (targets HBsAg, Reference PMID:
16087122):
CETGAKPHC                   (SEQ ID NO: 2)

Peptide P7 (targets PreS1, Reference PMID:
21856287):
KHMHWHPPALNT                (SEQ ID NO: 3)

Peptide pC (targets PreS1, Reference PMID:
17192308):
SGSGWTNWWST                 (SEQ ID NO: 4)

Peptide p2 (targets PreS1, Reference PMID:
17192308):
NNWWYWWDTLVN                (SEQ ID NO: 5)

Peptide p5 (targets PreS1, Reference PMID:
17192308):
GLWRFWFGDFLT                (SEQ ID NO: 6)

Peptide p18 (targets PreS1, Reference PMID:
17192308):
WTDMFTAWWSTP                (SEQ ID NO: 7)

Peptide 4B10 (targets PreS1, Reference PMID:
27384014):
LRNIRLRNIRLRNIRLRNIR        (SEQ ID NO: 8)
```

```
-continued
Peptide SRLLYGW (targets PreS1, Reference PMID:
15996026):
CSRLLYGWC                   (SEQ ID NO: 9)
```

In some embodiments, two or more of such peptides will form a bispecific CAR, wherein a peptide and scFv against different HBsAg epitopes or proteins are joined in tandem to result in bivalent binding. Particular embodiments utilize a PreS1 binding peptide in conjunction with an antibody that binds to the small HBsAg protein.

Specific CAR molecules may be as follows: a) a chimeric antigen receptor having the sequence to target Hepatitis B virus: 19.79.5 scFv-G4m-CD28-CD3 zeta; and b) a chimeric antigen receptor lacking cytolytic effects having the sequence: 19.79.5 scFv-G4m-CD28-41BB, where G4m refers to an example of a mutated version of the IgG4 Fc region lacking Fc receptor binding. However, other CAR molecules having different scFv antibodies, different linkers, and different endodomains and combinations thereof are contemplated herein.

Sequences of exemplary molecules used in particular embodiments are as follows (where 19.79.5 scFv is referred to as XTL19):

```
XTL19 - IgG4m - CD28 - Zeta (thus, a CAR
comprising the XTL19 scFv, a mutated IgG4 Fc
region, a CD28 costimulatory domain, and a
zeta chain)
                                (SEQ ID NO: 10)
MDWIWRILFLVGAATGAHSQVQLVESGGGVVQPGGSLRLSCAPSGFVFRS

YGMHWVRQTPGKGLEWVSLIWHDGSNRFYADSVKGRFTISRDNSKNTLYL

QMNSLRAEDTAMYFCARERLIAAPAAFDLWGQGTLVTVSSGGGGSGGGGS

GGGGSSYVLTQPPSVSVAPGKTARISCGGNNIGTKNVHWYQQKPGQAPVL

VVYADSDRPSGIPERFSGSNSGNTATLTISRVEVGDEADYYCQVWDSVSY

HVVFGGGTTLTVLGSGGGGSESKYGPPCPSCPAPPVAGPSVFLFPPKPKD

TLMISRTPEVTCVVVDVSQEDPEVQFNWYVDGVEVHNAKTKPREEQFQST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSPGKKD

PKFWVLVVVGGVLACYSLLVTVAFIIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

XTL19 - IgG4m - CD28 - OX40 (thus, a CAR
comprising the XTL19 scFv, a mutated IgG4 Fc
region, a CD28 costimulatory domain, and an
OX40 costimulatory domain)
                                (SEQ ID NO: 11)
MDWIWRILFLVGAATGAHSQVQLVESGGGVVQPGGSLRLSCAPSGFVFRS

YGMHWVRQTPGKGLEWVSLIWHDGSNRFYADSVKGRFTISRDNSKNTLYL

QMNSLRAEDTAMYFCARERLIAAPAAFDLWGQGTLVTVSSGGGGSGGGGS

GGGGSSYVLTQPPSVSVAPGKTARISCGGNNIGTKNVHWYQQKPGQAPVL

VVYADSDRPSGIPERFSGSNSGNTATLTISRVEVGDEADYYCQVWDSVSY

HVVFGGGTTLTVLGSGGGGSESKYGPPCPSCPAPPVAGPSVFLFPPKPKD

TLMISRTPEVTCVVVDVSQEDPEVQFNWYVDGVEVHNAKTKPREEQFQST

YRVVSVLTVLHQDWLNGKEYKCKVSNKGLPSSIEKTISKAKGQPREPQVY
```

-continued
TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSPGKKD

PKFWVLVVVGGVLACYSLLVTVAFIIFWVRSKRSRLLHSDYMNMTPRRPG

PTRKHYQPYAPPRDFAAYRSRDQRLPPDAH KPPGGGSFRTPIQEEQADA

HSTLAKI

XTL17 - IgG4m - CD28 - Zeta (thus, a CAR
comprising the XTL17 scFv (17.1.41 scFv), a
mutated IgG4 hinge, a CD28 costimulatory
domain, and a zeta chain)
(SEQ ID NO: 12)
MDWIWRILFLVGAATGAHSQVQLVESGGGVVRPGRSLRLSCAASGFAFSD

YSINWVRQAPGKGLEWVAIISYDGRITYYRDSVKGRFTISRDDSKNTLYL

QMNSLRTEDTAVYYCARQYYDFWSGSSVGRNYDGMDVWGLGTTVTVSSGG

GGSGGGGSGGGGSDIVMTQSPLSLSVTPGEPASISCRSSQSLLHRSGNNY

LDWYLQKPGHSPQLLIYVGSNRASGVPDRFSGSGSGTEYTLRISTVEAED

VGVYYCMQALQTPRTFGQGTKLEIKRSGGGGSESKYGPPCPSCPAPPVAG

PSVFLFPPKPKDTLMISRTPEVTCVVVDVSQEDPEVQFNWYVDGVEVHNA

KTKPREEQFQSTYRVVSVLTVL HQDWLNGKEYKCKVSNKGLPSSIEKTI

SKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHY

TQKSLSLSPGKKDPKFWVLVVVGGVLACYSLLVTVAFIIRVKFSRSADAP

AYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPP

R

OST577 - IgG4m - CD28 - Zeta (thus, a CAR
comprising the OST577 scFv, a mutated IgG4
hinge, a CD28 costimulatory domain, and a
zeta chain)
(SEQ ID NO: 13)
MEFGLSWVFLVALLRGVQCQVQLVESGGGVVQPGRSLRLSCAASGFTFSR

YGMHWVRQAPGKGLEWVAVISYDGSNKWYADSVKGRFTISRDNSKNTLFL

QMHSLRAADTGVYYCAKDQLYFGSQSPGHYWVQGTLVTVSSGGGGSGGGG

SGGGGSQSQLTQPPSVSVAPGQTARITCGGDNIGSKSVNWFQQKPGQAPV

LVVYDDNERPSGISERFSGSNSGNTATLTISRVEAGDEADYYCQVWDSSS

DHVVFGGGTKLTVLSGGGGSESKYGPPCPSCPAPPVAGPSVFLFPPKPKD

TLMISRTPEVTCVVVDVSQEDPEVQFNWYVDGVEVHNAKTKPREEQFQST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSPGKKD

PKFWVLVVVGGVLACYSLLVTVAFIIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

An example of a shRNA sequence against perforin
is as follows (where bold represents targeted
sequences to mRNA for degradation and italics
is the loop region of RNA molecule):
(SEQ ID NO: 14)
GACCCACCAGGACCAGTACCTACACAAAGTACTGGTCCTGGTGGGTC

(from PMID: 18393317)
Human microRNA 150 sequence (decreases
cytotoxicity in effector cells):
(SEQ ID NO: 15)
CUCCCCAUGGCCCUGUCUCCCAACCCUUGUACCAGUGCUGGGCUCAGACC

CUGGUACAGGCCUGGGGGACAGGGACCUGGGGAC

Human microRNA 27 sequence:
(SEQ ID NO: 16)
CUGAGGAGCAGGGCUUAGCUGCUUGUGAGCAGGGUCCACACCAAGUCGUG

UUCACAGUGGCUAAGUUCCGCCCCCCAG

Alternative hinge domain for a chimeric antigen receptor with Domain 3 of human CD4 (114 aa's) in bold inserted for the CH2 domain of IgG1 Fc region (113 aa's), and GSG linker on N-terminus of domain follows. In specific cases, the hinge is located between the single chain variable fragment and the transmembrane domain, and replicates the same size as a fully IgG Fc domain based hinge.

(SEQ ID NO: 17)
EPKSCDKTHTCPPCPGSGFQKASSI VYKKEGEQVE FSFPLAFTVE

KLTGSGELWW QAERASSSKSWITFDLKNKE VSVKRVTQDP

KLQMGKKLPL HLTLPQALPQ YAGSGNLTLALEAKTGKLHQEVNLVVM

GQPREPQ VYTLPPSRDE LTKNQVSLTC LVKGFYPSDI

AVEWESNGQP ENNYKTTPPV LDSDGSFFLY SKLTVDKSRW

QQGNVFSCSV MHEALHNHYT QKSLSLSPGKK

An example of IgG4m sequence is as follows, including a BamHI site at the beginning for cloning, with the subsequent sequence being a codon-optimized sequence for human IgG4 Fc domain with hinge, while also containing mutations to abrogate receptor binding:

(SEQ ID NO: 18)
GGATCCGAGAGTAAATACGGGCCGCCATGTCCTTCCTGCCCAGCCCCGCC

CGTGGCTGGCCCCTCCGTTTTCCTATTCCCTCCCAAGCCGAAGGATACCT

TGATGATcTCACGCACGCCAGAGGTTACTTGCGTCGTCGTTGATGTTTCA

CAGGAAGATCCTGAGGTCCAATTTAACTGGTATGTAGATGGAGTCGAGGT

GCATAACGCAAAGACGAAACCgCGgGAAGAGCAGTTCCAATCAACTTACA

GGGTGGTGAGTGTCCTGACAGTGTTACACCAGGACTGGCTCAACGGGAAG

GAGTACAAGTGCAAAGTAAGTAACAAGGGACTGCCCAGCTCTATCGAGAA

AACAATTTCCAAGGCCAAGGGTCAGCCaCGAGAACCACAAGTcTACACAC

TCCCCCCCTCGCAGGAAGAAATGACCAAGAATCAGGTAAGCCTGACATGT

CTTGTCAAAGGCTTCTATCCAAGCGACATCGCGGTGGAGTGGGAGTCCAA

TGGACAGCCCGAAAACAAcTATAAAACCACCCCTCCAGTGCTGGACAGCG

ACGGCTCCTTTTTTCTTTAT*agc*AGACTGACCGTGGACAAATCTCGGTGG

CAGGAAGGTAATGTGTTTTCTTGTAGCGTGATGCAT GAG GCT CTG

```
-continued
CAC AAC CAC TAC ACG CAG AAG AGC CTC TCC CTG TCT

CCG GGT AAA

IgG4m amino acid sequence:
                                        (SEQ ID NO: 19)
G S E S K Y G P P C P S C P A P P V A G P S V F L

F P P K P K D T L M I S R T P E V T C V V V D V S

Q E D P E V Q F N W Y V D G V E V H N A K T K P R

E E Q F Q S T Y R V V S V L T V L H Q D W L N G K

E Y K C K V S N K G L P S S I E K T I S K A K G Q

P R E P Q V Y T L P P S Q E E M T K N Q V S L T C

L V K G F Y P S D I A V E W E S N G Q P E N N Y K

T T P P V L D S D G S F F L Y S R L T V D K S R W

Q E G N V F S C S V M H E A L H N H Y T Q K S L S

L S P G K
```

Additional single chain variable fragments that can be employed in chimeric antigen receptors are listed below:
  scFv A5 (against HBsAg, Reference PMID: 14597165)
  VHH-S4 (against HBsAg, Reference PMID: 19085971)
  VHH-S5 (against HBsAg, Reference PMID: 19085971)
  HzKR127 (against PreS1, Reference PMID: 18176536)
  KR359 (against PreS1, Reference PMID: 10772975)
  2B6 (against PreS1, Reference PMID: 26888694)
  2D9 (against PreS1, Reference PMID: 26888694)
  2E7 (against PreS1, Reference PMID: 26888694)
  2G3 (against PreS1, Reference PMID: 26888694)
  ADRI-2F3 (against HBsAg, Reference PMID: 25923526)
  E6F6 (against HBsAg, Reference PMID: 26423112)
  HB-C7A (against HBsAg in chimps, Reference PMID: 18479762)
  scFv 1C9 (against HBV core protein, PMID: 10385671

III. Examples of Cells Expressing the CAR Compositions

In specific cases a cell is transduced with a CAR of the disclosure. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells, which do not contain a recombinantly introduced nucleic acid. In embodiments of the invention, a host cell is a T cell, including a cytotoxic T-cell (also known as TC, Cytotoxic T Lymphocyte, CTL, T-Killer cell, cytolytic T cell, CD8+ T-cells, CD4+ T-cells, or killer T-cells); NK cells and NKT cells are also encompassed in the disclosure.

In one aspect, provided herein is a cell that has been genetically engineered to express one or more CARs. In certain embodiments, the genetically engineered cell is, e.g., a T lymphocyte (T-cell), a natural killer (NK) T-cell, or an NK cell. In certain other embodiments, the genetically engineered cell is a non-immune cell, such as a stem cell, e.g., a mesenchymal stem cell (MSC), a neuronal stem cell, a hematopoietic stem cell, an induced pluripotent stem cell (iPS cell), or an embryonic stem cell, for example. In specific embodiments, the cell also comprises an engineered CAR or any other genetic modification that may enhance its function.

In certain embodiments, it is contemplated that RNAs or proteinaceous sequences may be co-expressed with other selected RNAs or proteinaceous sequences in the same cell, such as the same immune or stem cell. Co-expression may be achieved by co-transfecting the cell with two or more distinct recombinant vectors. Alternatively, a single recombinant vector may be constructed to include multiple distinct coding regions for RNAs, which could then be expressed in cells transfected with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells syngeneic cells, or allogeneic cells. The host cell can be any prokaryote or eukaryotic cell, but in specific embodiments it is a eukaryotic cell. In specific embodiments, the host cell is a bacterium, an insect, fungal, plant or animal cell. It is particularly envisaged that the recited host may be a mammalian cell, more preferably a human cell or human cell line. Particularly preferred host cells comprise immune cells (including myeloid and lymphoid lineages) and hematopoietic stem cells, which give rise to all lineages of immune cells.

One embodiment relates to a process for the production of a composition of the disclosure, the process comprising culturing a host cell defined herein above under conditions allowing the expression of the CAR construct, and the cell or a plurality of cells is provided to the individual. The conditions for the culturing of cells harboring an expression construct that allows the expression of the CAR molecules are known in the art, as are procedures for the purification/recovery of the constructs when desired. The described nucleic acid molecule or vector that is introduced in the host cell may either integrated into the genome of the host or it may be maintained extrachromosomally.

In one embodiment, the host cell is a genetically engineered T-cell (e.g., cytotoxic T lymphocyte) comprising a CAR and in some embodiments the cell further comprises an engineered TCR, chimeric cytokine receptor, and so forth. Naturally occurring T-cell receptors comprise two subunits, an α-subunit and a β-subunit, each of which is a unique protein produced by recombination event in each T-cell's genome. Libraries of TCRs may be screened for their selectivity to particular target antigens. An "engineered TCR" refers to a TCR that has a high-avidity and reactivity toward target antigen that is selected, cloned, and/or subsequently introduced into a population of T-cells used for adoptive immunotherapy. In contrast to engineered TCRs, CARs are engineered to bind target antigens in an MEW independent manner.

In certain embodiments, the HBV-specific CAR-expressing cells encompass a plurality of cells, including a plurality of T cells, such as one example that is depleted of CD45RA cells, or has a knockout or shRNA reduction against one or more particular molecules, such as TCR molecules, making it suitable for allogeneic use. In at least some cases, the cells comprise a knockout or shRNA against beta macroglobulin or MEW class I molecules. Any knockout may be generated using a CRISPR/Cas9, TALEN, homing endonucleases, zing finger nucleases, or other site directed DNA nucleases in the art.

In cases wherein the cells are allogeneic, they may be derived from an induced pluripotent stem cell (iPS) or embryonic stem cell (ES) cell, or other stem cell.

In some cases, the immune cells comprise multiple CARs each of which target multiple epitopes of the same pathogen, including the same pathogenic protein, or they may target different pathogenic proteins.

In specific embodiments, cells used in the methods are contacted with or delivered along with anti-PD1, anti-PDL1, or anti-CTLA4 antibody-based inhibitors, also known as checkpoint inhibitors. The PD1/PDL1 and CTLA4 targets are merely representative of this class of drugs, and are not meant to be exclusive. Examples of these checkpoint inhibitors that could be utilized include pembrolizumab, nivolumab, atezolizumab, and ipilimumab.

It is further envisaged that a pharmaceutical composition of the disclosure comprises a host cell transformed or transfected with a vector defined herein. The host cell may be produced by introducing at least one of the above described vectors or at least one of the above described nucleic acid molecules into the host cell. The presence of the at least one vector or at least one nucleic acid molecule in the host may mediate the expression of a gene encoding the above described be specific CAR constructs.

The pharmaceutical composition of the disclosure may also comprise a proteinaceous compound capable of providing an activation signal for immune effector cells useful for cell proliferation or cell stimulation. In the light of the present disclosure, the "proteinaceous compounds" providing an activation signal for immune effector cells may be, e.g. a further activation signal for T-cells (e.g., a further costimulatory molecule: molecules of the B7-family, OX40 L, 4-1BBL), or a further cytokine: interleukin (e.g., IL-2, IL-7, or IL-15), or an NKG-2D engaging compound. The proteinaceous compound may also provide an activation signal for immune effector cell which is a non-T-cell. Examples for immune effector cells which are not T-cells comprise, inter alia, NK cells, or NKT-cells.

T-cells can also be further genetically modified to enhance their function, particularly concerning persistence inside the individual being treated. Examples include, but are not limited to, the transgenic expression of cytokines (e.g. IL2, IL7, IL15), expression of cytokine receptors (e.g., IL7R alpha, IL2R alpha) silencing of negative regulators (for example SHP-1, FAS), expression of chemokine receptors (e.g., CXCR2, CCR2b), dominant negative receptors (e.g. dominant negative TGFβRII), and/or expression of so-called 'signal converters' that convert a negative into a positive signal (e.g. IL4/IL2 chimeric cytokine receptor, IL4/IL7 chimeric cytokine receptor, or TGFβRII/TLR chimeric receptor).

In many situations one may wish to be able to kill the genetically engineered T-cells, where one wishes to terminate the treatment, the cells become neoplastic, in research where the absence of the cells after their presence is of interest, or other purpose. For this purpose one can provide for the expression of certain gene products in which one can kill the engineered cells under controlled conditions, such as inducible suicide genes. Such suicide genes are known in the art, e.g., the iCaspase9 system in which a modified form of caspase 9 is dimerizable with a small molecule, e.g., AP1903.

IV. Examples of Methods of Making and Using the CAR Compositions and Cells Expressing the CARs In various embodiments CAR constructs, nucleic acid sequences, vectors, host cells, as contemplated herein and/or pharmaceutical compositions comprising the same are used for the prevention, treatment or amelioration of at least one symptom of a HBV-associated disease or condition.

In particular embodiments, provided herein is a method of treating an individual who has an HBV infection, comprising the step of providing a therapeutically effective amount of a plurality of any of the HBsAg-specific CAR-expressing cells of the disclosure to the individual. In certain embodiments, the method of treating comprises ameliorating one or more symptoms of the HBV infection, e.g., jaundice. In certain embodiments, the therapeutically effective amount is an amount that results in amelioration of one or more symptom of the HBV infection. In certain other embodiments, the therapeutically effective amount is an amount that results in a reduction in HBV viral titer, for example, in a serum sample or tissue biopsy, e.g, liver biopsy, from the individual. In other specific embodiments, the individual is a mammal, e.g., a human.

As used herein "treatment" or "treating," includes any beneficial or desirable effect on the symptoms or pathology of a disease or pathological condition, and may include even minimal reductions in one or more measurable markers of the disease or condition being treated, e.g., HBV infection and related medical condition(s). Treatment can involve optionally either the reduction or amelioration of one or more symptoms of the disease or condition, or the delaying of the progression of at least one symptom of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In particular embodiments of the present disclosure, cells modified to express one or more CAR constructs, at least one of which target one or more Hepatitis B antigens (optionally wherein the one or more agents is not C8 scFv or 5a19 scFv), are provided in a therapeutically effective amount to an individual in need thereof. The individual may be seropositive for HBV, diagnosed with HBV, exposed to HBV, or at risk for HBV, for example. In some cases at least, the method encompasses production of HBV CAR-expressing cells, such as by transduction of immune cells (T cells, NK cells, NKT cells, and the like) with a polynucleotide that expresses the HBV CAR, including an expression vector that encodes the HBV CAR. The administration of the HBV CAR-expressing cells may be via any suitable route to the individual, including locally or systemically. In specific embodiments the HBV CAR-expressing cells are delivered intravenously, orally, rectally, topically, intramuscularly, by infusion, enterically, nasally, by inhalation, sublingually, bucally, transdermally, subcutaneously, and so forth. When the cells are delivered to an individual, they may be delivered in a pharmaceutically acceptable carrier or excipient. In certain embodiments, subsequent to administration, said nucleic acid molecules or vectors may be stably integrated into the genome of the subject.

In certain embodiments of the disclosure, cells expressing a CAR that targets at least one HBV antigen are provided. HBV CAR-expressing cells may be of any kind, including prokaryotic cells that may be used to generate the HBV CAR by recombinant means or eukaryotic cells, such as immune cells, including T cells, NK cells, and NKT cells, for example.

In particular embodiments, polynucleotides that comprise sequence that encodes part or all of an HBV CAR are included. The polynucleotides may be linear or circular and may be DNA or RNA. The polynucleotides may be comprised on a vector of any kind, including a viral vector or non-viral vector, and in such cases the coding region that expresses the HBV CAR may be regulated by one or more regulatory sequences. In certain cases, a polynucleotide that encodes a nucleic acid (miRNA, shRNA, or siRNA) that target a gene to be reduced in expression (such as perforin, granzyme A, B, C, D, Fas, TNFalpha, and/or TRAIL) may or may not be the same polynucleotide that encodes the HBV CAR. Thus, in certain embodiments one expression vector encodes the HBV CAR and a second expression vector encodes a nucleic acid that target a gene to be reduced in expression, whereas in other embodiments the HBV CAR and the nucleic acid that targets a gene to be reduced in expression are on the same vector.

In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying of HBV.

Particular doses for therapy may be determined using routine methods in the art. However, in specific embodiments, the T cells are delivered to an individual in need thereof once, although in some cases it is multiple times, including 2, 3, 4, 5, 6, or more times. When multiple doses are given, the span of time between doses may be of any suitable time, but in specific embodiments, it is weeks or months between the doses. The time between doses may vary in a single regimen. In particular embodiments, the time between doses is 2, 3, 4, 5, 6, 7, 8, 9, 10, or more weeks. In specific cases, it is between 4-8 or 6-8 weeks, for example. In specific embodiments, one regimen includes the following dose regimen:

Particular doses for CAR modified cells include $10^5$ cells/m$^2$, $10^6$ cells/m$^2$, $10^7$ cells/m$^2$, $10^8$ cells/m$^2$, $10^9$ cells/m$^2$, or $10^{10}$ cells/m$^2$ and ranges there between. Doses on the higher end of the range are necessary when cells have limited persistence or are irradiated prior to infusion.

In particular cases the individual is provided with therapeutic T-cells engineered to comprise a CAR specific for one or more HBV antigens. With multiple administrations, the cells may or may not be provided to the individual in different delivery routes. The cells may be delivered by injection into the liver or intravenously or orally, for example. Routine delivery routes for such compositions are known in the art.

Expression vectors that encode the HBV-specific CARs can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. For example, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the cells by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc. Other markers included proteins expressed on the cell surface, including CD19, CD34, epidermal growth factor receptor, or nerve growth factor receptor, etc.

In some instances, one may have a target site for homologous recombination, where it is desired that a construct be integrated at a particular locus. For example, can knockout an endogenous gene and replace it (at the same locus or elsewhere) with the gene encoded for by the construct using materials and methods as are known in the art for homologous recombination. For homologous recombination, one may use either .OMEGA. or O-vectors. CRISPR/Cas9, zinc finger nucleases, TALE nucleases, meganucleases, and other site directed nucleases may be used to target and cleave a specific site in the genome to promote homologous recombination.

The constructs may be introduced as a single DNA molecule encoding at least the HBV-specific CAR and optionally another gene, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

The exemplary T cells that have been engineered to include the HBV-specific CAR construct(s) are then grown in culture under selective conditions and cells that are selected as having the construct may then be expanded and further analyzed, using, for example; the polymerase chain reaction for determining the presence of the construct in the host cells. Once the engineered host cells have been identified, they may then be used as planned, e.g. expanded in culture or introduced into a host organism.

Depending upon the nature of the cells, the cells may be introduced into a host organism, e.g. a mammal, in a wide variety of ways. The cells may be introduced at the site of the tumor, in specific embodiments, although in alternative embodiments the cells home to the cancer or are modified to home to the infected tissue. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The cells may be administered as desired. Depending upon the response desired, the manner of administration, the life of the cells, the number of cells present, various protocols may be employed. The number of administrations will depend upon the factors described above at least in part.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells, which could be administered to the population at large, each patient would be monitored for the proper dosage for the individual, and such practices of monitoring a patient are routine in the art.

In another aspect, provided herein is a method of treating an individual having a HBV antigen-positive tumor cell, comprising administering to the individual a therapeutically effective amount of cells expressing at least HBV antigen-specific CAR. In a related aspect, provided herein is a method of treating an individual having an infected cell or tumor cell positive for HBsAg (of liver origin, for example), comprising administering to the individual a therapeutically effective amount of cells expressing at least HBV antigen-specific CAR. In a specific embodiment, said administering results in a measurable decrease in the HBV-positive cells in the individual. In various embodiments, the effectiveness of the therapy may be measured by alpha-feto protein levels in the serum (which is secreted by liver tumors), and the size of the tumor in computed tomography imaging, for example.

Embodiments relate to a kit comprising cells as defined herein, CAR constructs as defined herein, a nucleic acid sequence as defined herein, and/or a vector as defined herein. It is also contemplated that the kit of this disclosure comprises a pharmaceutical composition as described herein above, either alone or in combination with further medicaments to be administered to an individual in need of medical treatment or intervention.

The cells that are delivered as treatment may be autologous or allogeneic to the individual, and the cell product may be a primary cell isolate from individuals. The cell product may comprise an immune cell, such a T cell, NK cell, or an NKT cell. In other embodiments, the cells may be hematopoietic stem cells, which give rise to all immune progenitors, and can be transduced in vitro or in vivo intra-bone marrow or via intravenous injection. In specific embodiments, the cell products are immune cell lines that are capable of continuous growth. Examples of cell lines of NK lineage include NK-92, NKL, and NK-YS cell lines. Examples of cell lines of T cell lineage include TALL-104 or C-Cure 707 cell line. A cell product may be an allogeneic NK-T cell with restricted TCR to CD1d.

In particular examples, one can harvest allogeneic T cells from healthy, random donors and transduce the cells with one or a mixture of 2 or 3 CARs harboring different scFv sequences for global coverage of HBV serotypes. In specific embodiments, the cells harbor a construct that comprises an shRNA for cytopathic reduction as desired, such as against the perforin or granzyme B proteins, which would abrogate canonical T cell mediated cytotoxicity. The cells are delivered (for example by infusion) to a patient with chronic HBV. The CAR T cells will home to the liver, and may persist for days 11-28 days before dying off from exhaustion. If the disease is not improved upon in one infusion cycle, another autologous or allogeneic product (for example, by infusion). The second delivery may occur within 14-180 days after the first, to avoid too much inflammation at one time in the liver. Subsequent deliveries following the first and second deliveries may occur. In specific embodiments, there are 7-14 day cycles where the cells are delivered until their levels drop, immediately followed by another delivery and persistence, etc., and the cycles may be repeated until desired to be stopped, for example upon improvement of at least one symptom (absence of ALT flares), hepatitis B e-antigen (HBeAg) seroconversion, anti-HBsAg seroconversion or upon serum HBsAg clearance of the infection. In specific embodiments, within 1 to 10 courses of therapy, HBV is cleared from the liver. Unlike other HBV strategies, this does not depend on an anergic and defective host immune response to suddenly re-awaken. In specific cases, the individuals are provided one or more treatments to prevent viral spread during treatment, such as reverse transcriptase inhibitors and/or recombinant interferon-alpha derivatives.

Allogeneic cell therapy strategies for HBV treatment has two purposes. In the first, there is predictable pharmacokinetics and quality of the cell product, which is useful in targeting the liver, which must not be harmed in an acute way. Methods and compositions of the present disclosure ensures a level of safety with allogeneic products being potentially rejected by HLA-incompatability limiting therapeutic lifespan and alleviating any potential adverse events, serving as built-in safety feature. In the second, the disclosure in one embodiment allows for scalable manufacturing and packaging of an allogeneic cell product into suitable containers for worldwide, versus current autologous patient-specific manufacturing for tumor schemes.

For individuals with HBV who have some level of an immunocompromised state, a T cell product that has the TCR genes knocked out is useful to avoid graft-versus-host disease (GVHD). Methods using CRISPR/Cas9, zinc finger nucleases, TALE nucleases, homing endonucleases, or meganucleases may be employed in such a case. Another strategy employs homologous recombination strategies in order to remove expression. In addition or alternatively, the T cells could be irradiated prior to infusion, which would decrease their lifetime to around 2 days, although in some cases this is less ideal.

In some embodiments the methods of the disclosure provide a particular advantage of strategy for individuals who cannot sustain significant bystander organ damage. An example would be cirrhotic HBV patients, who likely have contra-indications for other HBV therapeutic strategy (particularly ones activating the immune system). Another example would be immunocompromised individuals with an allograft infection, or with chronic kidney disease. In these individuals, treatment is required in order to save the organ, but the treatment cannot be so destructive as to cause more harm during therapy.

One strategy of methods and compositions of the disclosure includes the benefits in the remarkable sensitivity of CAR T cells to low antigen production (for example, 10,000 antigens versus 100,000 for an antibody). In certain aspects this is useful in treating hepatitis B virus e antigen (HBeAg)-negative individuals with lower replication levels of virus in addition to individuals with occult HBV, wherein the serum is negative for HBsAg but HBV DNA can still be detected.

In some embodiments, there is a method of treating an infected cell non-cytopathically, thereby lessening direct harm to tissues while maximizing cytokine secretion. In certain cases, the method comprises the step of utilizing a CAR that lacks signaling endodomains for perforin/granzyme secretion, such as the zeta chain and CD16 gamma chain, while retaining various other costimulatory domains important in cytokine secretion. In particular cases cells harboring the CARs are modified to reduce expression of perforin, granzyme-A, granzyme-B, granzyme-C, granzyme-D, Fas, Fas receptor, TNF-alpha, and/or TRAIL (for example, or by genetic knockout (using CRISPR/Cas9, TALE nuclease, or zinc finger nuclease system, for example) or by homologous recombination or shRNA-targeting the desired gene product or microRNAs). In specific embodiments, micoRNA's that target perforin and granzyme mRNA transcripts are utilized to depress their levels of expression (for example, human microRNA-150 or human microRNA-27a*).

In particular embodiments, there are methods of treating humans with HBV infection by providing an effective amount of allogeneic cell product that is irradiated before infusion into the individual in order to prevent further cell expansion of the cell product in the individual, and in some cases one or more deliveries of the cell product are provided to the individuals. In certain cases the individual is immunocompromised.

In some embodiments there is a method of targeting HBV-infected cells or HBV, wherein the targeted antigen is an extracellular antigen located on the surface of the HBV-infected cell or the surface of the pathogen. In some cases a peptide expressed on an MEW class I molecule is targeted using a single chain antibody mimicking T cell receptor (TCR) function.

In some embodiments there is a method of treating an HBV infection, wherein the liver infected is targeted with a T cell attenuated for toxicity with a CAR toward an antigen expressed in that organ, producing temporary inflammation and cytokine production in the organ to purge the HBV infection.

In certain embodiments, there is a method of treatment of administration of antibodies against an HBV antigen prior to treatment with HBV CAR-expressing cells, in order to reduce HBV antigen levels prior to CAR-T cell infusion, and help promote T cell homing to the liver site and therapeutic response. One or more administrations of the antibodies may be employed. In other embodiments, antibodies may be administered after the infusion of CAR-T cells, in order to promote increased anti-HBV efficacy and therapeutic response.

In one embodiment, there is a method of treatment comprising administering reverse transcriptase inhibitors (examples: lamivudine, adefovir dipivoxil, telbivudine, tenofovir alafenamide, tenofovir, and entecavir) prior to and during CAR therapy, in order to prevent the recovery and rebound of viral genome levels. One or more administrations of the inhibitors may be utilized. Reverse transcriptase inhibitor therapy may also be continued after elimination of CAR-T cells, in order to prevent later viral rebound and maintain the effects from therapy.

In some embodiments, the HBV-specific CAR T cells are utilized in conjunction with one or more other therapies FDA-approved for HBV infection. Future FDA approved medications for HBV treatment may also be considered in combination with CAR-T therapy. The therapy may or may not be one or more reverse transcriptase inhibitors. In specific embodiments, the additional therapy is lamivudine, adefovir, dipivoxiltelbivudine, entecavir, interferon alfa-2b, pegylated interferon, emtricitabine, tenofovir, tenofovir alafenamide, or a combination thereof.

EXAMPLES

The examples provided herewith are included to demonstrate particular embodiments of the disclosure. It should be appreciated by those of skill in the art that the techniques disclosed in the examples that follow represent techniques discovered by the inventor to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1

Chimeric Antigen Receptor Directed T Cells can Mediate Antiviral Effects Against Hepatitis B Virus in a Humanized Liver Model of Infection Chronic hepatitis B virus (HBV) can only be suppressed by current drugs today in most patients, and a need for a permanent cure for this patient population remains. In patients who clear acute HBV infection, an effective T cell response infiltrates the liver, but patients with chronic HBV have deficient antiviral T cells. This problem was addressed by engineering T cells with a chimeric antigen receptor (CAR), having specificity toward HBV surface antigen (HBsAg), which is noted to accumulate on the surface of infected hepatocytes.

Previous studies showed that HBsAg-targeted CAR T cells were efficacious in vitro at killing HBV+ cell lines and in clearing HBV covalently closed circular DNA (cccDNA) in primary human hepatocytes in cell culture. These HBV CAR T cells were also tested in a transgenic HBV mouse model, and exhibited a modest reduction in viral loads that was ultimately transient in vivo. However, CAR T cell levels rebounded and failed to persist. In particular, the cells appeared to be gone by week 3. The maximum decline in virus was at day 12 (cells were also observed in the liver at that date), with levels rebounding after that. (In the present work, the inventors continued seeing declines much longer than that and stabilization in response after therapy.) Because the clearance of HBV cannot be tested in the transgenic model, given that HBV is integrated into the host genome, CAR-T cell therapy was tested in a clinically relevant setting with authentic virus.

Figures 10A, 10B, 10C:
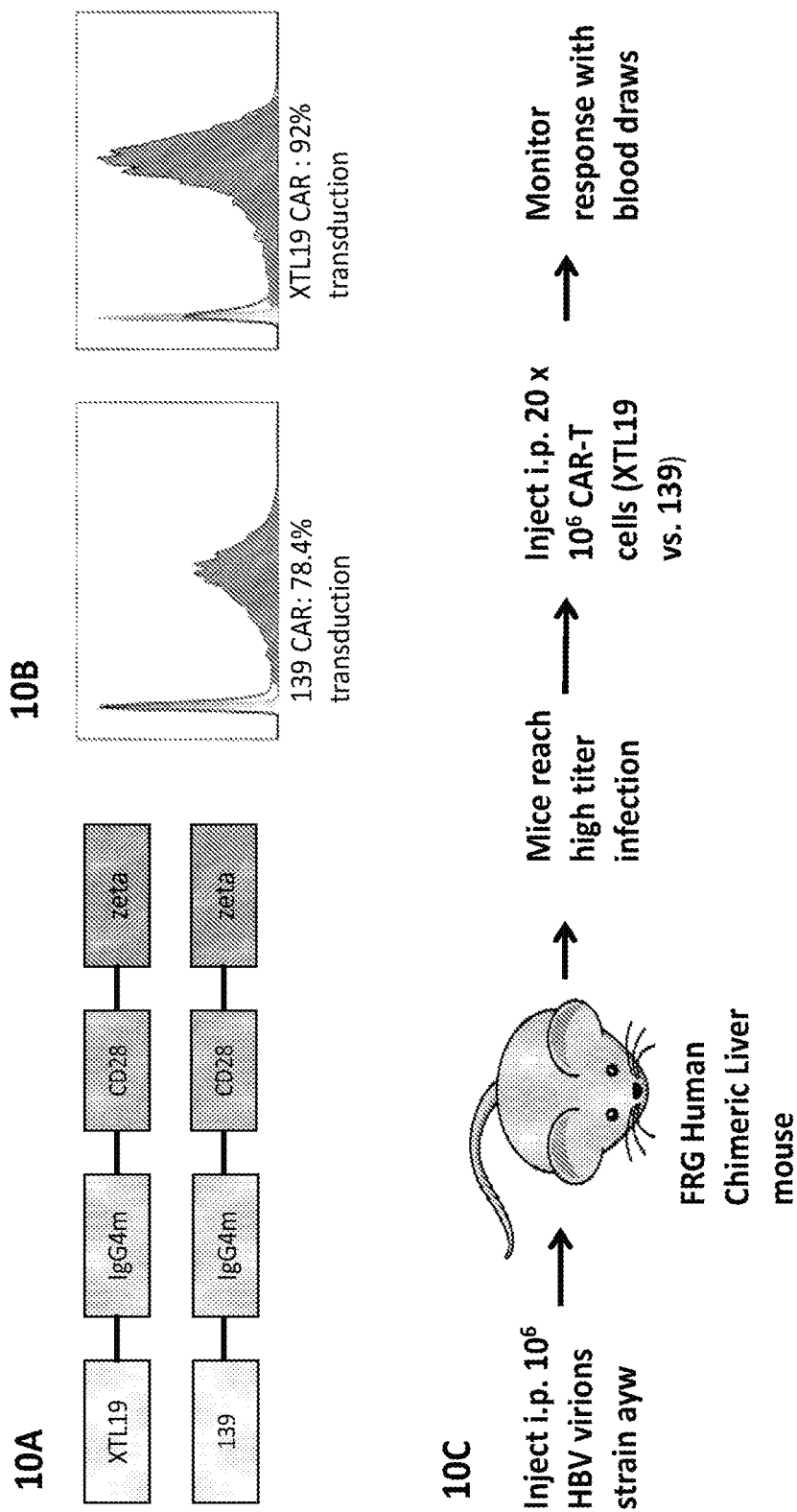
FIGS. 10A-10G show construction and homing of CAR-T cells into the humanized liver of HBV-infected mice. (10A) XTL19-IgG4m-CD28-Zeta (targeting HBsAg) and 139-IgG4m-CD28-Zeta (targeting EGFRvIII as a control) CAR constructs were cloned into SFG retroviral vectors to create vector for in vivo studies. (10B) CAR expression was confirmed by flow cytometry using anti-hIgG to identify extracellular domain. (10C) Human chimeric liver mice were infected with HBV. Upon reaching high levels, the prepared T cells were injected i.p. into mice and monitored overtime. (10D) Serum HBsAg levels were followed over time in XTL19 CAR-T treated mice. (10F) Serum DNA levels had a large initial increase post infusion, before rebounding. (10G) and (10E) DNA and HBsAg levels were normalized to their started level and average among mice. Only XTL-19 treated mice exhibited a significant decline versus 139 CAR-T control.
Figures 10D, 10E, 10F, 10G:
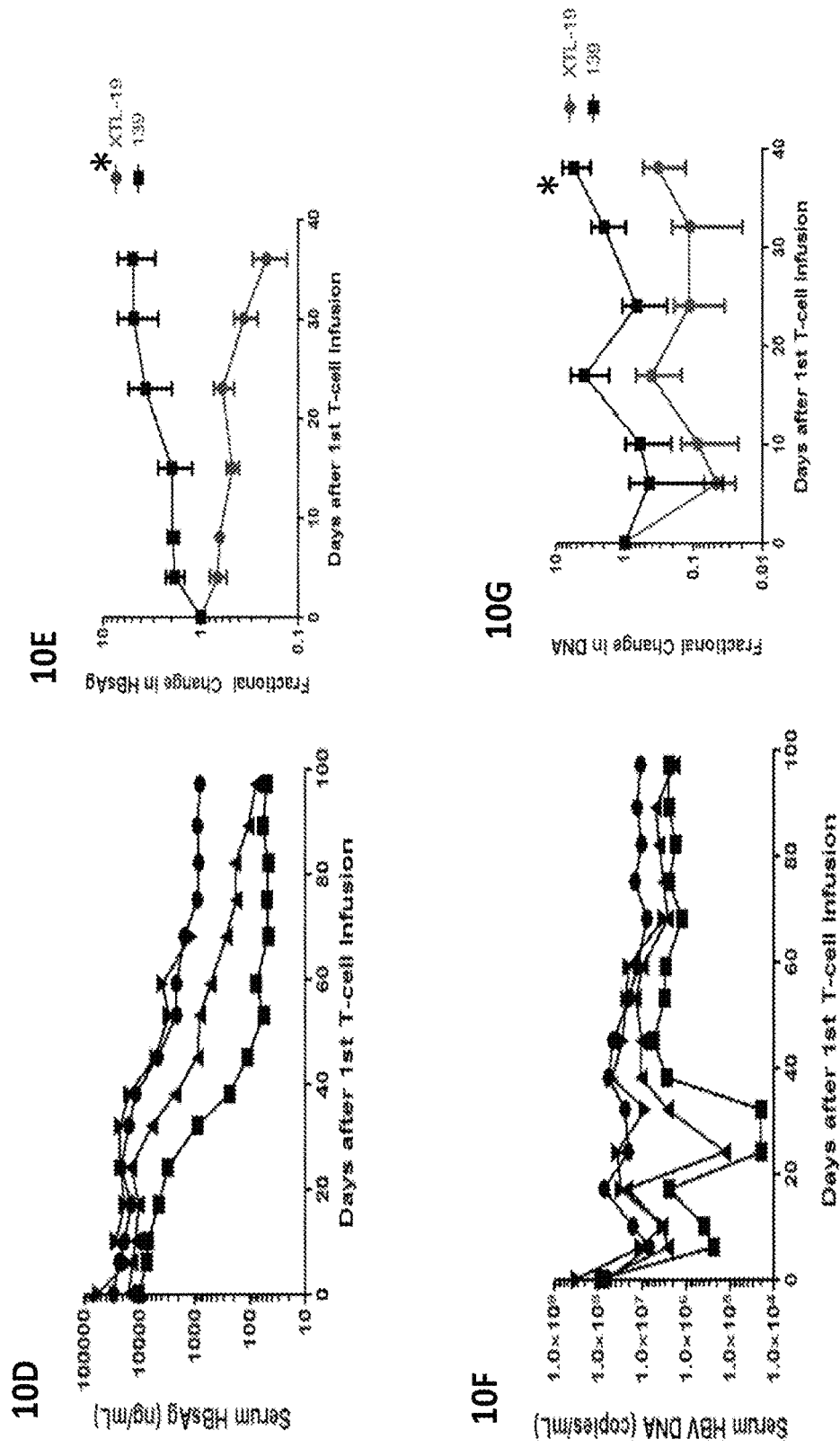

In the present study, humanized liver chimeric mice were employed, which are infectious for HBV and possess cccDNA genomes, affording direct translational significance to human patients. In this model, only human hepatocytes are infected with HBV. In order to facilitate clinical development, a new human single chain variable fragment (scFv) against HBsAg that would not be expected to provoke an immune response in patients was sought. Upon screening previously described antibody scFvs, an scFv was identified (19.79.5 scFv (referred to herein as XTL-19)) that in the CAR molecule context could potently activate T cells in vitro, resulting in complete killing of an HBV+ cell line at 1 week, while sparing an HBV− negative HepG2 control. Notably, a second CAR (utilizing 17.1.41 scFv, referred to herein as XTL-17) molecule had less activation effect indicating scFvs against HBV may be empirically tested by standard means in order to prove efficacy. Furthermore, the HBV CAR T cells released high levels of INF-gamma, IL-2, and TNF-alpha in response to both soluble and cell-associated HBsAg. These HBV CAR T cells were tested in the HBV-infected humanized liver mouse model, which displayed initial HBV levels ranging from $10^7$-$10^9$ copies/mL and 10-50,000 HBsAg ng/mL. A single dose of CART cells (20 million CART cells delivered intraperitoneally) into infected mice decreased serum HBsAg concentration by up to 2 logs, and decreased serum HBV DNA levels up to 3 logs, over one month post infusion (FIG. 10D). The CAR T cells mediates cytotoxic killing of HBV-infected hepatocytes, with a concurrent decreased in human serum albumin levels in the mice. CAR T cells directed to a non-HBV antigen had no antiviral effects. In summary, this data indicates that human T cells can successfully be engineered to selectively home to human HBV-infected liver, indicating similar potency in patients.

EXAMPLE 2

Chimeric Antigen Receptor Therapy with Reduced Cytotoxicity for Infectious Diseases The present disclosure provides a general strategy of cell-based immunotherapy to treat various viral indications, particularly in infections targeting crucial organs where toxicity may be an issue and cell death may not be desired, but rather cytokine secretion and activation host intracellular innate immune pathways and of more specific CTL and NK cell effectors is desired. This particularly has useful general applications of cell-based immunotherapy for treating individuals with compromised immune systems for viral infections.

Present embodiments include targeting of Hepatitis B virus, where the inventors have shown that administered HBV-specific CAR T cells are effective against HBV in a clinically-relevant mouse model. Demonstrated herein are optimizations over the prior art for a chimeric antigen receptor (CAR) design for this purpose. Also encompassed herein are additional modifications to attenuate toxicity. In embodiments herein, the body purges virus non-cytopathically, and in other embodiments helper T cell function is utilized in the body.

The present example provides studies in the development of a new chimeric antigen receptor against HBV specifically that is useful in targeting HBV diseases.

Figure 2:
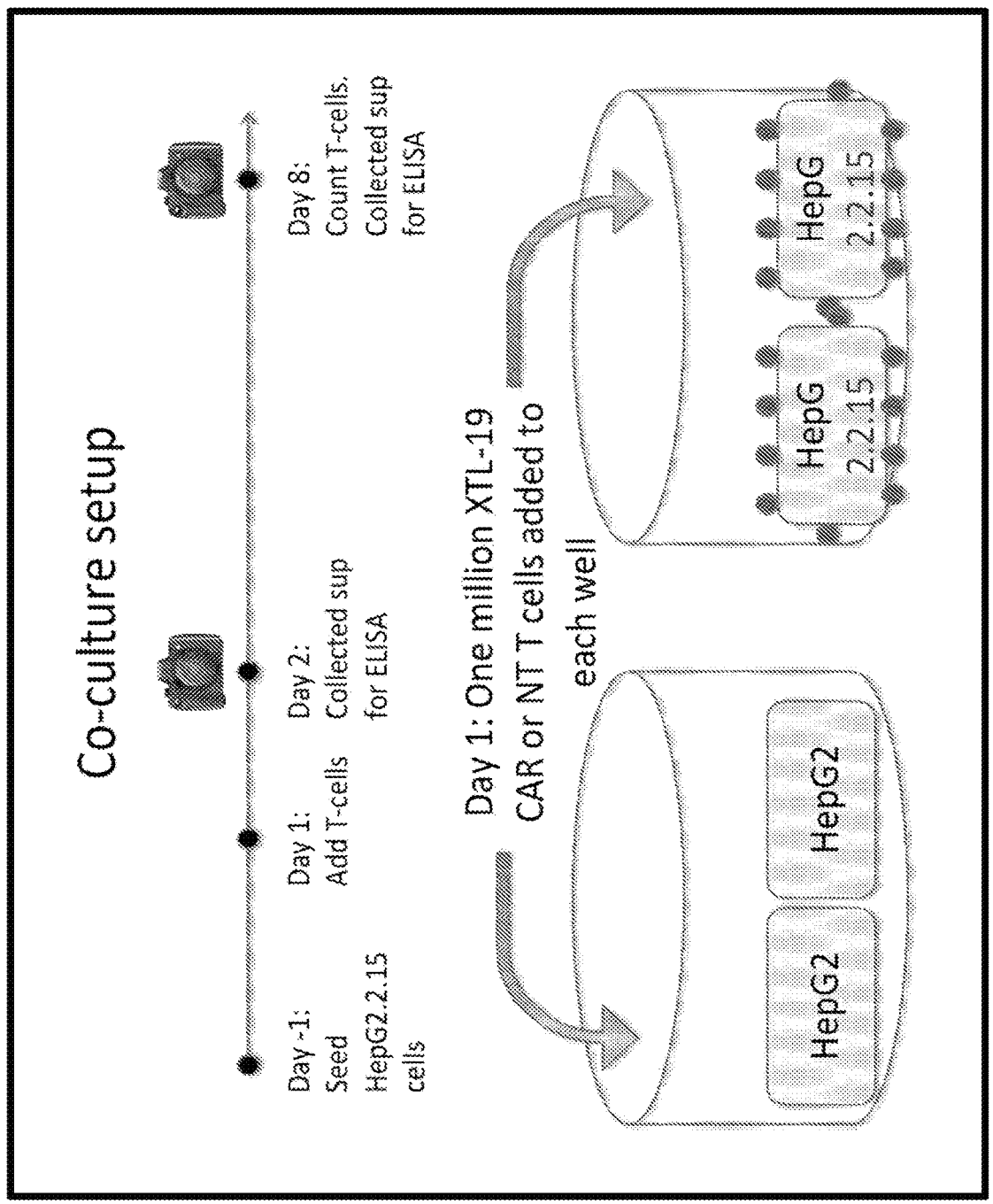
FIG. 2 is an illustration of co-culture setup with the CART cells of FIG. 1 and cells that were hepatitis B virus (HBV)-transfected HepG2.2.15 cells or control HepG2 cells.
Figure 3:
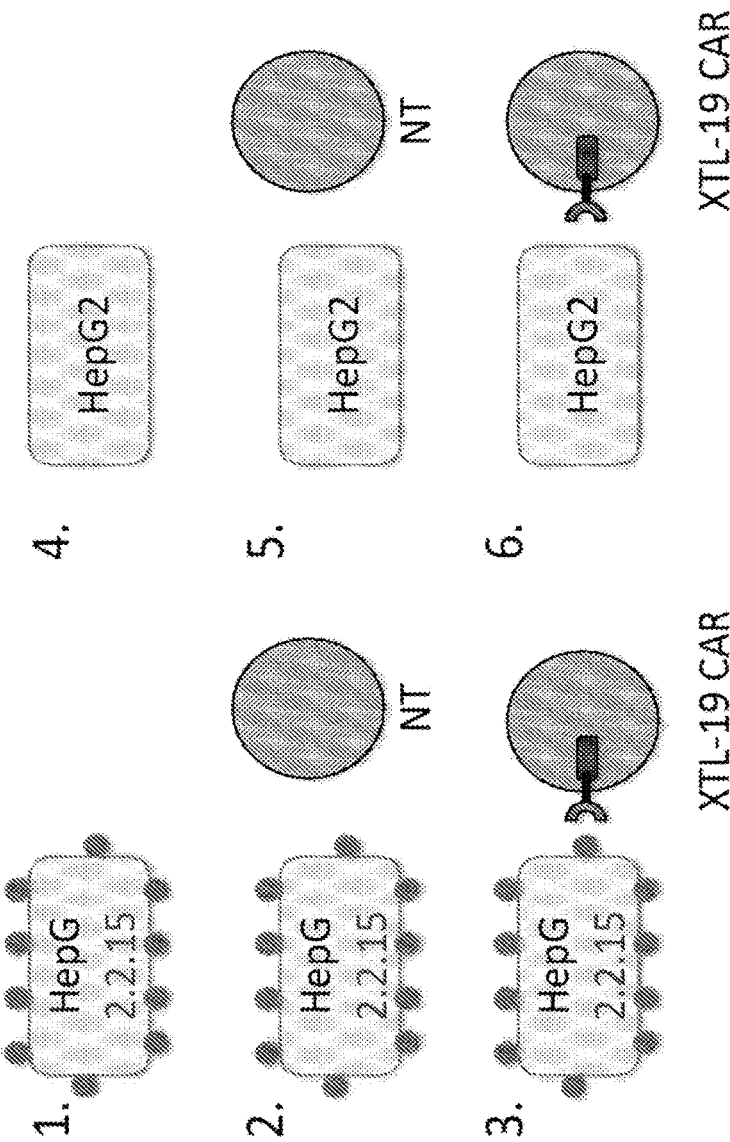
FIG. 3 is a schematic showing different combinations tested in the co-culture studies.
Figure 4:
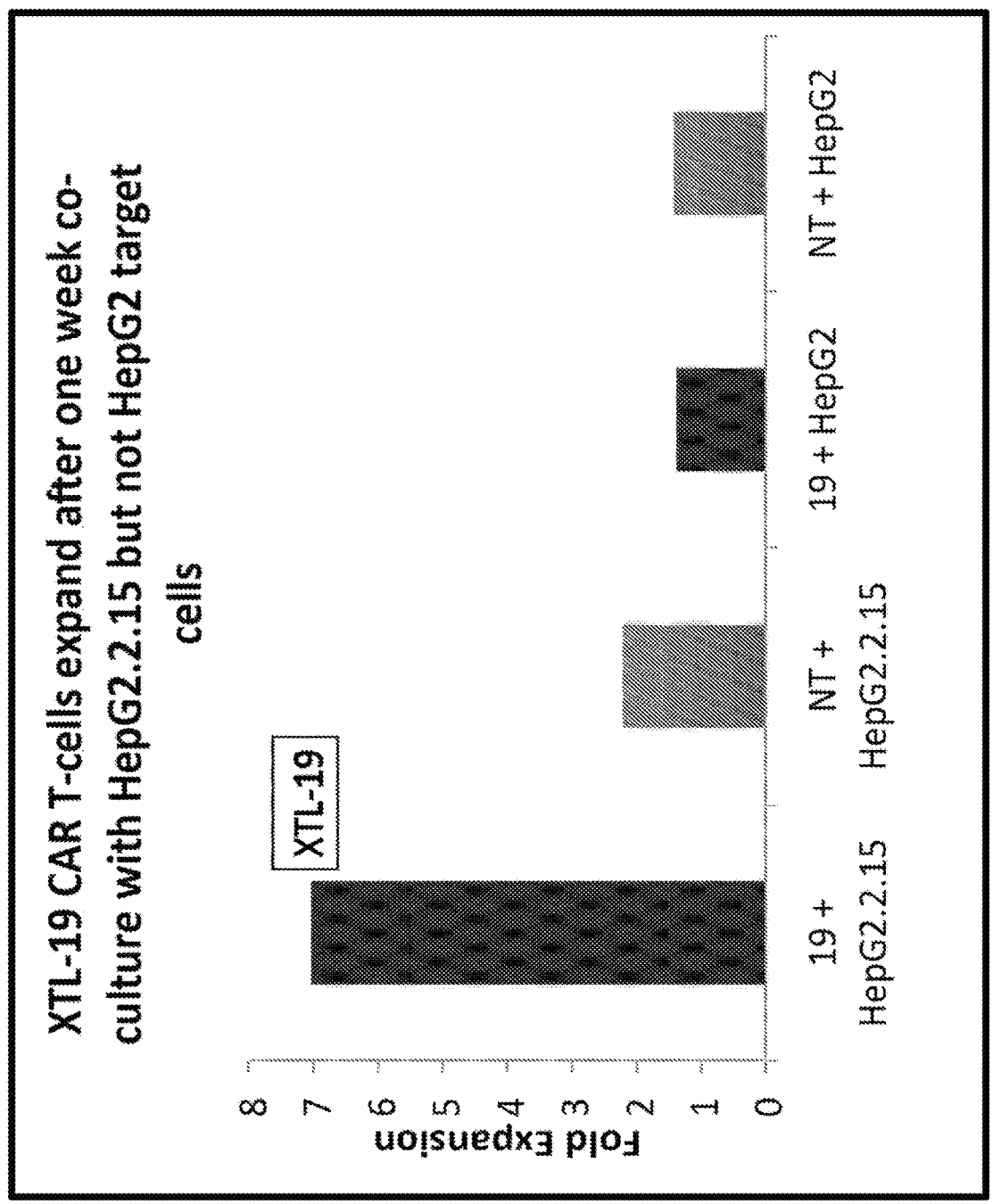
FIG. 4 shows that XTL-19 CAR T-cells expand after one week of co-culture with HepG2.2.15 cells but not the control HepG2 target cells.
Figure 5:
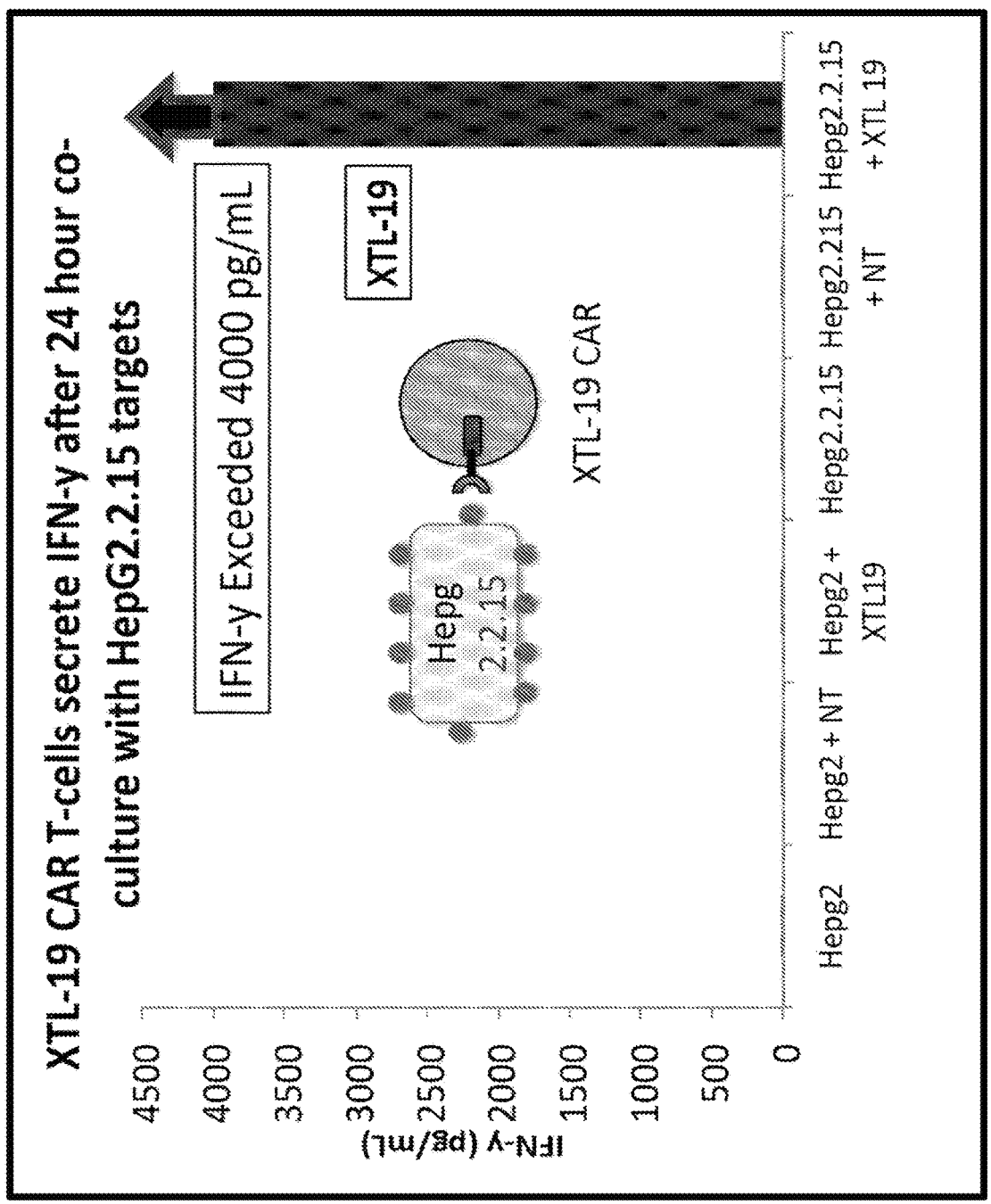
FIG. 5 demonstrates that XTL-19 CAR T-cells secrete IFN-γ after 24 hours of co-culture with HepG2.2.15 target cells.
Figure 6:
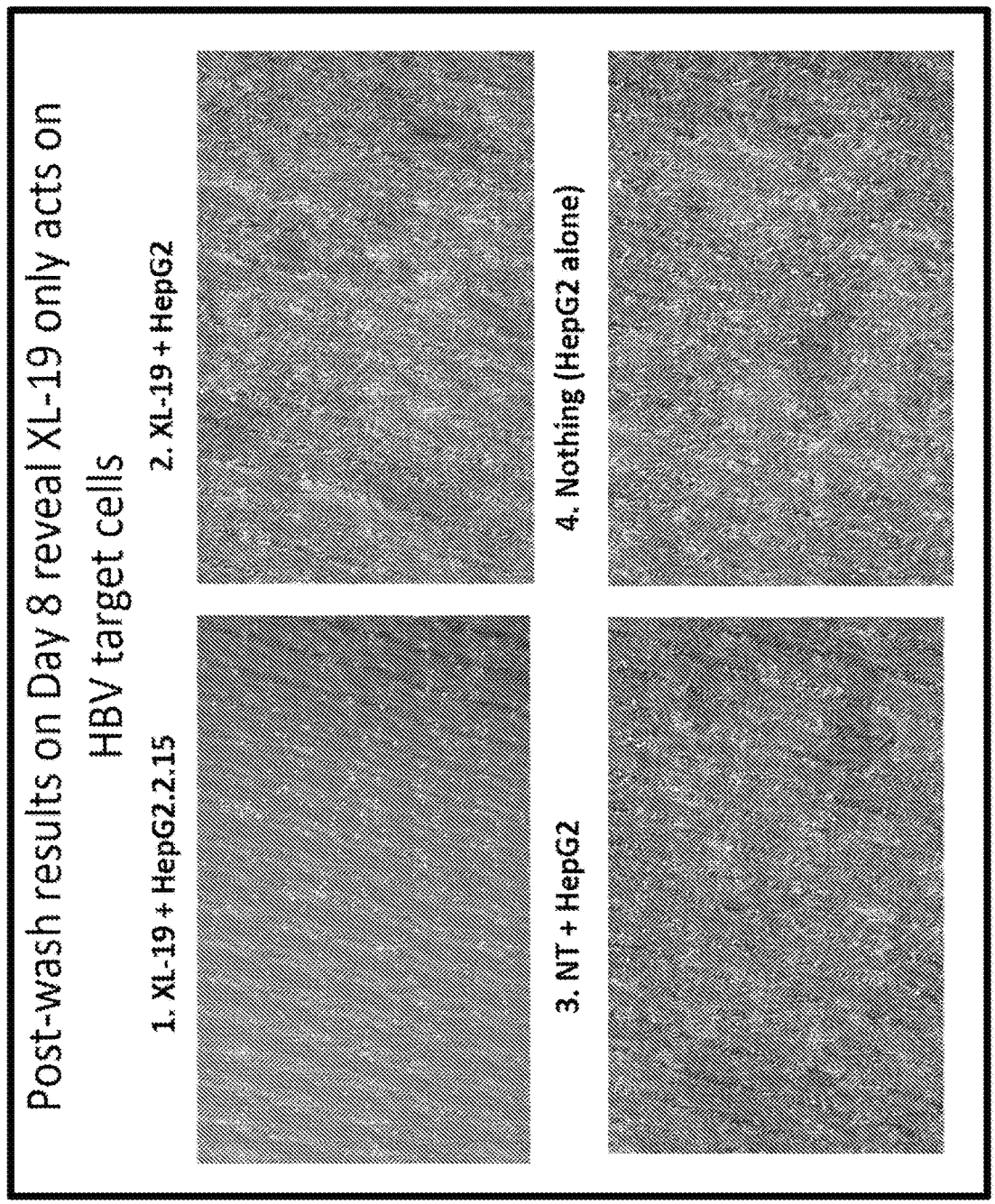
FIG. 6 provides post-wash results on Day 8 revealing XTL-19 only acts on HBV target cells.

Two HBV-specific CARs were constructed (FIG. 1). These CARs utilize the 19.79.5 scFv (referred to herein as XTL-19) and the 17.1.41 scFv (referred to herein as XTL-17), and an IgG1 hinge (CH2CH3). The XTL-17 or XTL-19 CAR T cells, or non-transformed T cells, were incubated with an HBV-positive cell line (HepG2.2.15) or an HBV-negative cell line (HepG2) (FIG. 2; FIG. 3). XTL-19 CAR T-cells expanded after one week of co-culture with HepG2.2.15 but not HepG2 target cells (FIG. 4). FIG. 5 shows that XTL-19 CAR T-cells secrete IFN-γ after 24 hours of co-culture with HepG2.2.15 cells, but not with HepG2 cells; cells not co-cultured with XTL-19 CAR T-cells, or cell line cells co-cultured with non-transformed T cells, produced undetectable levels of IFN-γ. FIG. 6 demonstrates the absence of tumor cell lines upon incubation with the XTL-19 CAR T cells.

Figure 7:
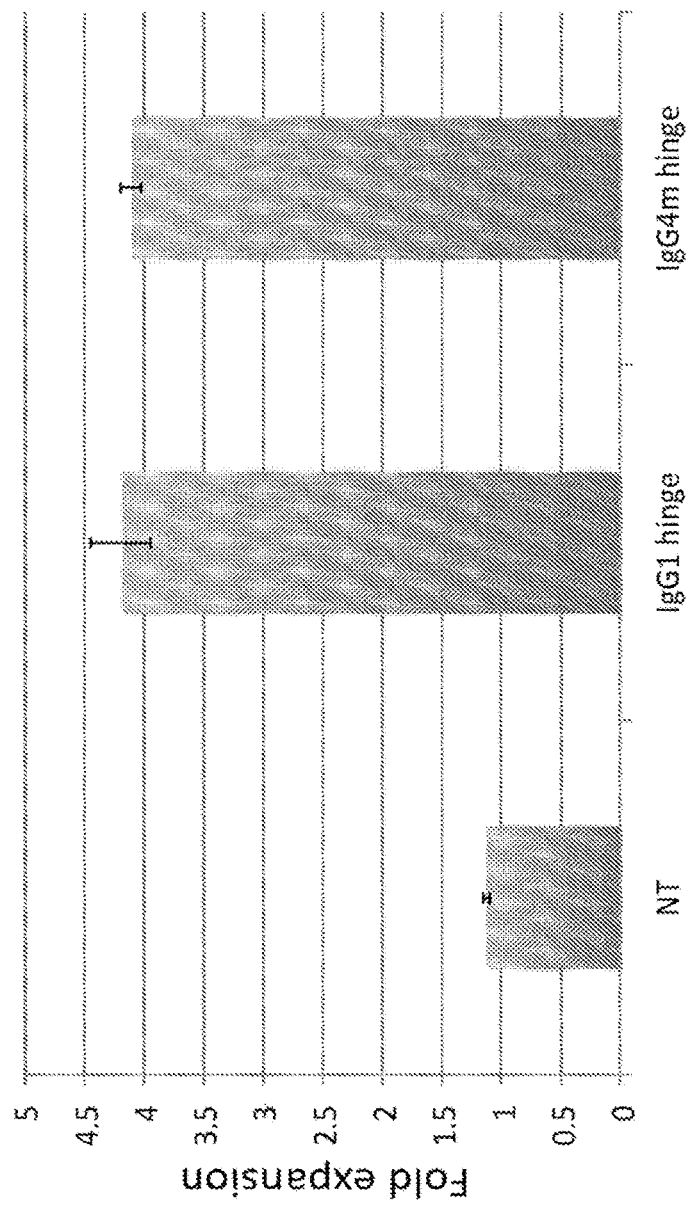
FIG. 7 shows data validating XTL-19-IgG4m CAR.

An initial in vivo pilot showed no efficacy with the IgG1 hinge upon intravenous dosing, and without being bound by theory the cells may have been trapped and eliminated in the lungs, similar to previous reports in the literature. Therefore, the inventors then replaced the IgG1 hinge of the XTL-19 CAR with a mutated IgG4 Fc region (based on published mutations in Hudecek et al. (2015)) to allow for persistence in vivo via absence of Fc receptor binding; this new CAR construct was designated XTL19-IgG4m. XTL19-IgG4m was validated by demonstration of in vitro expansion of XTL19-IgG4m CAR-expressing T cells upon co-culture with HepG2.2.15 cells, consistent with expansion of T cells expressing the parent XTL-19 CAR (FIG. 7).

The following shows one example of a humanized pilot for CAR T cell therapy using CARs that have been modified to avoid Fc receptor binding:

Humanized mice as described in Example 1 were obtained from the same hepatocyte donor (chimeric human liver mice are generated by transplanting hepatocytes from cadavers into the mice). On Day 30, 200 µL of pooled serum from mouse injected i.p. with Genotype D hepatitis B virus was administered to the humanized mice, and viral incubation was allowed to proceed. On Day 0, the first blood draw was obtained from the mice. At Day 37, 10 million CAR transduced (XTL19-G4m-CD28-Zeta) or 10 million normal T cells, from the same donor, were administered to the mice, with blood draws at Day 4, Day 7, and every 7 days after that (FIG. 8)

Figure 8:
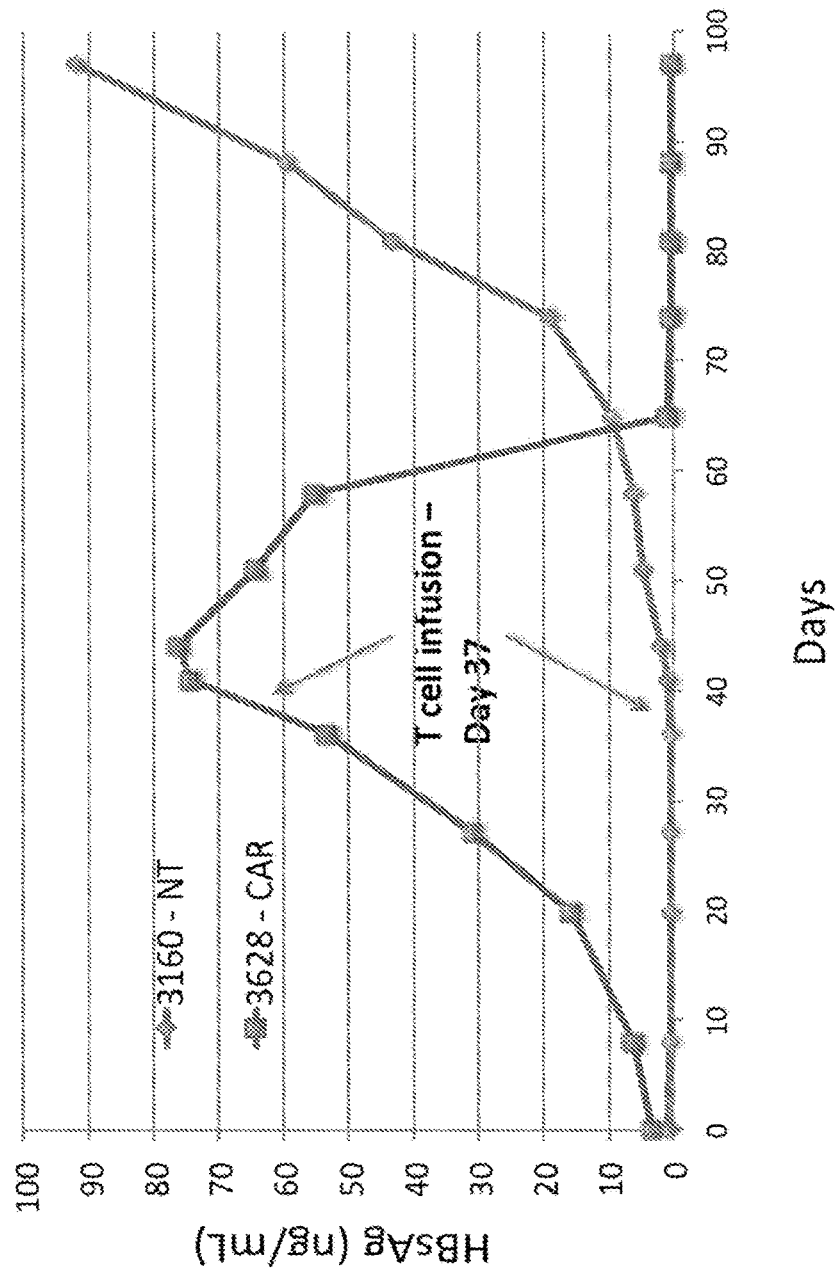
FIG. 8 demonstrates CAR T cell therapy using XTL19-G4m-28-zeta CAR in a humanized pilot. CAR refers to HBV CAR T cells, and NT refers to Non-transduced Normal T cells. Readout is serum HBsAg levels during a growing viral infection in lowly repopulated humanized mice.
Figure 9:
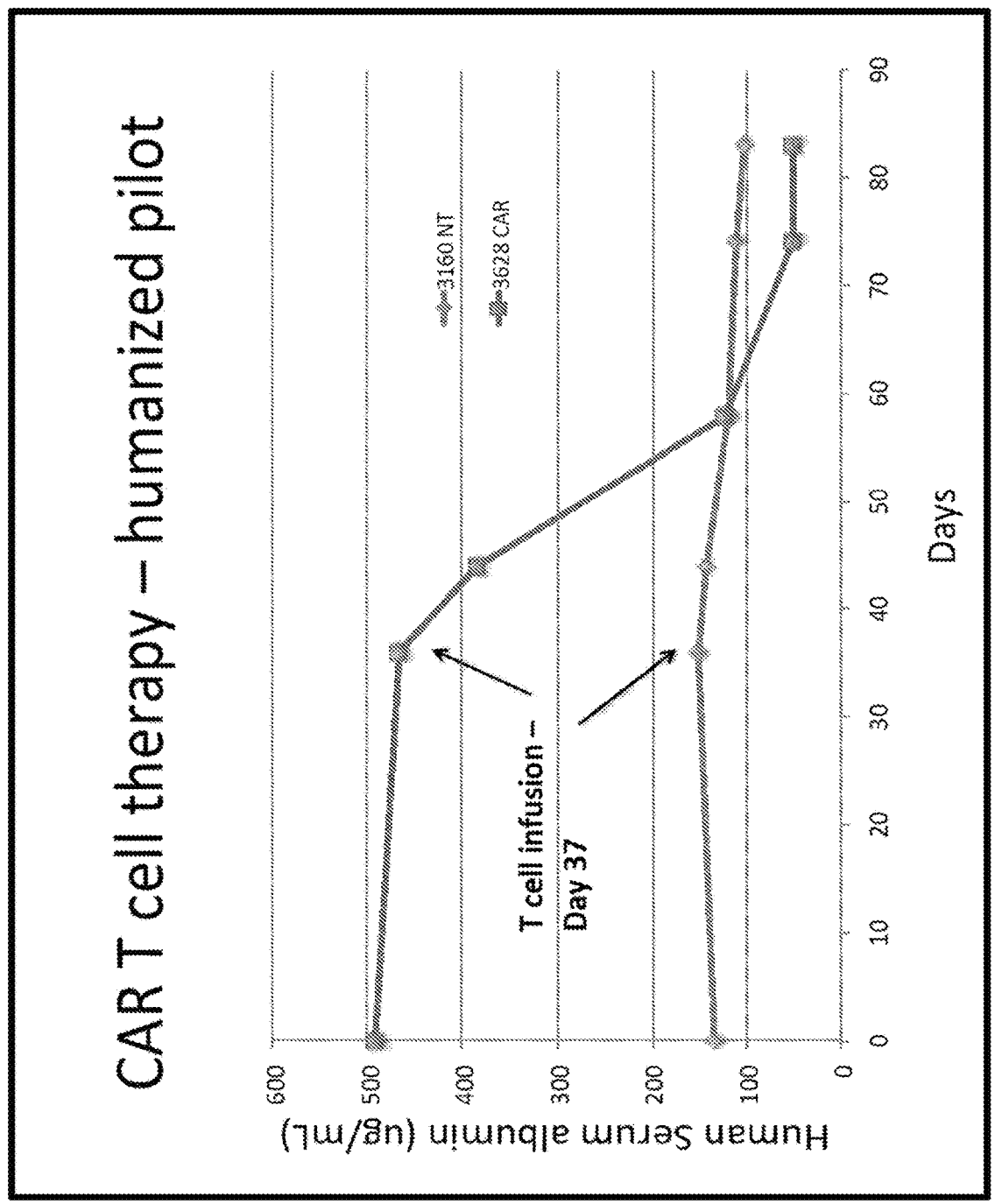
FIG. 9 demonstrates CAR T cell therapy using XTL19-G4m-28-zeta CAR in a humanized pilot. CAR refers to HBV CAR T cells, and NT refers to non-transduced Normal T cells.

In CAR T cells, HBsAg is a secreted viral protein that is produced in high levels by the virus and serves as a marker for viral replication and persistence (FIG. 8). Human serum albumin (FIG. 9) is a secreted protein that is a marker for human hepatocyte levels in the mouse. Only human hepatocytes are infected with HBV.

The elimination of HBsAg levels in XTL19-G4m-CAR-treated mice was observed, which suggests elimination of HBV-infected cells and therefore HBV, while the HBsAg continued increasing uninhibited in mice administered unmodified T cells. CAR T cells appear to be mediating a cytotoxic effect and can home to the liver and find and eliminate infected cells amongst a majority uninfected liver. In addition, the in vivo data matches efficacy observed in cell culture. The results provide the first demonstration of in vivo improvement of HBV in its natural setting (human cells). One can also utilize cytokines alone to see if they can mediate clearance of viruses without any cytolytic mechanisms in the host cells, beyond their bystander activities toward other immune cells. That is, cytokines can be useful mediators in the clearance of HBV virus, and in specific embodiments engineering of the CAR-T cell to maximize secretion of cytokines to clear virus safely that does not also damage the liver is useful. The cytokines can serve to activate other immune cells, which in particular aspects reinvigorate a dormant host immune response against HBV.

EXAMPLE 3

HBSAG-Redirected T Cells have Potent Antiviral Activity in HBV-Infected Human Liver Chimeric Mice Because HBV cannot presently be cured, it was considered whether CAR therapy could result in permanent reductions in HBV levels. This was examined by testing HBsAg-redirected CAR-T cells to treat HBV-infected humanized mice.

A CAR was developed against HBsAg using two human antibodies, XTL-17 and XTL-19 that are specific toward a variety of HBsAg serotypes. CARs were prepared with single chain variable fragments (scFvs) from these antibodies with a human IgG1 Fc domain as the hinge domain and CD28 and CD3 zeta endodomains. The activation of CAR-T cells was verified when incubated with HepG2.2.15 cells positive for HBV. XTL-19 CAR-T cells released IFN-γ, TNF-α, and IL-2 at 24 hours, expanded in number, and after a week of co-culture, HepG2.2.15 were completely eliminated (FIG. 12). The XTL-17 CART cells, in contrast, did not show a similar release of IFN-γ, TNF-α, or IL-2 at 24 hours. The fact that the XTL-17 CAR, which also targeted HBsAg, did not have the same activity as that of XLT-19 CAR T-cells indicated the validation of HBV CARs is empirical and individual CARs may possess unique properties. XTL-19 CAR-T specificity for HBsAg was confirmed by lack of killing, expansion, and cytokine release in presence of HepG2 cells (FIG. 13). The CARs recognize soluble HBsAg in addition to cell bound antigen (FIG. 14). XTL-19 exhibited the most activity and was utilized in further studies.

Given that persistence was limited in a previous CAR-T study, it was considered that this might be because of the IgG1 hinge binding to mouse FcR-bearing cells, causing CAR-T elimination. It was considered that a modified hinge region would not interact with Fc receptors, allowing for increased CAR-T cell persistence. A hinge region with a deleted CH2 domain, essential for Fc receptor binding, exhibited no proliferation in vitro when incubated with HepG2.2.15 cells suggesting that a longer hinge geometry is useful for reaching the HBsAg epitopes adequately on the hepatocyte surface in order to trigger clustering and activation (FIG. 14). Mimicking the efficacious geometry of the original IgG1 Fc hinge domain, the inventors utilized a hinge region based on the IgG4 Fc domain with mutations in the hinge and CH2 domains that abrogate receptor binding and proved to maintain CAR efficacy in mouse models. Upon testing in vitro, the modified cells replicated the original functionality in proliferation assays (FIG. 14).

Figures 15A, 15B, 15C, 15D, 15E, 15F:
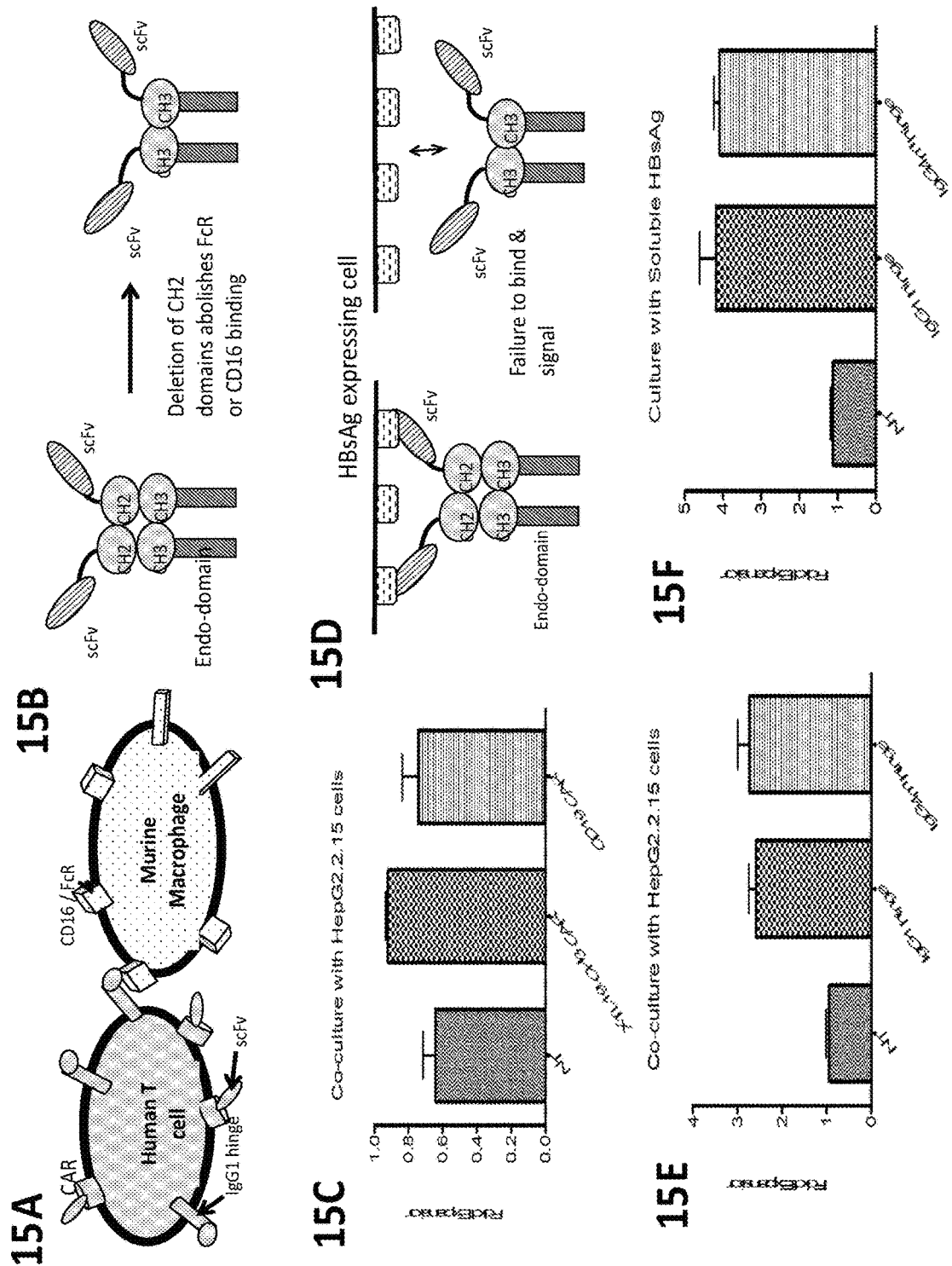
FIGS. 15A-15F Validating the optimal chimeric antigen receptor geometry in order to efficiently bind to HBV antigen and activate T cells. (15A) CAR-T cells containing the IgG1 hinge region between the scFv and the transmembrane domain can bind to the Fc receptor displayed on murine macrophages when conducting in vivo experiments, thereby limiting CAR-T persistence. (15B) The CH2 domain contains critical residues for Fc receptor binding. Elimination of the CH2 domain in the CAR can completely abrogate Fc receptor, forming an XTL19-CH3 CAR. (15C) CAR-T cells were generated with control off-target CD19 CAR and XTL19-CH3 CAR. Along with non-transduced T cells, they were co-cultured with HepG2.2.15 cells for one week, after which the cells were collected and counted. None of the conditions exhibited any T cell expansion, and XTL19-CH3 CAR also did not kill HepG2.2.15 cells. (15D) The lack of functionality of the shortened XTL19-CH3 CAR is likely due to the inability to adequately bind HBsAg epitopes at the proximal cell surface, and/or produce sufficient clustering of CAR molecules for T cell activation. (15E) A new CAR was then generated containing at the hinge the IgG4 Fc domain with several mutations to abrogate Fc receptor binding, with all the other sequences remaining the same. The CAR was then compared to the original IgG1 hinge containing construct to verify efficacy, with a non-transduced T cell group included as a control. When incubated in co-culture with HepG2.2.15 cells, both IgG1 hinge and IgG4 mutant (IgG4m) proliferated to similar extents (15F). The same groups were also incubated with supernatant from HepG2.2.15 cells in order to verify recognition of soluble HBsAg and requisite expansion of T cells. In this assay as well, both IgG4m and IgG1 containing CARs resulted in similar proliferation of CAR-T cells.

Given that persistence was limited in a previous CAR-T study, it was considered that this might be because of the IgG1 hinge binding to mouse FcR-bearing cells, causing CAR-T elimination. The hinge region was modified such that it would not interact with Fc receptors, allowing for increased CAR-T cell persistence. T cells expressing a CAR comprising a hinge region with a deleted CH2 domain, essential for Fc receptor binding, exhibited no proliferation in vitro when incubated with HepG2.2.15 cells suggesting that a longer hinge geometry is useful for reaching the HBsAg epitopes adequately on the hepatocyte surface in order to trigger clustering and activation (FIG. 15). Mimicking the efficacious geometry of the original IgG1 Fc hinge domain, a hinge region was utilized that was based on the IgG4 Fc domain with mutations in the hinge and CH2 domains that abrogate Fc receptor binding. The hinge maintained CAR efficacy in mouse models. Upon testing in vitro, the modified cells replicated the original functionality in proliferation assays (FIG. 15).

Figures 16A, 16B, 16C, 16D, 16E:
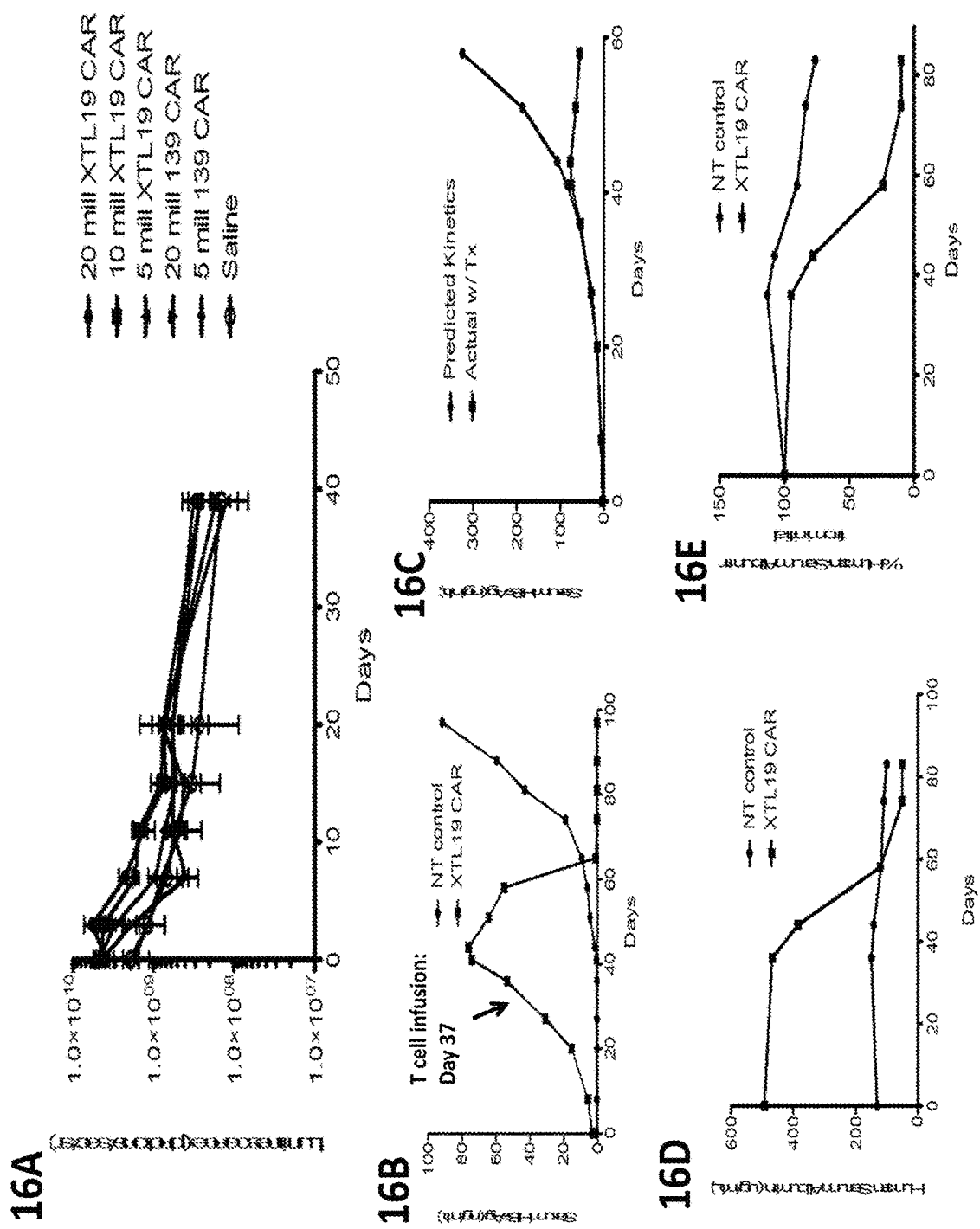
FIGS. 16A-16E show verification of activity of CAR T cells in vivo. (16A) NOD SCID−/− gamma−/− (NSG) male mice were hydrodynamically injected with 20 ug of HBV1.3-luciferase plasmid, wherein the luciferase is driven by the second core promoter in the HBV overlength construct. 3 days after plasmid injection, different doses of XTL19 CAR and 139 CAR T cells were prepared and injected i.p. into the mice (n=3 per condition), along with one mouse receiving saline control. Luminescence was monitored by IVIS imagining after luciferin injection. No difference between difference between all groups of mice was observed. (16B) Humanized mice with low humanization were infected with HBV. During the growth phase of infection. mice were injected with 10 million XTL19-G4m CAR T cells or non-transduced T cells at day 37 post viral injection. HBsAg levels demonstrated clearance of CAR treated mice and continued growth of control treated mice. (16C) An exponential fit comparison to the viral kinetics and comparison to the actual HBsAg results was modeled to demonstrate the comparative efficacy. (16D) Human serum albumin (HSA) levels were monitored, demonstrating a sharp reduction post XTL19 CAR-T treatment versus no change in non-transduced T cell treated mice. (16E) Serum albumin levels normalized to initial levels reveal an approximate 90% reduction in HSA levels versus a slight decline in non-transduced treated mice.
Figure 17:
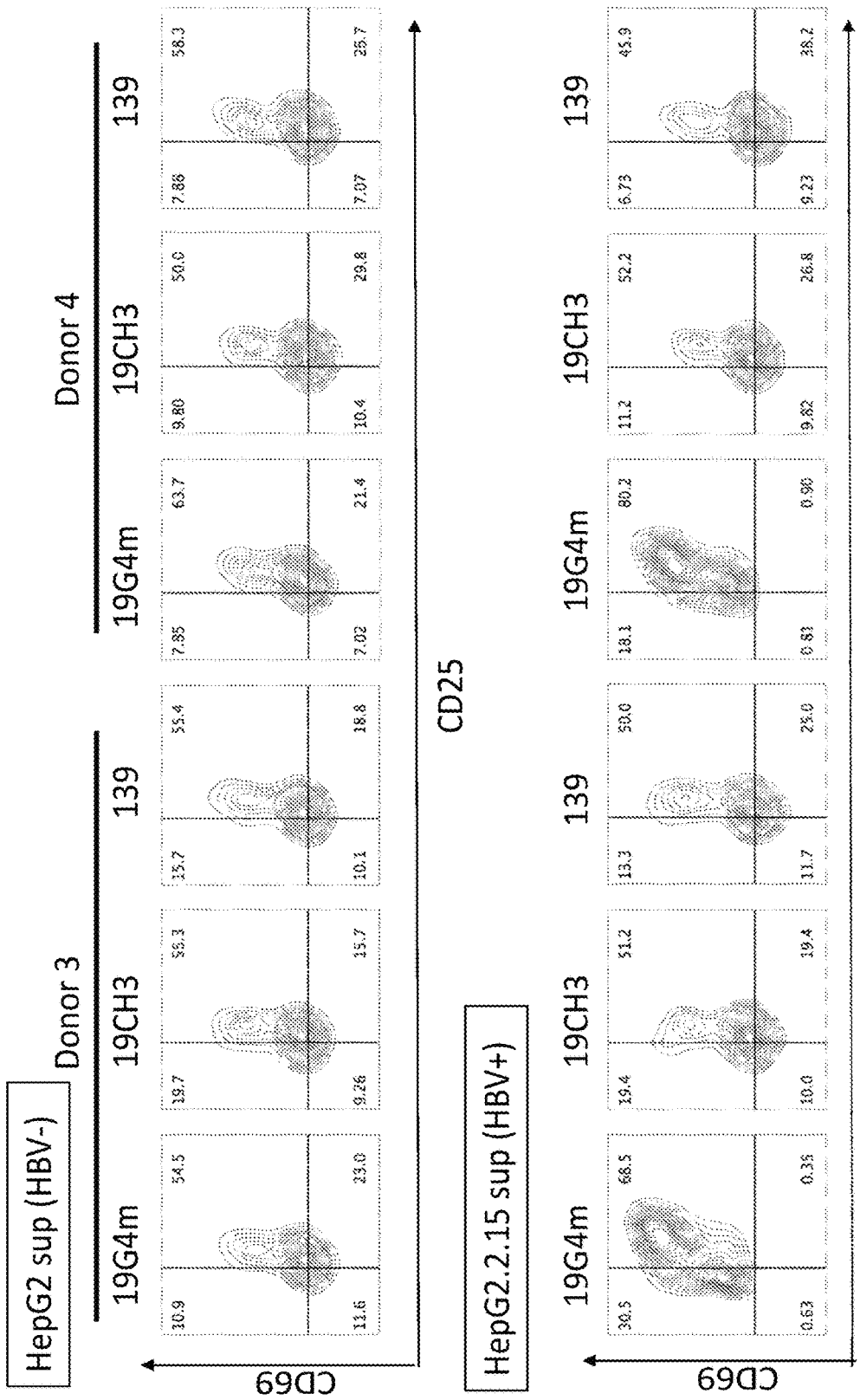
FIG. 17 shows that CAR-T cells with the long hinge (G4m) and HBsAg specificity (19) are express T cell activation markers (CD69 and CD25) in the presence of soluble HBsAg particles, whereas CAR-T cells (13) that are untargeted or have the short hinge (CH3) do not show signs of T cell activation. Specifically, culture of CAR-T cells (2 million) with supernatant (1 million) target reveals XTL19-G4m-28-zeta CAR is only activated by HBV antigen, the shorter hinge or linker with CH3 does not have enough length to activate the CAR-T, and the 139 against and irrelevant antigen is not activated at all as measured 24 hours after setup.

The activity of CAR T cells in vivo was verified. The inventors sought an initial test in an episomal HBV model system and utilized hydrodynamic tail vein injection of plasmids containing the HBV genome and a reporter luciferase driven the HBV core promoter. Any T cell activity against hepatocytes should cause decreases in luminescence signal. However, there was no detectable difference in luminescence between XTL-19 and control 139 CAR-T cells (FIG. 16), suggesting that differences between human and murine immunity is limiting. The therapy was tested in a humanized mouse model of HBV infection, which would be fully compatible and most closely approximate the efficacy of the therapy in human individuals. A pilot experiment treating mice with low-level spreading infection revealed the ability of CAR-T cells to completely clear HBsAg from serum, with an accompanying decline in human serum albumin (HSA), suggesting death of infected cells (FIG. 16).

A larger cohort of mice was tested with high baseline levels of infection. Obtaining 7 humanized mice with high human hepatocyte repopulation, the inventors injected $10^6$ genomes of HBV into the intraperitoneal cavity allowing infection to spread over 1-2 months and high titers to be reached (FIG. 10C). XTL19 CAR and 139 CAR T cells were generated (FIG. 10A) and were infused intraperitoneally into the HBV-infected humanized mice, respectively. 139 scFv has reactivity toward EGFRvIII antigen, which is not expressed in mice, and served as negative control. There was a 1-3 log decrease in HBV DNA levels after 3-4 weeks in treated mice, which rebounded to a stable 1-log drop after 1 month (FIG. 10F). HBsAg levels also decreased with different kinetics, slowly declining to a peak of 2-3 logs over 3 months (FIG. 10D). Mice were observed with lower initial HBsAg levels that had faster responses, which may be because of the inhibitory levels of soluble HBsAg affecting T cell homing or target cell binding. A second CAR-T cell infusion using frozen cells at Day 59 lacked the same antiviral potency as the fresh cells injected from same batch. The 139 CAR-T treated mice did not have declines in DNA or HBsAg by comparison (FIGS. 10E, 10G). Over the initial first month of peak CAR-T activity, there were no differences between XTL19- and 139 treated mice human serum albumin levels, suggesting a non-cytopathic role in initial clearance (FIG. 11E). Stable weight and persistent HSA months after T cell infusions suggest a lack of mouse or human directed GVHD, respectively (FIG. 11F).

Figures 11A, 11B:
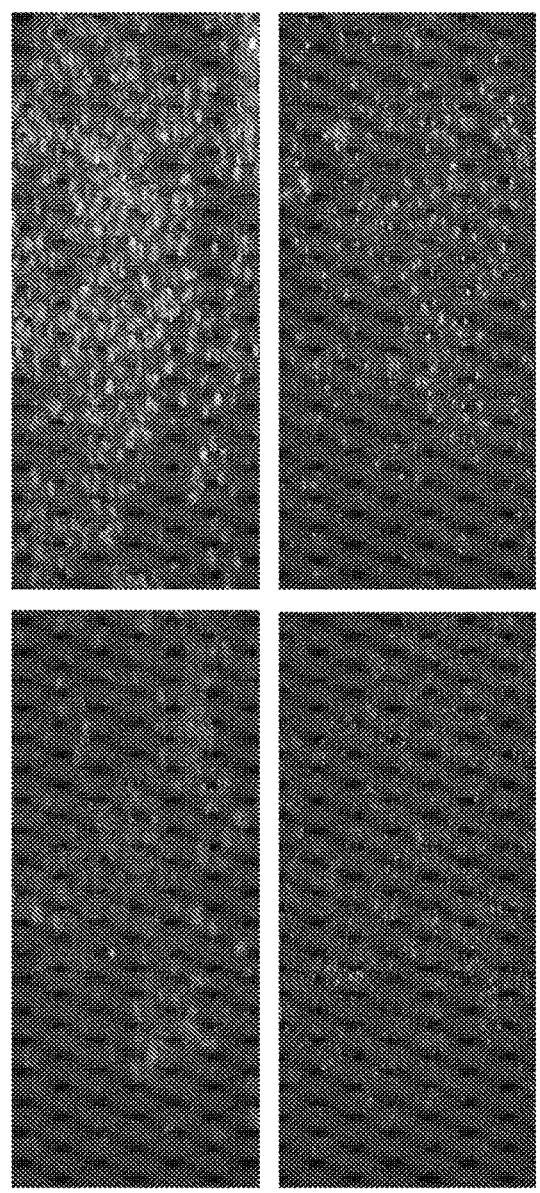

After a second CAR-T infusion, the inventors harvested two mice at day 10 post CAR-T infusion in the treatment and control groups (FIG. 11A), observing abundant HBV-free hepatocytes in the XTL19 group compared to almost every cell being infected in the 139 control, as assessed by HBV core antigen and human albumin or nuclear co-staining (FIG. 11B). The significant decrease suggests CAR-T cells may purge HBV from cells non-cytopathically (degraded by intracellular enzymes, which can be triggered by cytokines such as interferon gamma and TNF-alpha), and in the case of human nuclear stain, CAR-T cells were recruited to infected tissue causing further decrease in ratio (FIGS. 11C-11D).

Thus, CAR-T cells redirected to HBsAg are effective in clearing HBV in authentic human liver tissue, as evidenced by their ability to decrease HBsAg levels. Complete elimination is likely limited by lack of CAR-T cell persistence, similar to cancer studies, leading to viral rebound. In specific embodiments, combination treatment with reverse transcriptase (RT) inhibitors is useful in preventing this.

Culture of CAR-T cells (2 million) with supernatant and HBV+ or HBV− cells (1 million cells) reveals XTL-19-IgG4m CAR-expressing T cells are only activated by HBV antigen. The supernatant comprises both virions containing DNA that are infectious to new cells as well as many empty, smaller subviral particles that contain an antigen array that can be targeted for CAR T cell recognition and activation, so that they can serve to activate T cells. The shorter hinge or linker with CH3 does not have enough length to activate the CAR-T, in this particular example, and the 139 scFv against an irrelevant antigen is not activated at all. CD25 and CD69 are signatures of T cells that are activated, showing in this case that the activation of the CAR-T cells only occurs in the presence of antigen, lending more evidence that this is a specific process to HBsAg recognition by the CAR-T cells.

Figure 18:
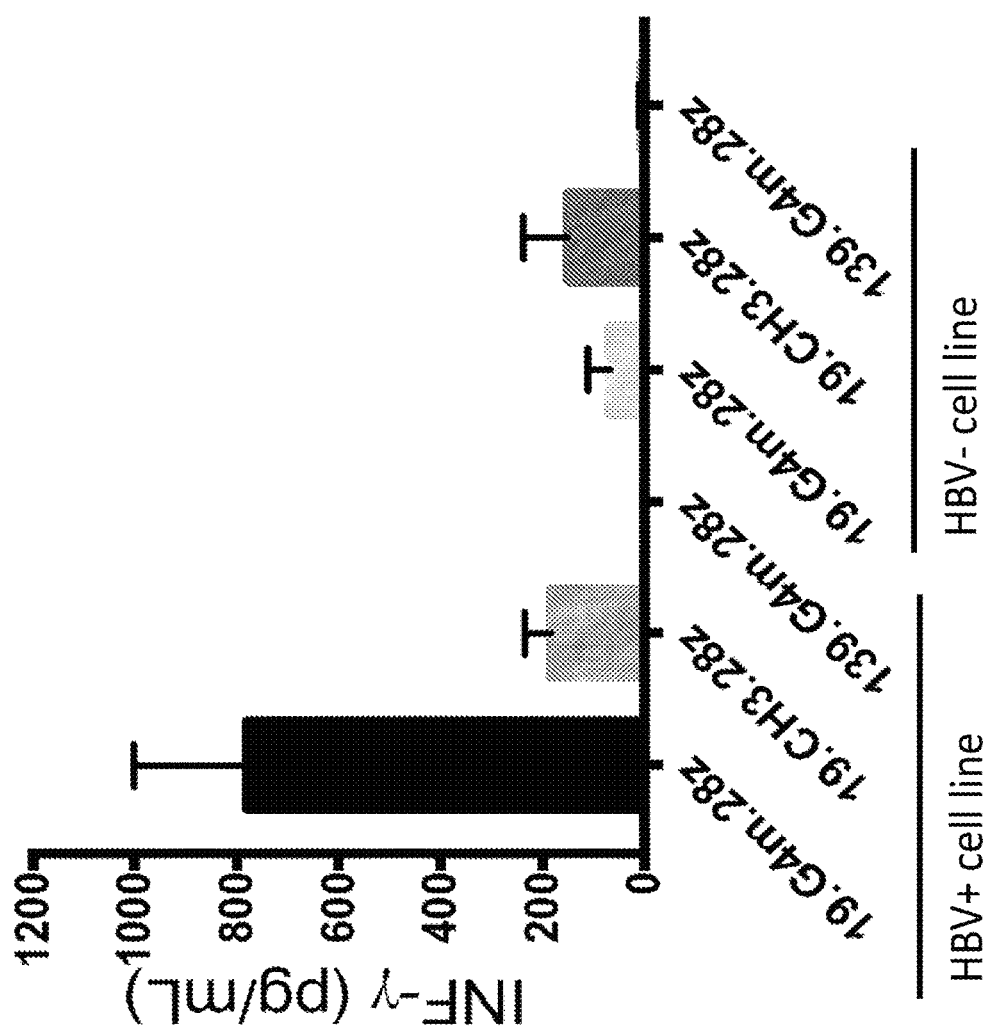
FIG. 18 shows that CAR-T cells recognize HBV positive cells, release cytokines and that a shorter linker is not efficacious in at least some cases. Culture of CAR-T cells (2 million) with supernatant (1 million) target reveals XTL19-G4m-28-zeta CAR is only activated by HBV antigen causing cytokine release, the shorter hinge or linker with CH3 does not have enough length to activate the CAR-T, and the 139 against and irrelevant antigen is not activated at all.
Figure 19:
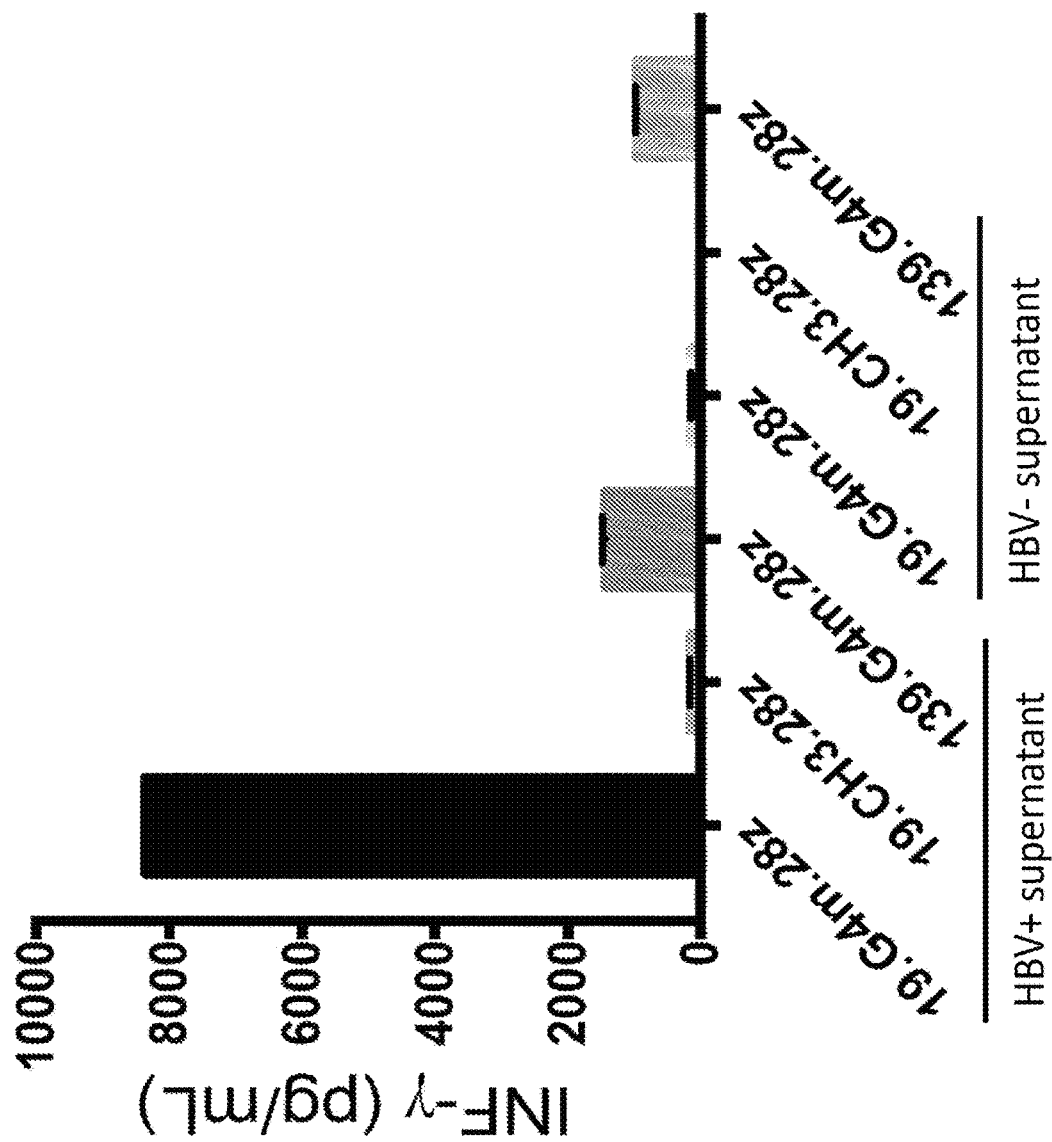
FIG. 19 demonstrates that the tested CAR-T cells recognize HBV particles and release cytokines. CAR-T cells (1 million cells) from two donors were cultured with 75 ng/mL HBsAg and supernatant collected 24 hours after setup. The shorter hinge or linker with just the CH3 domain did not allow the CAR to connect to the HBsAg particle surface and become activated.

FIG. 18 demonstrates that culture of CAR-T cells (2 million) with supernatant from HBV+ or HBV− cell lines reveals that XTL19-G4m-28-zeta CAR is only activated by HBV antigen causing cytokine release, the shorter hinge or linker with CH3 does not have enough length to activate the CAR-T, in this particular example, and the 139 against an irrelevant antigen is not activated at all. That is, the length of the hinge is a factor in CAR-T cell activation. In at least specific cases, using the same single chain antibody binding fragment (scFv 19), a hinge length that is shorter (CH3) does not result in CAR-T activation, while the hinge length that is longer is able to efficiently reach the HBV epitopes and trigger some activation FIG. 19 shows that CAR-T cells (1 million cells) from two donors were cultured with 75 ng/mL HBsAg and supernatant collected 24 hours after setup. The shorter hinge or linker with just the CH3 domain did not allow the CAR to connect to the HBsAg particle surface and become activated, in this particular example, as depicted by a lack of INF-gamma release into the supernatant.

Figures 20A, 20B:
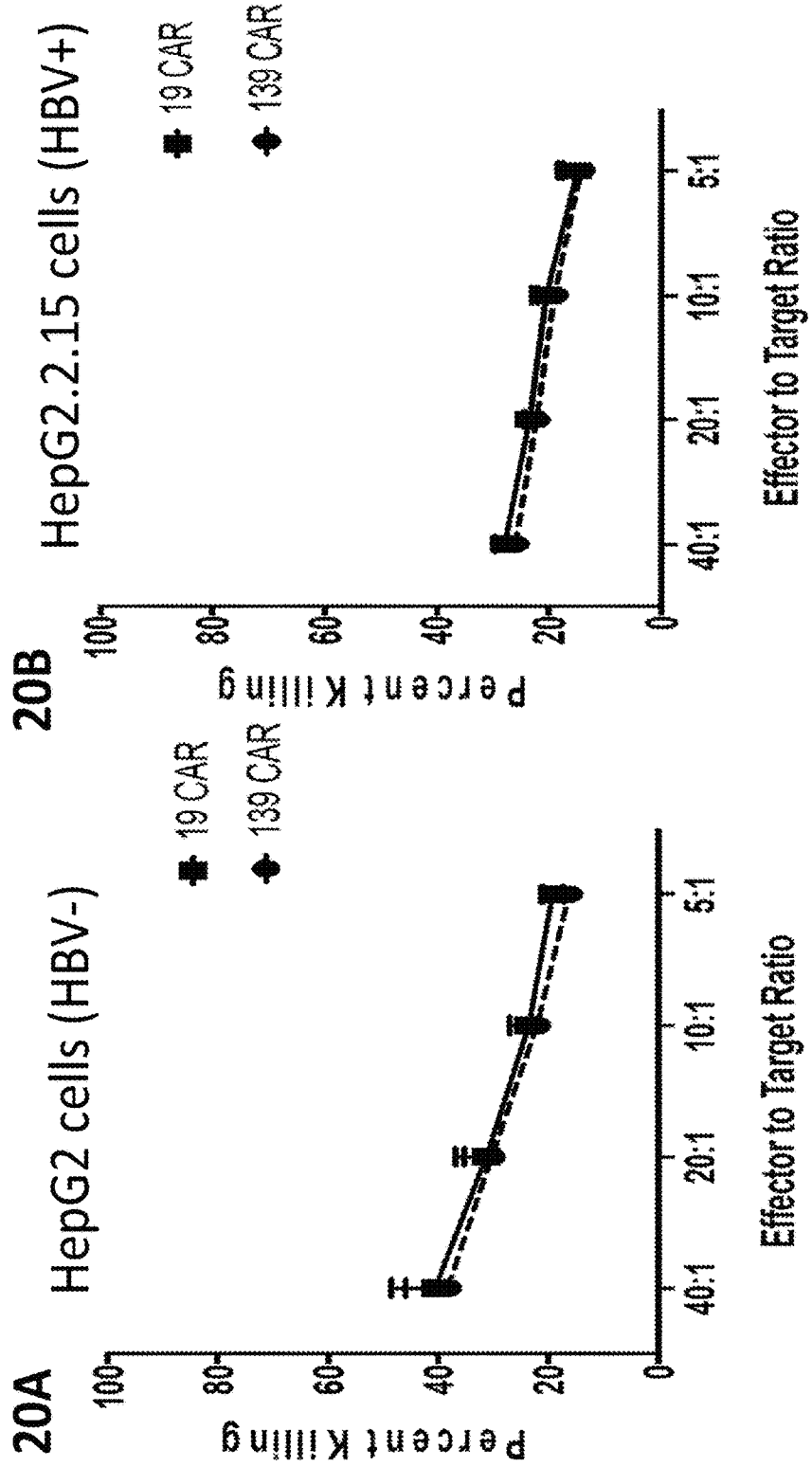
FIGS. 20A and 20B demonstrate that in a short-term 5 hour cytotoxicity assay (chromium release), the chimeric antigen receptor 19-G4m-28-zeta has no appreciable cytotoxicity compared to control CAR 139-G4m-28-zeta either on the on-target cell line HBV+ HepG2.2.15 cells (20B), or the off-target cell line HBV− HepG2 cells (20A). These results demonstrate that while the CAR efficiently releases cytokines during this period, the product might be safe from destroying hepatocytes making it unique among CAR molecules characterized so far.

FIG. 20 demonstrates that 5 hour culture of CAR-T cells (2 million) with supernatant (1 million) targets cells either HBV+ (HepG2.2.15) or HBV− (HepG2) cell lines indicates in a chromium release assay where target cell death is measure by the release of radioactive Cr51 from the cells, the XTL-19 CAR against HBsAg was not cytotoxic and lacked statistical difference between off-target 139 CAR, demonstrating this CAR is unique in not killing cells during the short-term culture and activation period. The XTL19 CAR thus represents a novel and unexpected phenotype versus the previous published HBV CAR molecule that was significantly more cytotoxic, as well as many different CARs being used to treat cancer.

EXAMPLE 4

HBSAG-Redirected T Cells Exhibit Antiviral Activity in HBV-Infected Human Liver Chimeric Mice Hepatitis B virus (HBV) is a global pandemic chronically infecting 300 million people across the world today (Shepard, et al., 2006). In these chronic patients, HBV causes a lifelong infection that can lead to liver cirrhosis or cancer in 25% of patients (Perz, et al., 2006). HBV therapies currently remain limited to reverse transcriptase inhibitors (RTIs) and interferon (IFN)-α. RTIs only suppress HBV-DNA levels without significantly affecting the transcriptional template, covalently closed circular DNA (cccDNA) (Liaw, et al., 2009) while IFN-α causes significant side effects with little long-term therapeutic benefit (Ning, et al., 2014). Thus, new anti-HBV therapies are urgently needed in order to cure the virus.

During the HBV-specific immune response in acutely resolving patients, infiltrating T-cells rapidly purge the liver of HBV (Wieland, et al., 2004; Thimme, et al., 2003). In chronic HBV patients, however, HBV-specific T-cells are present in only low frequency and/or are anergic (Boni, et al., 2007). CD8-positive T-cells have been shown to be crucial in resolution of acute HBV infection (Thimme, et al., 2003). They are able to clear HBV in both cytolytic and noncytolytic effector functions (Hoh, et al., 2015). The cytokines, IFN-γ and TNF-α, released by T-cells are important in driving noncytolytic suppression of virus (Guidotti, et al., 1996; Phillips, et al., 2010). Both IFN-γ and TNF-α can induce degradation of intracellular cccDNA (Xia, et al., 2016) explaining part of this mechanism.

The adoptive transfer of T-cells genetically engineered to target hepatitis B surface antigen (HBsAg) with chimeric antigen receptors (HBsAg-CAR T-cells) is an attractive strategy to reconstitute HBV-specific T-cell immunity. Indeed, HBsAg-CAR T-cells have been shown to eliminate cccDNA from HBV-infected primary hepatocytes in vitro (Bohne, et al., 2008), and had transient anti-HBV activity in a transgenic HBV mouse model (Krebs, et al., 2013). Despite these promising results, it remains an open question whether HBsAg-CAR T-cells can induce a reduction of HBV levels in an animal model with authentic infection harboring episomal HBV cccDNA. The present examples addresses this question by evaluating human HBsAg-CAR T-cells in HBV-infected human liver chimeric mice (Bissig, et al., 2010).

Generation of a Novel CAR Targeting HBsAg

Figures 21A, 21B:
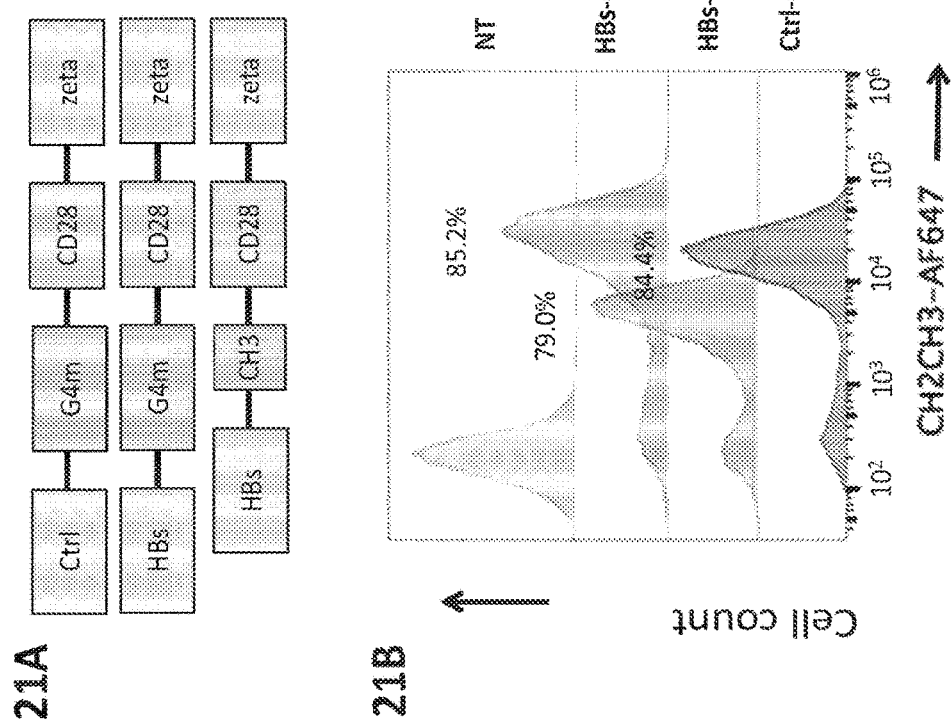
FIGS. 21A-21B show generation of HBsAg-CAR T-cells. (21A) Scheme of HBs-G4m, HBs-CH3, and Ctrl-G4m CAR constructs. (21B) Representative FACS analysis of HBs-G4m-CAR (orange), HBs-CH3-CAR (blue), and Ctrl-G4m-CAR T-cells (red) confirming CAR expression (gray: non-transduced T-cells, NT).

Two HBsAg-CARs were generated with a CD28.ζ signaling domain and a single chain variable fragment (scFv) derived from the human monoclonal antibody (mAb) 19.79.5, which recognizes HBsAg from different serotypes (Eren, et al., 2000), and has undergone successful Phase 1 testing (Galun, et al., 2002). Because the length of the spacer region of CARs is useful for their function (Hudecek, et al., 2015), long and intermediate spacers were compared. The IgG4 Fc domain with mutated Fc receptor binding sites (HBs-G4m-CAR) served a long (Hudecek, et al., 2015) and the CH3 domain of IgG1 as an intermediate spacer (HBs-CH3-CAR; FIG. 1a). As a control, a G4m-CAR was constructed with an scFv specific for an irrelevant antigen (EGFRvIII, Morgan, et al., 2012); Ctrl-G4m-CAR; FIG. 21A). CAR T-cells were generated by retroviral transduction, and the median transduction efficiency was 79.0% (range 60.5-89.9) as judged by FACS analysis with no significant differences between CAR constructs (FIG. 21B).

HBs-G4m-CAR T-Cells Recognize HBV-Positive Cells In Vitro

Figures 22A, 22B, 22C, 22D, 22E:
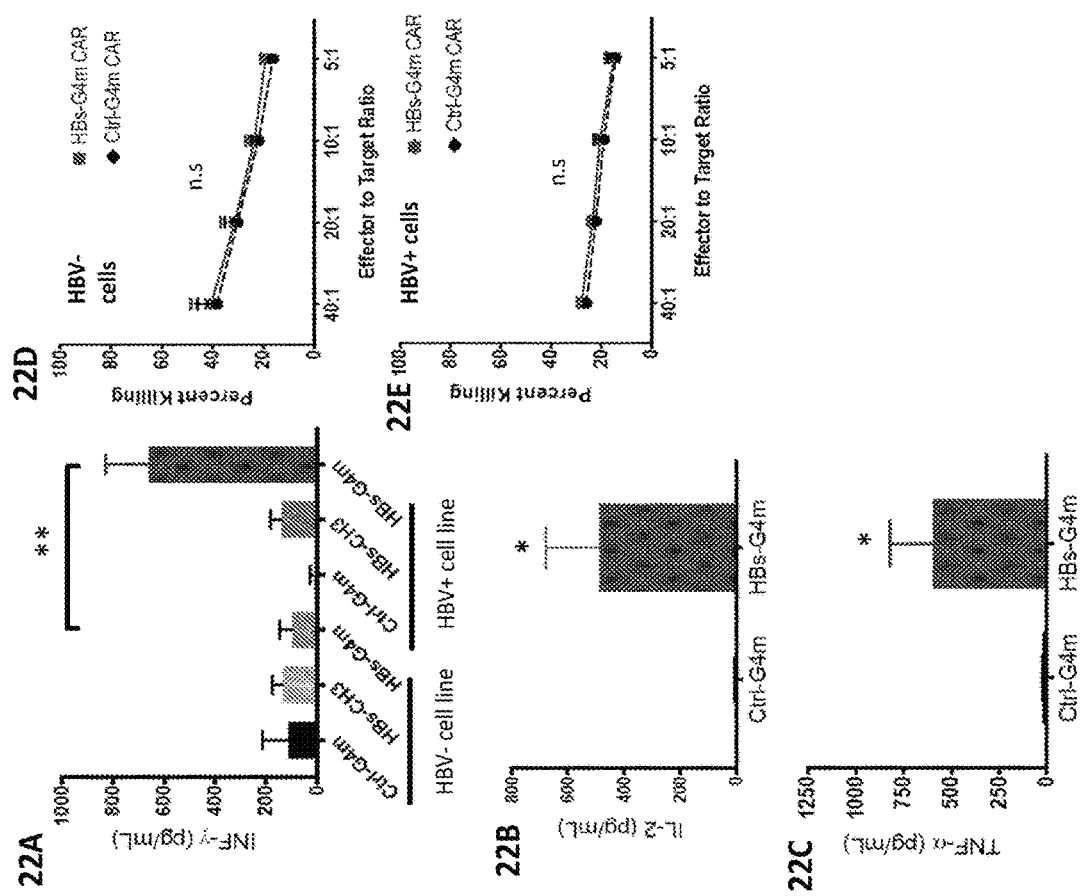
FIG. 22A-22E show functional characterization of HBsAg-CAR T-cells. CAR-T cells were co-cultured with HBV+ or HBV− cell lines. Cytokine production, (22A) IFN-γ, (22B) IL-2, and (22C) TNF-α, was measured by ELISA after 24 hours (for IFN-γ: **$p<0.005$, n=4; for IL-2, and TNF-α: *$p<0.05$, n=3). CAR-T cells were tested in a 5-hour chromium release assay against (22D) HBV− or (22E) HBV+ cell lines (n.s.: not significant, n=3). Error bars represent S.E.M. and significance is determined by unpaired, one-tailed t-tests.

To determine which HBs-CAR recognized HBV-positive cells, 24-hour co-culture assays were performed with HepG2 (HBV negative) and HepG2.2.15 (HBV positive) cell lines, washing the cells first before adding CAR-T cells. Only HBs-G4m-CAR T-cells produced significant amounts of IFN-γ in the presence of HepG2.2.15 in contrast to HBs-CH3-CAR and Ctrl-G4m-CAR T-cells (FIG. 22A). HepG2 induced only background IFN-γ production confirming specificity. These results demonstrate that a long spacer is needed for CARs with a mAb 19.79.5-derived HBsAg binding domain. In addition to IFN-γ HBs-G4m-CAR T-cells also produced IL-2 (FIG. 22B) and TNF-α (FIG. 22C) in the presence of HepG2.2.15 in contrast to Ctrl-G4m-CAR T-cells. Having established that HBs-G4m-CAR T-cells recognize HepG2.2.15 in an HBsAg-restricted fashion, standard cytotoxicity assays were performed with HepG2 and HepG2.2.15 (FIG. 22D,E). Only background killing of HepG2.2.15 by HBs-G4m-CAR T-cells was observed in this 5-hour cytotoxicity assay.

HBs-G4m-CAR T-Cells Recognize HBsAg Particles In Vitro

Figures 23A, 23B, 23C:
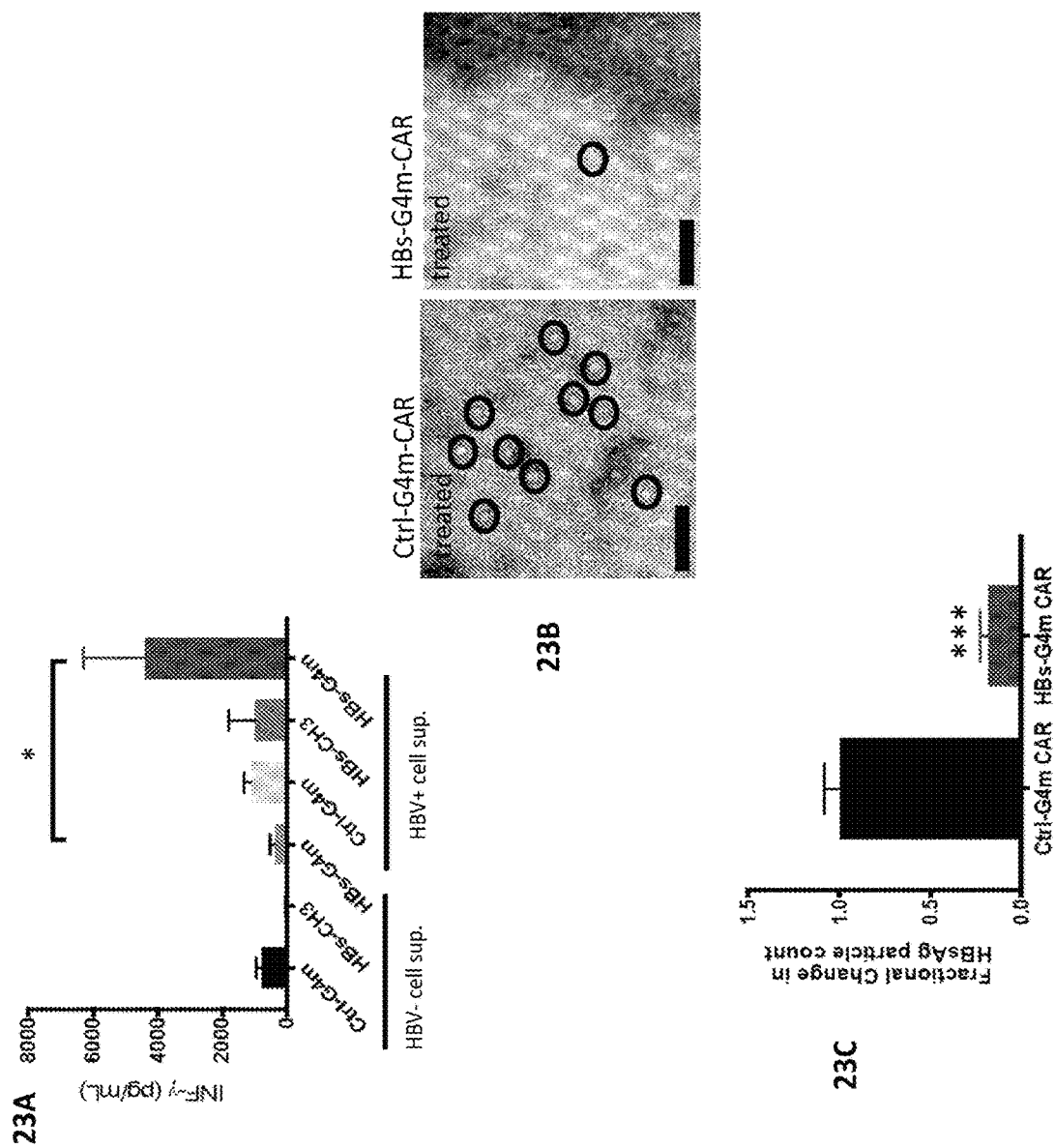
FIG. 23A-23C demonstrate that HBs-G4m-CAR T-cells recognize HBsAg particles secreted by HBV positive cell lines. (23A) CAR T-cells were cultured with supernatants from HBV+ or HBV− cell lines and IFN-γ was measured by ELISA after 24 hours (*$p<0.05$, n=3 donors). Error bars represent S.E.M. and significance is determined by unpaired, one-tailed t-tests. (23B) HBs-G4m-CAR and Ctrl-G4m-CAR T-cells were cultured with media from HBV+ cells (HepG2.2.15) containing HBsAg particles and virions (in red circles) and incubated for 24 hours, after which supernatant was collected. HBsAg subviral particles were visualized by electron microscopy without any purification in order to assess relative concentration of HBsAg particles and virions across visual fields (scale bar=200 nm). (23C) EM fields were imaged and the amount of HBsAg subviral particles and virions (judged by their spherical size 25-45 nm) was compared among HBs-G4m-CAR and Ctrl-G4m-CAR conditions (***$p<0.0001$, n=8 fields, 2 donors).
Figure 26:
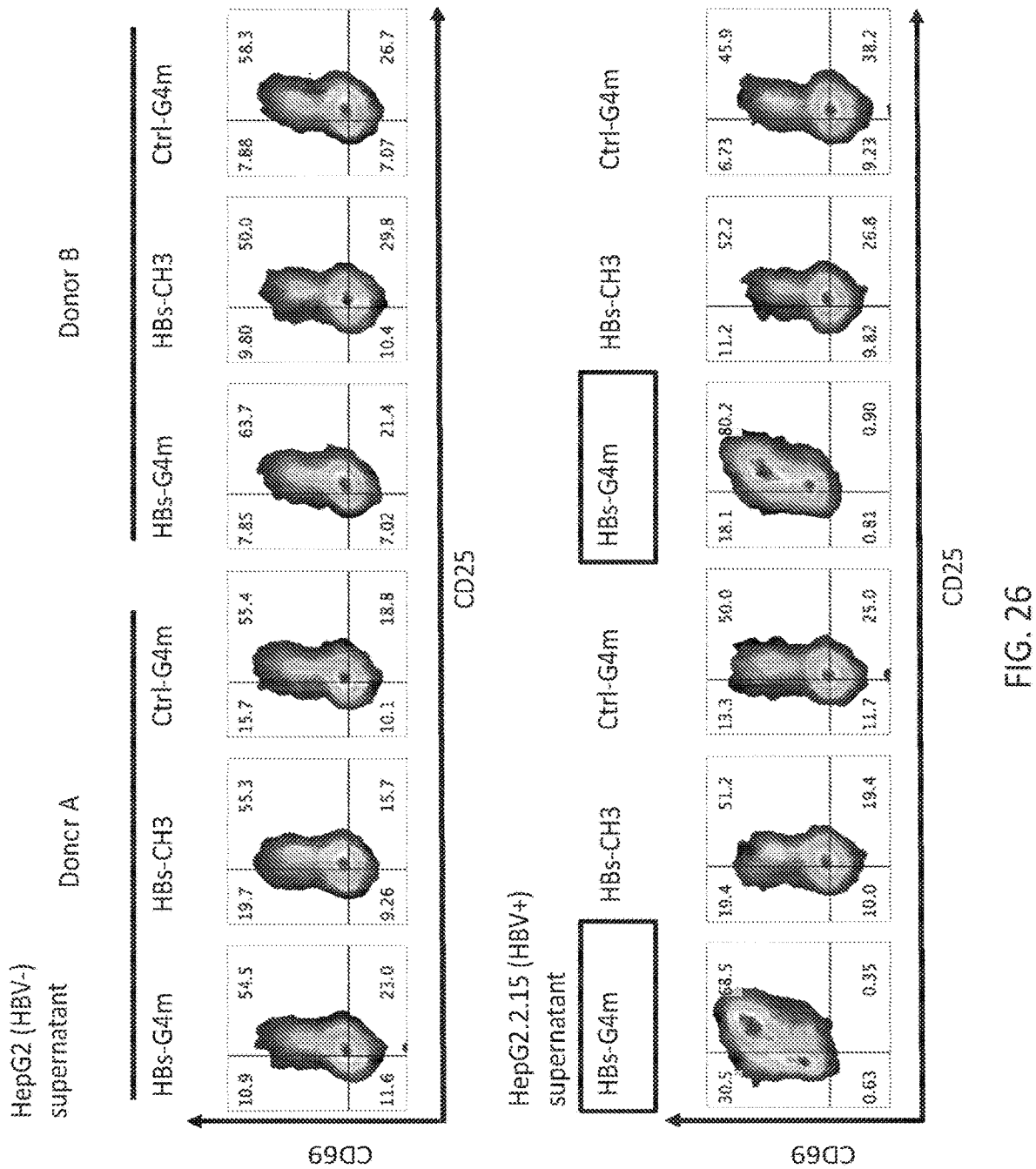
FIG. 26 provides that HBs-G4m-CAR T-cells upregulate activation markers in the presence of HBsAg particles. HBs-G4m-CAR, HBs-CH3-CAR, and Ctrl-G4m-CAR T-cells were cultured with media from HBV+ cells (HepG2.2.15) and HBV− cells (HepG2) and incubated for 24 hours. Cells were then stained for CD25 and CD69 and assessed by FACS analysis for expression levels (n=2 donors).

To determine if HBs-G4m-CAR T-cells recognize HBsAg particles, 24-hour co-culture assays were performed with media supernatants derived from HepG2 and HepG2.2.15 cell lines, the latter containing 80 ng/mL HBsAg. Only HBs-G4m-CAR T-cells secreted significant amounts IFN-γ in the presence of HepG2.2.15-conditioned media in contrast to HBs-CH3-CAR or Ctrl-G4m-CAR T-cells (FIG. 23A). T-cell recognition of HBsAg particles was confirmed by performing FACS analysis for the T-cell activation markers CD25 and CD69 (FIG. 26). To acquire more evidence that HBsAg particles bind to HBs-G4m-CAR T-cells, electron microscopy of HepG2.2.15-conditioned media was performed 24 hours after exposure to HBs-G4m-CAR or Ctrl-G4m-CAR T-cells. While HepG2.2.15-conditioned media exposed to Ctrl-G4m-CAR T-cells contained abundant HBsAg particles, there was a significant reduction in the number of viral particles after exposure to HBs-G4m-CAR T-cells (FIG. 23B,C). Thus, HBsAg particles produced by HepG2.2.15 can bind to HBs-G4m-CAR T-cells and inhibit CAR-T targeting or killing of infected cells.

Figures 24A, 24B, 24C, 24D:
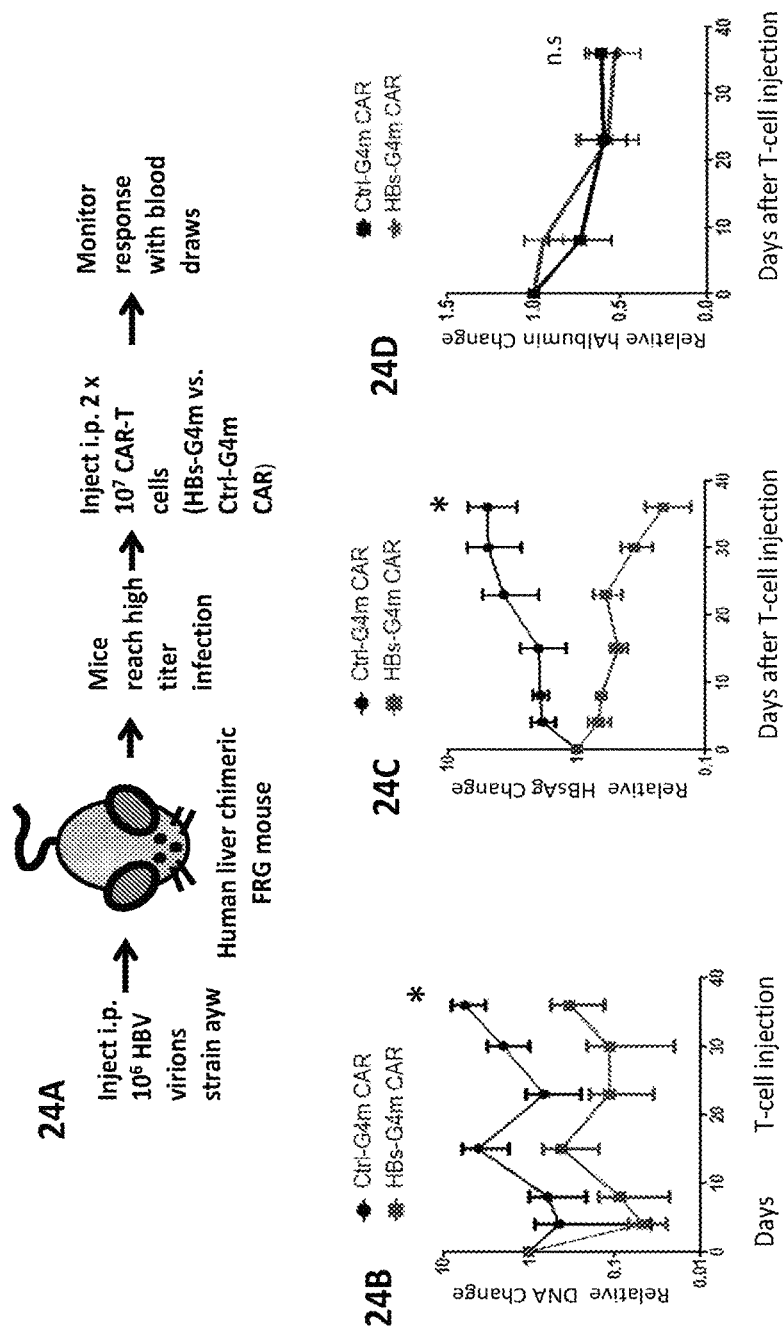
FIG. 24A-24D demonstrate that HBs-G4m-CAR T-cells have anti-HBV activity in vivo. (24A) Scheme of animal experiment. Median pre-treatment values were 17,221 ng/mL HBsAg, and $6.04\times10^7$ copies/ml HBV DNA. Serial monitoring of (24B) HBsAg, (24C) HBV-DNA, and (24D) human albumin (hAlbumin) in plasma of infused mice. Data was normalized to values pre T-cell infusion in individual mice. Average values +/−SEM is depicted; n=4 for HBs-G4m-CAR T-cell group; n=3 for Ctrl-G4m-CAR T-cell group; *$p<0.05$, n.s.: not significant).
Figure 27:
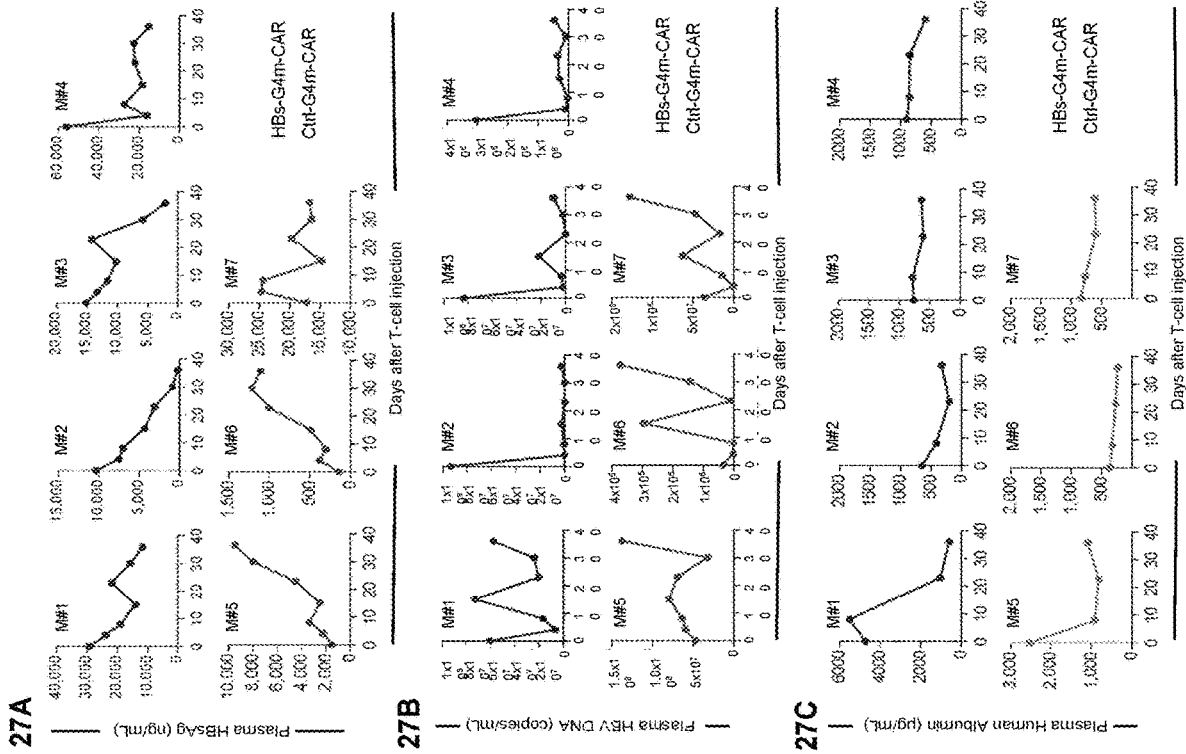
FIGS. 27A-27C demonstrate plasma levels for viral and human markers are reported for individual mice in the treatment and control groups. (27A) Plasma HBsAg levels (ng/mL) for individual mice are reported over time in HBs-G4m-CAR and Ctrl-G4m-CAR T-cells treated mice. (27B) Plasma HBV DNA levels (copies/mL) for individual HBs-G4m-CAR and Ctrl-G4m-CAR treated mice are depicted. (27C) Plasma human albumin levels made by human hepatocytes serves as a proxy for the levels of human hepatocytes in chimeric mice and by extension, toxicity. Human albumin levels (μg/mL) are shown over time in the individual treated mice after initial injection of HBs-G4m-CAR and Ctrl-G4m-CAR T-cells.

HBs-G4m-CAR T-Cells have Anti-HBV Activity in HBV-Infected Human Liver Chimeric Mice HBs-G4m-CAR T-cell therapy was tested in human liver chimeric FRG mice (Bissig, et al., 2007; Azuma, 2007), which can replicate HBV (FIG. 24A) (Bissig, et al., 2010). Mice received $2 \times 10^7$ HBs-G4m-CAR (n=4) or Ctrl-G4m-CAR T-cells (n=3) intraperitoneal, and HBV-DNA and HBsAg levels were measured for five weeks. There was an average 3.0-fold decrease in HBV-DNA levels after 36 days in mice treated with HBs-G4m-CAR T-cells (FIG. 24B), whereas HBV-DNA levels increased an average 5.6-fold in mice that received Ctrl-G4m-CAR T-cells. The decrease in HBV-DNA levels was mirrored by an average 4.7-fold decrease in HBsAg levels in HBs-G4m-CAR T-cell-treated mice, and an average 4.6-fold increase in Ctrl-G4m-CAR T-cell-treated mice (FIG. 24C, FIG. 27A,B). There was no significant difference in plasma human albumin levels between groups, indicating that the anti-HBV activity of HBs-G4m-CAR T-cells is noncytolytic toward infected hepatocytes (FIG. 24D, FIG. 27C).

Figure 28:
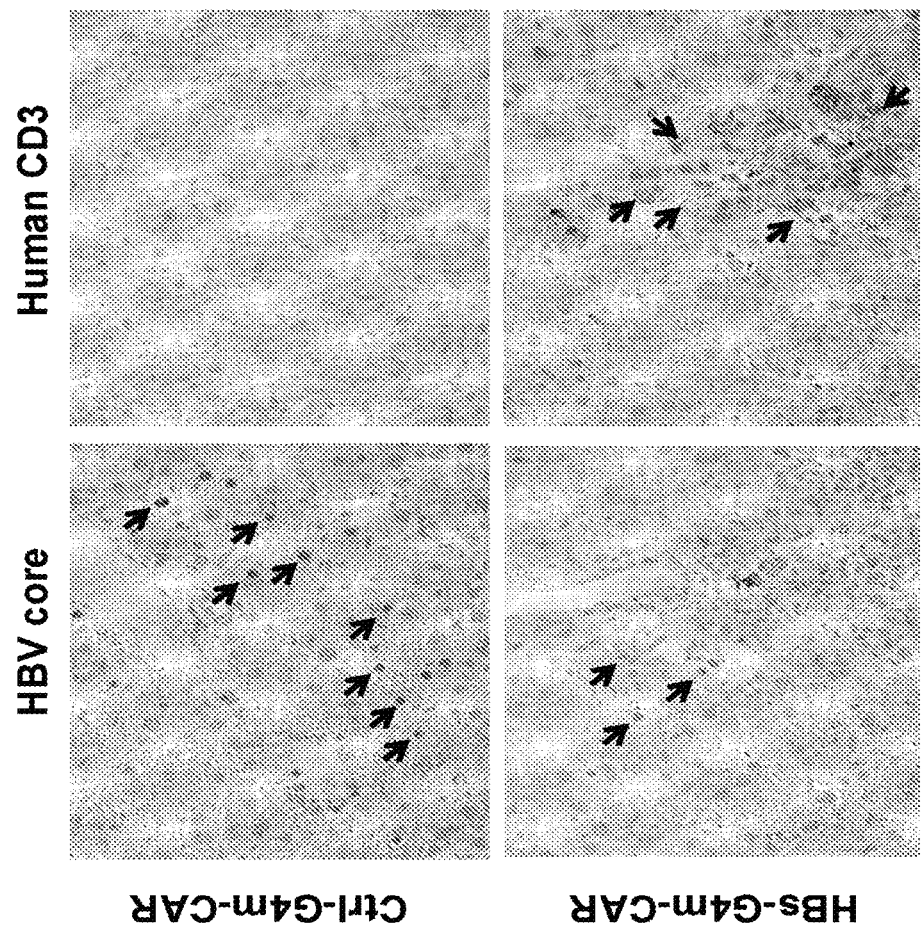
FIG. 28 shows HBs-G4m-CAR T-cells redirected to HBsAg accumulate in the liver of HBV-infected humanized mice. Localization of Ctrl-G4m-CAR and HBs-G4m-CAR T-cells in human liver chimeric mice 10 days post injection was studied using serial sections of paraformaldehyde fixed, paraffin embedded liver tissue, stained for core protein to detect HBV-infected cells (left panels; brown, nuclear stain delineates HBV core protein) and human CD3 to detect human T-cells (right panels; brown, membranous stain delineates CD3 protein; scale bar=20 µm).
Figure 29:
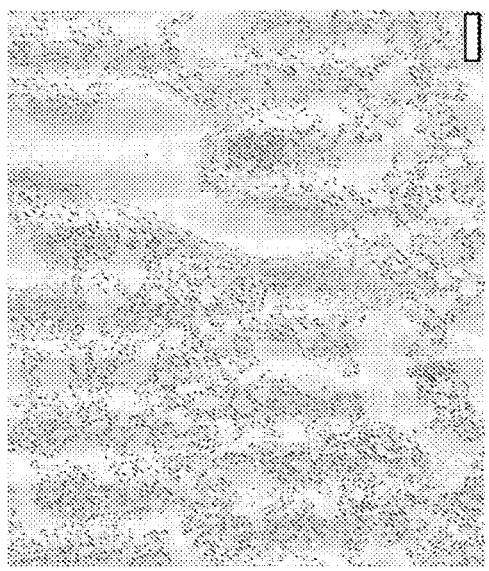
FIG. 29 shows HBs-G4m-CAR T-cells can be found circulating in blood vessels of the lungs. Localization of Ctrl-G4m-CAR and HBs-G4m-CAR T-cells in human liver chimeric mice 10 days post injection was studied using serial sections of paraformaldehyde fixed, paraffin embedded lung tissue, stained for human CD3 to detect human T-cells (brown, membranous stain delineates CD3 protein; scale bar=50 µm).
Figure 29:
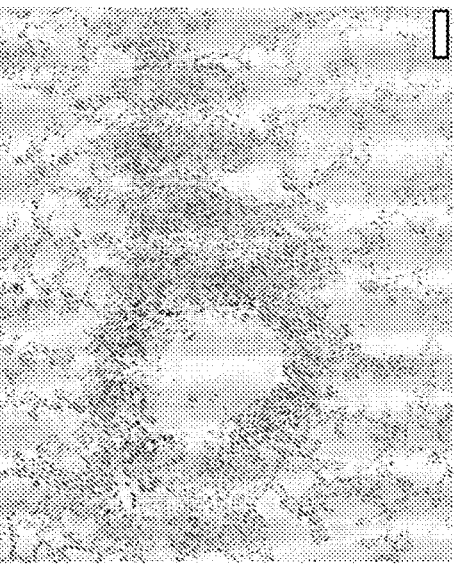
Figure 30:
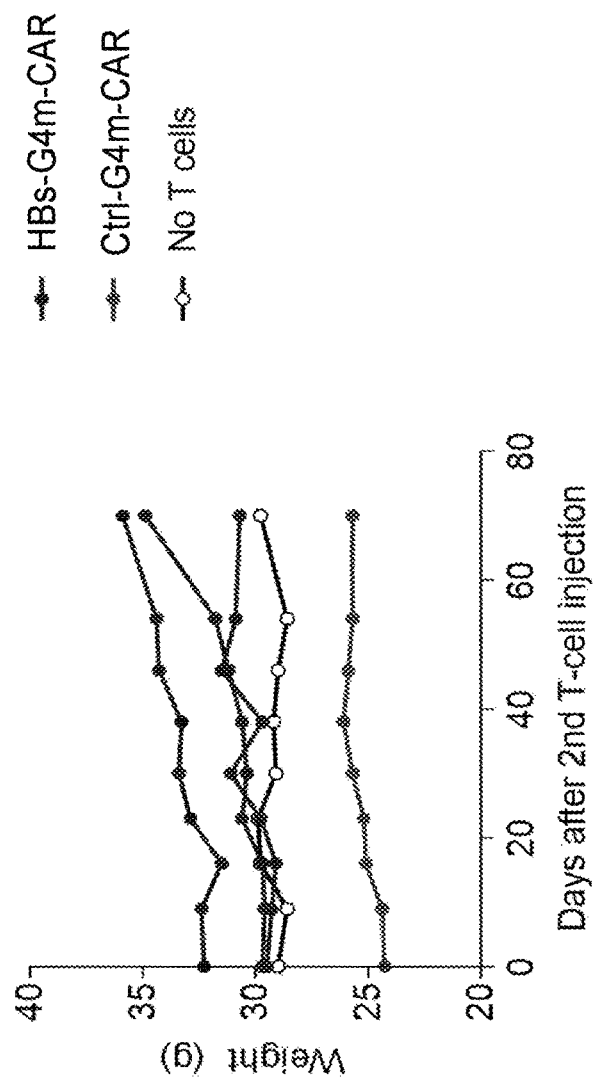
FIG. 30 demonstrates that CAR-T injected mice did not exhibit weight changes indicative of graft-versus-host disease. The weight (in grams) of individual CAR-T treated mice was monitored after the second T-cell injection (HBs-G4m-CAR, Ctrl-G4m-CAR, and no T cell conditions are provided).

To examine liver sections for the presence of T-cells and HBV directly after T-cell infusion, mice received a second dose of $2 \times 10^7$ HBs-G4m-CAR or Ctrl-G4m-CAR T-cells, and were euthanized 10 days post injection. There was a 70.4% decrease in HBV-core staining among human albumin-positive hepatocytes in HBs-G4m-CAR T-cell-treated mice in comparison to control mice (FIG. 25A,B), indicating clearance of HBV through noncytopathic mechanisms, similar to studies in chimpanzees (Guidotti, et al., 1999). This finding was confirmed by staining for human nuclei (FIG. 25A, 25C). Human T-cells could only be detected in livers of mice treated with HBs-G4m-CAR T-cells in contrast to livers of Ctrl-G4m-CAR T-cell-treated mice (FIG. 28), indicating that HBs-G4m-CAR T-cells traffic to livers to exert their anti-HBV activity. Human T-cells were detected in the lung of HBs-G4m-CAR mice but not Ctrl-G4m-CAR mice demonstrating circulation of proliferating CAR-T cells (FIG. 29). At the conclusion of the study, there was no detectable long-term persistence of CAR T-cells in the liver by IHC for CD3. Furthermore, no xenogeneic graft versus host disease (GVHD) was observed, as judged by weight measurements after the $2^{nd}$ T-cell injection (FIG. 30).

Significance of Certain Embodiments

In this study, the inventors demonstrate that HBs-G4m-CAR T-cells are effective in reducing HBV-DNA and HBsAg levels in HBV-infected human liver chimeric mice (Bissig, et al., 2010), which possess cccDNA transcriptional templates. After CAR T-cell therapy, a portion of human hepatocytes was also found to have histologically absent HBV core expression. However, complete elimination of HBV was not observed, which is most likely due to the limited persistence of human CAR T-cells in immunodeficient mouse models (Park, et al., 2007), possibly facilitated in immunodeficient mice on the FRG background by lack of murine SIRPα engagement (Legrand, et al., 2011), as opposed to NOD background models (Takenaka, et al., 2007). Despite this limitation, HBs-G4m-CAR T cells had superior anti-HBV activity than HBV entry inhibitors (Nakabori, et al., 2016) that did not reduce the number of HBV-infected hepatocytes in a humanized mouse model of established HBV infection. This finding also extends the work of the previous HBV-CAR publication in transgenic mice, which was unable to assess if HBV could be cleared from hepatocytes, because every cell had integrated virus allowing HBV core expression to quickly return (Krebs, et al., 2013).

HBs-G4m-CAR T-cells recognized HBsAg-positive HepG2.2.15 cells as judged by cytokine production, but had no cytolytic activity in a 5-hour cytotoxicity assay. Incubating HBs-G4m-CAR T-cells for up to 5 days with HepG2.2.15 cells also did not demonstrate any cytolytic activity of HBs-G4m-CAR T-cells. By comparison, a previous study had demonstrated that T cells, genetically modified with a different HBsAg-CAR, killed HBsAg-positive target cells at 72 hours (Bohne, et al., 2008) indicating both CARs may be inefficient at killing. While both CARs are HBsAg specific, different scFvs were used as antigen-binding domains. In specific embodiments, and without being bound by theory, differences in scFv binding sites between both CARs could explain these differences, since epitope location in part governs CAR T-cell activity (Hombach, et al., 2007). Competition by soluble HBsAg particles is unlikely since the HBV-positive HepG2.2.15 cells were washed immediately prior to cytotoxicity assays, and the CARs of both studies were able to recognize soluble HBsAg particles. Importantly, HBsAg levels in the humanized model are around 10-fold higher than in HBV transgenic mice, which may have prevented in the system the transient transaminase elevation seen in the previous work (Krebs, et al., 2013). In particular, the intrinsic, unique, and unexpected characteristics of lack of efficient cytotoxicity discovered in XTL19 scFv-CAR design may have also played a role, with unique epitope binding and signaling properties, compared to the previously published HBV-CAR molecule, which had more cytotoxicity.

In particular embodiments, having HBsAg-CAR T cells that do not kill hepatocytes efficiently is a significant advantage, best exemplified by the observation that adoptive transfer of PBMCs of HBV-seropositive donors, which contain HBV-specific T cells that recognize HBV-derived peptides in the context of MHC class I, induce acute liver failure in an HBV-infected humanized mouse model (Uchida, et al., 2015). Intriguingly, the inventors did find that the mouse with the lowest initial HBsAg levels did have the best results in HBsAg and DNA knockdown (−1.65 log and −3.67 log, respectively), indicating some inhibitory role of HBsAg may be at play, or that the disease burden may be too great for CAR T-cells, in certain embodiments.

Because HBsAg-CAR T-cell therapy employs a different mechanism to eradicate HBV than currently approved therapies, one can consider combinatorial approaches. For example, combining CAR T-cells with RTIs may prevent rebound of viral DNA levels post CAR T-cell therapy that was observed herein. Furthermore, hepatitis B immunoglobulin (HBIG) administration prior to CAR T-cell infusion may be useful to reduce serum HBsAg levels, in some embodiments. This should restrict CAR T-cell activation and proliferation to sites of HBV-infected hepatocytes that produce HBsAg particles as opposed to HBsAg particle deposition sites, increasing not only efficacy but also reducing the risk of systemic CAR T-cell activation, which could result in cytokine release syndrome (Brudno, et al., 2016). Furthermore, pretreatment with HBIG would 'mask' HBsAg particles, which have accumulated outside the liver, reducing on-target, off-tissue toxicity. Lastly, in some embodiments systemic toxicity could be prevented by directly injecting CAR T-cells into the hepatic artery, bypassing systemic circulation.

In conclusion, HBs-G4m-CAR T cells are effective in reducing HBV levels in plasma and tissue in HBV-infected human liver chimeric mice.

Examples of Methods

All methods were performed in accordance with national guidelines and regulations.

Generation of Retroviral Vectors Encoding CARs

To generate pSFG-HBs-G4m-28-zeta, a scFv encoding the amino acid sequence VH and VL domains of the XTL-19 antibody (mAb 19.79.5) (Eren, et al., 2000) termed HBs was synthesized (IDTDNA, Coralville, Iowa), and cloned into an SFG retroviral vector using 5' NcoI and 3' BamHI, replacing the antigen binding domain from a second generation CAR vector, IL13Rα2-hIgG1-CD28-zeta CAR (Krebs, et al., 2014). Next, the hIgG1 hinge was replaced with a mini-gene (synthesized by IDTDNA, Coralville, Iowa) encoding the CH2-CH3 domain from human IgG4 with mutated Fc receptor binding sites (Hudecek, et al., 2015) (G4m) to generate pSFG-HBs-G4m-28-zeta. To generate pSFG-Ctrl-G4m-28-zeta, the HBs-specific scFv in pSFG-HBs-G4m-28-zeta was replaced by PCR cloning with an scFv specific for EGFRvIII (Morgan, et al., 2012). pSFG-HBs-CH3-28-zeta was generated by cloning the HBs-specific scFv into the 5' NcoI and 3' BamHI sites of a pSFG vector with a CAR.IgG1 CH3.28-zeta expression cassette (gift of Dr. Maksim Mamonkin, Baylor College of Medicine, Houston, Tex.). Cloning was verified by sequencing (Lone Star Labs, Houston Tex.). RD114-pseudotyped retroviral particles were generated by transient transfection of 293T cells as previously described (Ahmed, et al., 2010).

Generation of CAR-T Cells

To generate CAR-T cells, PBMCs were isolated by Lymphoprep (Greiner Bio-One, Monroe, N.C.) gradient centrifugation and then stimulated on treated non-tissue culture 24-well plates, which were pre-coated with OKT3 (CRL-8001, ATCC) and CD28 (BD Bioscience, Mountain View, Calif.) antibodies. Recombinant human interleukin-7 and interleukin-15 (IL-7, 10 ng/mL; IL-15, 5 ng/mL; PeproTech, Rocky Hill, N.J.) were added to cultures on day 2. On day 3, OKT3/CD28 stimulated T-cells ($2.5 \times 10^5$ cells/well) were transduced on RetroNectin® (Clontech, Mountainview, Calif.) coated plates in the presence of IL-7 and IL-15. On day 5 or 6, T-cells were transferred into tissue culture plates and subsequently expanded with IL-7 and IL-15. CAR expression was determined 4 to 5 days post transduction by FACS analysis using a human IgG (H+L) antibody (Jackson Immunoresearch, West Grove, Pa.), and appropriate isotype control.

Cell Culture Assays

HepG2.2.15 cells (gift of Dr. Betty Slagle, Baylor College of Medicine, Houston, Tex.) and HepG2 cells (ATCC, Manassas, Va.) were cultured in Dulbecco's minimal essential media (DMEM) supplemented with 10% fetal bovine serum and 1% antibiotic-antimycotic (Gibco ThermoFisher, Waltham, Mass.). For co-culture assays, 1 million HepG2 or HepG2.2.15 cells were plated; 24-hours later cells were washed and 2 million T-cells were added in one well of a 24-well plate in duplicate without exogenous cytokines. After 24 hours, supernatant was removed in order to assess cytokine release. For cytokine ELISAs, concentrations of INF-γ were assessed using manufacturer's protocol (R&D Systems, Minneapolis, Minn.). For IL-2 and TNF-α, cytokine levels were determined using a multiplex assay (Millipore, St. Charles, Mo.). For cytotoxicity assays, standard chromium release protocols were followed as previously described (Krebs, et al., 2014) utilizing the same 2:1 ratio of T-cell to target cell, wherein target cells were plated on the same day as T-cell addition preventing any HBsAg particle accumulation.

For cytokine assays based on co-culture with HBV particles, the HepG2.2.15 supernatant was collected (measured to be 80 ng/mL using HBsAg ELISA protocol below). Culture media contained 50% HepG2.2.15 supernatant with 1 million CAR-T cells. At 24 hours, supernatant was collected for use in cytokine ELISA assays and electron microscopy particle counts. T-cells were also collected at this time point for analysis by flow cytometry using established protocols (Krebs, et al., 2014) and staining cells with anti-CD25-PE (BD Biosciences, San Jose, Calif.) and anti-CD69-APC (BD Biosciences, San Jose, Calif.). Flow cytometric data were acquired by Gallios (Beckman Coulter, Brea, Calif.) and analyzed using FlowJo ver.10 (FlowJo, Ashland, Oreg.).

Electron Microscopy

HBsAg particles and HBV virions were visualized by electron microscopy in conjunction with the Integrated Microscopy Core at Baylor College of Medicine. For negative staining for electron microscopy, cell culture supernatants were directly adsorbed to 2 formvar and carbon coated 200 mesh EM grid (EMS #FCF200-CU), washed once with ddH$_2$O to remove salts and negatively stained with 1% ammonium molydbate. The samples were imaged using a JEOL JEM-1230 transmission electron microscope (Peabody, Mass.) at 80 kV. Images were taken from multiple areas of both specimen grids at random locations, using a Gatan Ultrascan 1000 CCD camera and Gatan Digital Micrograph imaging software (Pleasanton, Calif.). Examination of the micrographs was performed using Digital Micrograph and the FIJI implementation of the NIH ImageJ software.

Animal Experiments

Fah$^{-/-}$ Rag2$^{-/-}$ Il2-rg$^{-/-}$ (FRG) mice were repopulated with human cadaveric hepatocytes, as described previously (Bissig, et al., 2010; Bissig, et al., 2007). For the current experiment, all human liver chimeric mice were repopulated with hepatocytes from the same hepatocyte donor and lot in order to minimize differences. Furthermore, at the initiation of cell injection, mice were kept on 100% NTBC (2-(2-nitro-4-trifluoromethylbenzoyl)-1,3-cyclohexanedione) in order to stabilize the levels of human hepatocytes, and prevent ongoing destruction of murine hepatocytes and proliferation of human hepatocytes, that otherwise might contribute to either increasing HBV levels, or the loss of cccDNA after hepatocyte mitosis.

One million genome equivalents of HBV genotype D (serotype yaw) were inoculated intraperitoneal into humanized FRG mice as previously described (Bissig, et al., 2010). The infection was allowed to spread over 1-2 months until mice reached high levels of HBV infection, monitored by qPCR and HBsAg ELISA. HBsAg-CAR or Ctrl-CAR T-cells were injected intraperitoneal into humanized mice. Mice were monitored with retro-orbital bleeds collected into EDTA containing tubes, and plasma collected after centrifugation for 30 minutes at 2.3G. Collected plasma was frozen until further use for HBV-DNA, HBsAg, and human albumin analysis.

Plasma Analysis

Plasma HBsAg levels was quantified using commercially available ELISA reagents (International Immuno Diagnostics, Foster City, Calif.) and HBsAg standards (Alpha Diagnostic International, San Antonio, Tex.). Plasma HBV DNA levels were determined by quantitative PCR as previously described (Billioud, et al., 2016). Human plasma albumin levels were assessed by ELISA (Bethyl laboratories, Montgomery, Tex.) and was performed according to manufacturer's protocol.

Immunohistochemistry

Liver frozen tissue slides were fixed for 10 minutes with 4% PFA. Co-staining against HBV and human markers was performed overnight at 4° C. in PBS-T buffer (PBS 1× containing 0.5% BSA and 0.2% of triton-100) using the following primary antibodies: rabbit anti-hepatitis B virus core antigen (Dako/Agilent, Santa Clara, Calif.), mixed either with goat anti-human Albumin (Bethyl laboratories, Montgomery, Tex.) or with mouse anti-human Nuclei antibody (Millipore, St. Charles, Mo.). After washing the primary antibodies with PBS 1×, slides were incubated for 1 hour at room temperature with Alexa-Fluor secondary antibodies (Molecular Probes, Eugene, Oreg.). Vectashield plus DAPI (Vector Labs, Burlingame, Calif.) was used for slides mounting.

Serial sections of paraffin-embedded liver were first dewaxed, rehydrated, and blocked with hydrogen peroxide. For T-cell staining, antigen retrieval at 90° C. with citrate buffer (Dako/Agilent) was performed followed by blocking with M.O.M Ig blocking solution (Vector Labs). Mouse anti-human CD3 primary antibody (Leica Biosystems, Buffalo Grove, Ill.) was then applied. For HBV staining, slides were first blocked with goat serum (Vector Labs), followed by incubation with rabbit anti-HBV core antigen primary antibody (Dako/Agilent). Corresponding biotinylated secondary antibodies from M.O.M and Rabbit Vectastain ABC kits were next added (Vector Labs). Staining was developed using DAB peroxidase substrate kit (Vector Labs) following manufacturer's recommendations. Hematoxylin was used for counterstaining and Vectamount AQ (Vector Labs) media was used to mount the slides.

Images were visualized and quantified with NIH ImageJ software in order to assess HBV core to human albumin or human nuclear positive cell ratios among the human liver chimer mouse sections. This was done by manual, individual counting of every positive cell in a given field for two different markers (either HBV core and human albumin or human nuclear) denoted with different tags in ImageJ. Random sections of livers for a total of 4 fields containing human hepatocytes were selected to remove bias.

Statistics

Statistical analysis was performed using GraphPad Prism 7 software (GraphPad Software, Inc., La Jolla, Calif.). Data measurements are presented as mean+/−standard error of mean (SEM). Mean differences were tested using appropriate tests including unpaired, parametric, one-tailed t-tests. Significance level used was $p<0.05$, unless otherwise specified.

Study Approval

Human peripheral blood mononuclear cells (PBMCs) from healthy donors were obtained under a Baylor College of Medicine IRB approved protocol, after informed consent was obtained in accordance to the Declaration of Helsinki. All animal experiments followed a protocol approved by the Baylor College of Medicine Institutional Animal Care and Use Committee.

Although embodiments of the present invention and its advantages have been described in detail, it should be understood that various changes, substitutions and alterations can be made herein without departing from the spirit and scope of the inventions as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present inventions. Accordingly, the appended claims are intended to include within their scope such processes, machines, manufacture, compositions of matter, means, methods, or steps.

REFERENCES

Ahmed, N. et al. HER2-specific T cells target primary glioblastoma stem cells and induce regression of autologous experimental tumors. Clin Cancer Res 16, 474-485 (2010).

Azuma, H. et al. Robust expansion of human hepatocytes in Fah−/−/Rag2−/−/Il2rg−/− mice. Nat. Biotechnol. 25, 903-910 (2007).

Billerbeck, E. et al. Humanized mice efficiently engrafted with fetal hepatoblasts and syngeneic immune cells develop human monocytes and NK cells. Journal of Hepatology 65, 334-343 (2016).

Billioud, G. et al. In vivo reduction of hepatitis B virus antigenemia and viremia by antisense oligonucleotides. Journal of Hepatology 64, 781-789 (2016).

Bissig, K.-D. et al. Human liver chimeric mice provide a model for hepatitis B and C virus infection and treatment. J. Clin. Invest. 120, 924-930 (2010).

Bissig, K.-D., Le, T. T., Woods, N.-B. & Verma, I. M. Repopulation of adult and neonatal mice with human hepatocytes: a chimeric animal model. Proc. Natl. Acad. Sci. U.S.A. 104, 20507-20511 (2007).

Bohne, F. et al. T Cells Redirected Against Hepatitis B Virus Surface Proteins Eliminate Infected Hepatocytes. Gastroenterology 134, 239-247 (2008).

Boni, C. et al. Characterization of hepatitis B virus (HBV)-specific T-cell dysfunction in chronic HBV infection. Journal of Virology 81, 4215-4225 (2007).

Brudno, J. N. & Kochenderfer, J. N. Toxicities of chimeric antigen receptor T cells: recognition and management. Blood 127, 3321-3330 (2016).

Eren, R. et al. Preclinical Evaluation of Two Human Anti-Hepatitis B Virus (HBV) Monoclonal Antibodies in the HBV-Trimera Mouse Model and in HBV Chronic Carrier Chimpanzees. Hepatology 32, 588-596 (2000).

Galun, E. et al. Clinical evaluation (phase I) of a combination of two human monoclonal antibodies to HBV: safety and antiviral properties. Hepatology 35, 673-679 (2002).

Guidotti, L. G. et al. Intracellular inactivation of the hepatitis B virus by cytotoxic T lymphocytes. Immunity 4, 25-36 (1996).

Guidotti, L. G. et al. Viral clearance without destruction of infected cells during acute HBV infection. Science 284, 825-829 (1999).

Hoh, A. et al. Hepatitis B Virus-Infected HepG2hNTCP Cells Serve as a Novel Immunological Tool To Analyze the Antiviral Efficacy of CD8+ T Cells In vitro. Journal of Virology 89, 7433-7438 (2015).

Hombach, A. A. et al. T cell activation by antibody-like immunoreceptors: the position of the binding epitope within the target molecule determines the efficiency of activation of redirected T cells. J. Immunol. 178, 4650-4657 (2007).

Hudecek, M. et al. The nonsignaling extracellular spacer domain of chimeric antigen receptors is decisive for in vivo antitumor activity. Cancer Immunol Res 3, 125-135 (2015).

Krebs, K. et al. T cells expressing a chimeric antigen receptor that binds hepatitis B virus envelope proteins control virus replication in mice. Gastroenterology 145, 456-465 (2013).

Krebs, S. et al. T cells redirected to interleukin-13Rα2 with interleukin-13 mutein—chimeric antigen receptors have anti-glioma activity but also recognize interleukin-13Rα1. Cytotherapy 16, 1121-1131 (2014).

Legrand, N. et al. Functional CD47/signal regulatory protein alpha (SIRP(alpha)) interaction is required for optimal human T- and natural killer-(NK) cell homeostasis in vivo. Proc. Natl. Acad. Sci. U.S.A. 108, 13224-13229 (2011).

Liaw, Y.-F. HBeAg seroconversion as an important end point in the treatment of chronic hepatitis B. Hepatol Int 3, 425-433 (2009).

Morgan, R. A. et al. Recognition of glioma stem cells by genetically modified T cells targeting EGFRvIII and development of adoptive cell therapy for glioma. Human Gene Therapy 23, 1043-1053 (2012).

Nakabori, T. et al. Sodium taurocholate cotransporting polypeptide inhibition efficiently blocks hepatitis B virus spread in mice with a humanized liver. Scientific Reports 6, 27782 (2016).

Ning, Q. et al. Switching from entecavir to PegIFN alfa-2a in patients with HBeAg-positive chronic hepatitis B: a randomised open-label trial (OSST trial). Journal of Hepatology 61, 777-784 (2014).

Park, J. R. et al. Adoptive transfer of chimeric antigen receptor re-directed cytolytic T lymphocyte clones in patients with neuroblastoma. Mol Ther 15, 825-833 (2007).

Perz, J. F., Armstrong, G. L., Farrington, L. A., Hutin, Y. J. F. & Bell, B. P. The contributions of hepatitis B virus and hepatitis C virus infections to cirrhosis and primary liver cancer worldwide. Journal of Hepatology 45, 529-538 (2006).

Phillips, S. et al. CD8(+) T cell control of hepatitis B virus replication: direct comparison between cytolytic and non-cytolytic functions. J. Immunol. 184, 287-295 (2010).

Shepard, C. W., Simard, E. P., Finelli, L., Fiore, A. E. & Bell, B. P. Hepatitis B virus infection: epidemiology and vaccination. Epidemiol Rev 28, 112-125 (2006).

Takenaka, K. et al. Polymorphism in Sirpa modulates engraftment of human hematopoietic stem cells. Nat. Immunol. 8, 1313-1323 (2007).

Thimme, R. et al. CD8(+) T cells mediate viral clearance and disease pathogenesis during acute hepatitis B virus infection. Journal of Virology 77, 68-76 (2003).

Uchida, T. et al. Human Cytotoxic T Lymphocyte-Mediated Acute Liver Failure and Rescue by Immunoglobulin in Human Hepatocyte Transplant TK-NOG Mice. Journal of Virology 89, 10087-10096 (2015).

Washburn, M. L. et al. A humanized mouse model to study hepatitis C virus infection, immune response, and liver disease. Gastroenterology 140, 1334-1344 (2011).

Wieland, S. F., Spangenberg, H. C., Thimme, R., Purcell, R. H. & Chisari, F. V. Expansion and contraction of the hepatitis B virus transcriptional template in infected chimpanzees. Proc Natl Acad Sci USA 101, 2129-2134 (2004).

Xia, Y. et al. Interferon-γ and Tumor Necrosis Factor-α Produced by T Cells Reduce the HBV Persistence Form, cccDNA, Without Cytolysis. Gastroenterology 150, 194-205 (2016).

What is claimed is:

1. A polynucleotide encoding a non-cytotoxic chimeric antigen receptor (CAR), wherein the non-cytotoxic CAR comprises a single chain variable fragment (scFv) derived from monoclonal antibody 19.79.5 (XTL-19).

2. The polynucleotide of claim 1, wherein the CAR comprises a linker region of at least two immunoglobulin domains.

3. The polynucleotide of claim 2, wherein the linker region comprises an IgG Fc region.

4. The polynucleotide of claim 3, wherein the IgG Fc region is from IgG4.

5. The polynucleotide of claim 3, wherein the IgG Fc region comprises one or more mutations.

6. The polynucleotide of claim 5, wherein the CAR has reduced binding to an Fc Receptor.

7. The polynucleotide of claim 5, wherein the IgG Fc region lacks the CH2 domain, has a CH2 domain from a different IgG, or has an immunoglobulin domain from a different human protein.

8. The polynucleotide of claim 7, wherein the different human protein is CD4, CD8, CD19, or CD22.

9. The polynucleotide of claim 8, wherein the IgG Fc region is the IgG2 Fc region that comprises the IgG4 CH2 domain instead of the native IgG2 CH2 domain.

10. The polynucleotide of claim 5, wherein the one or more mutations are in the glycosylation site of the IgG Fc domain or in the hinge region of the IgG Fc domain.

11. The polynucleotide of claim 1, wherein the CAR lacks one or more signaling endodomains that trigger perforin secretion or granzyme secretion or has a mutation in one or more residues for signaling in the signaling endodomain(s).

12. The polynucleotide of claim 1, wherein the CAR lacks the zeta chain or has a mutation in the zeta chain disrupting optimal signaling.

13. The polynucleotide of claim 1, wherein the CAR lacks the CD16 gamma chain.

14. An isolated cell, comprising the polynucleotide of claim 1.

15. The isolated cell of claim 14, wherein the cell is an immune cell.

16. The isolated cell of claim 15, wherein the immune cell is a T cell, NK cell, NK T cell, macrophage, or monocyte.

17. The isolated cell of claim 14, wherein the cell is a T cell that lacks native T-cell receptors or has reduced levels of native T-cell receptors compared to a normal T cell.

18. The isolated cell of claim 14, wherein the cell comprises an engineered receptor that is different from the receptor encoded by the polynucleotide.

19. The isolated cell of claim 18, wherein the engineered receptor is a CAR, chimeric cytokine receptor, membrane-bound antibody, or αβ T cell receptor.

20. The isolated cell of claim 18, wherein the engineered receptor binds to a different epitope of an HBV antigen not targeted by the receptor encoded by the polynucleotide.

21. The isolated cell of claim 20, wherein the engineered receptor and the receptor encoded by the polynucleotide associate with each other in order to generate synergistic affinity.

22. The isolated cell of claim 18, wherein the engineered receptor comprises one or more agents that target a Hepatitis B antigen.

23. The isolated cell of claim 14, wherein the cell comprises a genetic knockout of MHC class I and/or MHC class II expression.

24. A method of treating an individual for hepatitis B, comprising the step of delivering to the individual a therapeutically effective amount of cells of claim 14.

25. The method of claim 24, wherein the individual is lymphodepleted prior to administration of the cells.

26. The method of claim 24, wherein the cells are allogeneic or autologous to the individual.

27. The method of claim 24, wherein the individual is given an additional therapy for Hepatitis B infection.

28. The method of claim 24, wherein prior to, during, and/or after the delivery of the cells the individual is given a therapeutically effective amount of one or more antibodies that recognize a Hepatitis B antigen.

29. The method of claim 24, wherein the cells further comprise one or more agents that reduce cytotoxicity by modulating expression of perforin, granzyme A, granzyme B, granzyme C, granzyme D, Fas receptor, Fas ligand, TNF-alpha, TRAIL, beta-2 microglobulin, MEW class II molecules, and/or MEW class I molecules.

30. The method of claim 29, wherein the agents that reduce expression comprise microRNAs, siRNAs, shRNAs or IncRNAs.

31. The method of claim 30, wherein the microRNA is human microRNA-150, human microRNA-27a*, microRNA-378, microRNA-30e, microRNA-139, microRNA-342, microRNA-378, or microRNA-23a.

32. The method of claim 18, wherein the CAR and the engineered receptor target different antigens.

33. The method of 18, wherein the CAR and the engineered receptor target different epitopes of the same antigen.

34. The method of claim 24, wherein prior to, during, and/or after the delivery of the cells the individual is given a therapeutically effective amount of one or more reverse transcriptase inhibitors and/or one or more interferon-alpha derivatives.

35. The method of claim 24, wherein the individual is determined to have or remedied with anti-HBsAg antibodies to have a baseline serum or plasma value of HBV surface antigen of 1,000 or 5,000 ng/mL or lower, prior to, concurrently and/or after CAR-T cell administration, thereby leading to improved therapeutic response to the CAR-T cell therapy.

* * * * *

SEQUENCE LISTING

```
<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Ser Gly Ser Gly Leu Lys Lys Lys Trp Ser Thr
1               5                   10
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Glu Thr Gly Ala Lys Pro His Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Lys His Met His Trp His Pro Pro Ala Leu Asn Thr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Ser Gly Ser Gly Trp Thr Asn Trp Trp Ser Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Asn Asn Trp Trp Tyr Trp Trp Asp Thr Leu Val Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Gly Leu Trp Arg Phe Trp Phe Gly Asp Phe Leu Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Trp Thr Asp Met Phe Thr Ala Trp Trp Ser Thr Pro
1               5                   10
```

-continued

```
<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 8

Leu Arg Asn Ile Arg Leu Arg Asn Ile Arg Leu Arg Asn Ile Arg Leu
1               5                   10                  15

Arg Asn Ile Arg
            20

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Cys Ser Arg Leu Leu Tyr Gly Trp Cys
1               5

<210> SEQ ID NO 10
<211> LENGTH: 638
<212> TYPE: PRT
<213> ORGANISM: Artificial Sequence
<220> FEATURE:
<223> OTHER INFORMATION: Synthetic Peptide

<400> SEQUENCE: 10

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
                20                  25                  30

Pro Gly Gly Ser Leu Arg Leu Ser Cys Ala Pro Ser Gly Phe Val Phe
            35                  40                  45

Arg Ser Tyr Gly Met His Trp Val Arg Gln Thr Pro Gly Lys Gly Leu
    50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Ser Gly Gly Gly Gly
    130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220
```

```
Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
            245                 250                 255

Gly Thr Thr Leu Thr Val Leu Gly Ser Gly Gly Gly Gly Ser Glu Ser
                260                 265                 270

Lys Tyr Gly Pro Pro Cys Pro Ser Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Gln Ser Thr Tyr Arg
                340                 345                 350

Val Val Ser Val Leu Thr Val Leu His Gln Asp Trp Leu Asn Gly Lys
            355                 360                 365

Glu Tyr Lys Cys Lys Val Ser Asn Lys Gly Leu Pro Ser Ser Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Lys Asp Pro Lys Phe Trp Val Leu Val Val Val Gly Gly Val
            500                 505                 510

Leu Ala Cys Tyr Ser Leu Leu Val Thr Val Ala Phe Ile Ile Arg Val
        515                 520                 525

Lys Phe Ser Arg Ser Ala Asp Ala Pro Ala Tyr Gln Gln Gly Gln Asn
    530                 535                 540

Gln Leu Tyr Asn Glu Leu Asn Leu Gly Arg Arg Glu Glu Tyr Asp Val
545                 550                 555                 560

Leu Asp Lys Arg Arg Gly Arg Asp Pro Glu Met Gly Gly Lys Pro Arg
                565                 570                 575

Arg Lys Asn Pro Gln Glu Gly Leu Tyr Asn Glu Leu Gln Lys Asp Lys
            580                 585                 590

Met Ala Glu Ala Tyr Ser Glu Ile Gly Met Lys Gly Glu Arg Arg Arg
        595                 600                 605

Gly Lys Gly His Asp Gly Leu Tyr Gln Gly Leu Ser Thr Ala Thr Lys
    610                 615                 620

Asp Thr Tyr Asp Ala Leu His Met Gln Ala Leu Pro Pro Arg
625                 630                 635
```

<210> SEQ ID NO 11
<211> LENGTH: 606
<212> TYPE: PRT
<213> ORGANISM: Artificial Sequence
<220> FEATURE:
<223> OTHER INFORMATION: Synthetic Peptide

<400> SEQUENCE: 11

```
Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Gln
            20                  25                  30

Pro Gly Gly Ser Leu Arg Leu Ser Cys Ala Pro Ser Gly Phe Val Phe
        35                  40                  45

Arg Ser Tyr Gly Met His Trp Val Arg Gln Thr Pro Gly Lys Gly Leu
    50                  55                  60

Glu Trp Val Ser Leu Ile Trp His Asp Gly Ser Asn Arg Phe Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Arg Leu Ile Ala Ala Pro Ala Ala Phe Asp
        115                 120                 125

Leu Trp Gly Gln Gly Thr Leu Val Thr Val Ser Gly Gly Gly Gly Gly
    130                 135                 140

Ser Gly Gly Gly Gly Ser Gly Gly Gly Gly Ser Ser Tyr Val Leu Thr
145                 150                 155                 160

Gln Pro Pro Ser Val Ser Val Ala Pro Gly Lys Thr Ala Arg Ile Ser
                165                 170                 175

Cys Gly Gly Asn Asn Ile Gly Thr Lys Asn Val His Trp Tyr Gln Gln
            180                 185                 190

Lys Pro Gly Gln Ala Pro Val Leu Val Val Tyr Ala Asp Ser Asp Arg
        195                 200                 205

Pro Ser Gly Ile Pro Glu Arg Phe Ser Gly Ser Asn Ser Gly Asn Thr
    210                 215                 220

Ala Thr Leu Thr Ile Ser Arg Val Glu Val Gly Asp Glu Ala Asp Tyr
225                 230                 235                 240

Tyr Cys Gln Val Trp Asp Ser Val Ser Tyr His Val Val Phe Gly Gly
                245                 250                 255

Gly Thr Thr Leu Thr Val Leu Gly Ser Gly Gly Gly Gly Ser Glu Ser
            260                 265                 270

Lys Tyr Gly Pro Pro Cys Pro Ser Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Gln Ser Thr Tyr Arg
            340                 345                 350

Val Val Ser Val Leu Thr Val Leu His Gln Asp Trp Leu Asn Gly Lys
        355                 360                 365
```

```
Glu Tyr Lys Cys Lys Val Ser Asn Lys Gly Leu Pro Ser Ser Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Lys Asp Pro Lys Phe Trp Val Leu Val Val Val Gly Gly Val
            500                 505                 510

Leu Ala Cys Tyr Ser Leu Leu Val Thr Val Ala Phe Ile Ile Phe Trp
        515                 520                 525

Val Arg Ser Lys Arg Ser Arg Leu Leu His Ser Asp Tyr Met Asn Met
530                 535                 540

Thr Pro Arg Arg Pro Gly Pro Thr Arg Lys His Tyr Gln Pro Tyr Ala
545                 550                 555                 560

Pro Pro Arg Asp Phe Ala Ala Tyr Arg Ser Arg Asp Gln Arg Leu Pro
                565                 570                 575

Pro Asp Ala His Lys Pro Pro Gly Gly Gly Ser Phe Arg Thr Pro Ile
            580                 585                 590

Gln Glu Glu Gln Ala Asp Ala His Ser Thr Leu Ala Lys Ile
        595                 600                 605

<210> SEQ ID NO 12
<211> LENGTH: 650
<212> TYPE: PRT
<213> ORGANISM: Artificial Sequence
<220> FEATURE:
<223> OTHER INFORMATION: Synthetic Peptide

<400> SEQUENCE: 12

Met Asp Trp Ile Trp Arg Ile Leu Phe Leu Val Gly Ala Ala Thr Gly
1               5                   10                  15

Ala His Ser Gln Val Gln Leu Val Glu Ser Gly Gly Gly Val Val Arg
            20                  25                  30

Pro Gly Arg Ser Leu Arg Leu Ser Cys Ala Ala Ser Gly Phe Ala Phe
        35                  40                  45

Ser Asp Tyr Ser Ile Asn Trp Val Arg Gln Ala Pro Gly Lys Gly Leu
    50                  55                  60

Glu Trp Val Ala Ile Ile Ser Tyr Asp Gly Arg Ile Thr Tyr Tyr Arg
65                  70                  75                  80

Asp Ser Val Lys Gly Arg Phe Thr Ile Ser Arg Asp Asp Ser Lys Asn
                85                  90                  95

Thr Leu Tyr Leu Gln Met Asn Ser Leu Arg Thr Glu Asp Thr Ala Val
            100                 105                 110

Tyr Tyr Cys Ala Arg Gln Tyr Tyr Asp Phe Trp Ser Gly Ser Ser Val
        115                 120                 125
```

```
Gly Arg Asn Tyr Asp Gly Met Asp Val Trp Gly Leu Gly Thr Thr Val
    130                 135                 140

Thr Val Ser Ser Gly Gly Gly Ser Gly Gly Gly Ser Gly Gly
145                 150                 155                 160

Gly Gly Ser Asp Ile Val Met Thr Gln Ser Pro Leu Ser Leu Ser Val
            165                 170                 175

Thr Pro Gly Glu Pro Ala Ser Ile Ser Cys Arg Ser Ser Gln Ser Leu
        180                 185                 190

Leu His Arg Ser Gly Asn Asn Tyr Leu Asp Trp Tyr Leu Gln Lys Pro
    195                 200                 205

Gly His Ser Pro Gln Leu Leu Ile Tyr Val Gly Ser Asn Arg Ala Ser
210                 215                 220

Gly Val Pro Asp Arg Phe Ser Gly Ser Gly Ser Gly Thr Glu Tyr Thr
225                 230                 235                 240

Leu Arg Ile Ser Thr Val Glu Ala Glu Asp Val Gly Val Tyr Tyr Cys
            245                 250                 255

Met Gln Ala Leu Gln Thr Pro Arg Thr Phe Gly Gln Gly Thr Lys Leu
        260                 265                 270

Glu Ile Lys Arg Ser Gly Gly Gly Gly Ser Glu Ser Lys Tyr Gly Pro
    275                 280                 285

Pro Cys Pro Ser Cys Pro Ala Pro Pro Val Ala Gly Pro Ser Val Phe
290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser Gln Glu Asp Pro Glu Val
            325                 330                 335

Gln Phe Asn Trp Tyr Val Asp Gly Val Glu Val His Asn Ala Lys Thr
        340                 345                 350

Lys Pro Arg Glu Glu Gln Phe Gln Ser Thr Tyr Arg Val Val Ser Val
    355                 360                 365

Leu Thr Val Leu His Gln Asp Trp Leu Asn Gly Lys Glu Tyr Lys Cys
370                 375                 380

Lys Val Ser Asn Lys Gly Leu Pro Ser Ser Ile Glu Lys Thr Ile Ser
385                 390                 395                 400

Lys Ala Lys Gly Gln Pro Arg Glu Pro Gln Val Tyr Thr Leu Pro Pro
            405                 410                 415

Ser Gln Glu Glu Met Thr Lys Asn Gln Val Ser Leu Thr Cys Leu Val
        420                 425                 430

Lys Gly Phe Tyr Pro Ser Asp Ile Ala Val Glu Trp Glu Ser Asn Gly
    435                 440                 445

Gln Pro Glu Asn Asn Tyr Lys Thr Thr Pro Pro Val Leu Asp Ser Asp
450                 455                 460

Gly Ser Phe Phe Leu Tyr Ser Arg Leu Thr Val Asp Lys Ser Arg Trp
465                 470                 475                 480

Gln Glu Gly Asn Val Phe Ser Cys Ser Val Met His Glu Ala Leu His
            485                 490                 495

Asn His Tyr Thr Gln Lys Ser Leu Ser Leu Ser Pro Gly Lys Lys Asp
        500                 505                 510

Pro Lys Phe Trp Val Leu Val Val Val Gly Gly Val Leu Ala Cys Tyr
    515                 520                 525

Ser Leu Leu Val Thr Val Ala Phe Ile Ile Arg Val Lys Phe Ser Arg
530                 535                 540
```

```
Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
            565                 570                 575

Arg Gly Arg Asp Pro Glu Met Gly Gly Lys Pro Arg Arg Lys Asn Pro
        580                 585                 590

Gln Glu Gly Leu Tyr Asn Glu Leu Gln Lys Asp Lys Met Ala Glu Ala
    595                 600                 605

Tyr Ser Glu Ile Gly Met Lys Gly Glu Arg Arg Arg Gly Lys Gly His
610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
            645                 650

<210> SEQ ID NO 13
<211> LENGTH: 638
<212> TYPE: PRT
<213> ORGANISM: Artificial Sequence
<220> FEATURE:
<223> OTHER INFORMATION: Synthetic Peptide

<400> SEQUENCE: 13

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Arg Tyr Gly Met His Trp Val Arg Gln Ala Pro Gly Lys Gly Leu
    50                  55                  60

Glu Trp Val Ala Val Ile Ser Tyr Asp Gly Ser Asn Lys Trp Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met His Ser Leu Arg Ala Ala Asp Thr Gly Val
            100                 105                 110

Tyr Tyr Cys Ala Lys Asp Gln Leu Tyr Phe Gly Ser Gln Ser Pro Gly
        115                 120                 125

His Tyr Trp Val Gln Gly Thr Leu Val Thr Val Ser Ser Gly Gly Gly
    130                 135                 140

Gly Ser Gly Gly Gly Gly Ser Gly Gly Gly Gly Ser Gln Ser Gln Leu
145                 150                 155                 160

Thr Gln Pro Pro Ser Val Ser Val Ala Pro Gly Gln Thr Ala Arg Ile
                165                 170                 175

Thr Cys Gly Gly Asp Asn Ile Gly Ser Lys Ser Val Asn Trp Phe Gln
            180                 185                 190

Gln Lys Pro Gly Gln Ala Pro Val Leu Val Val Tyr Asp Asp Asn Glu
        195                 200                 205

Arg Pro Ser Gly Ile Ser Glu Arg Phe Ser Gly Ser Asn Ser Gly Asn
    210                 215                 220

Thr Ala Thr Leu Thr Ile Ser Arg Val Glu Ala Gly Asp Glu Ala Asp
225                 230                 235                 240

Tyr Tyr Cys Gln Val Trp Asp Ser Ser Asp His Val Val Phe Gly
                245                 250                 255
```

-continued

```
Gly Gly Thr Lys Leu Thr Val Leu Ser Gly Gly Gly Ser Glu Ser
            260                 265                 270

Lys Tyr Gly Pro Pro Cys Pro Ser Cys Pro Ala Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Gln Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Gly Leu Pro Ser Ser Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Arg Leu Thr Val Asp
    450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys Lys Asp Pro Lys Phe Trp Val Leu Val Val Val Gly Gly Val
            500                 505                 510

Leu Ala Cys Tyr Ser Leu Leu Val Thr Val Ala Phe Ile Ile Arg Val
        515                 520                 525

Lys Phe Ser Arg Ser Ala Asp Ala Pro Ala Tyr Gln Gln Gly Gln Asn
    530                 535                 540

Gln Leu Tyr Asn Glu Leu Asn Leu Gly Arg Arg Glu Glu Tyr Asp Val
545                 550                 555                 560

Leu Asp Lys Arg Arg Gly Arg Asp Pro Glu Met Gly Gly Lys Pro Arg
                565                 570                 575

Arg Lys Asn Pro Gln Glu Gly Leu Tyr Asn Glu Leu Gln Lys Asp Lys
            580                 585                 590

Met Ala Glu Ala Tyr Ser Glu Ile Gly Met Lys Gly Glu Arg Arg Arg
        595                 600                 605

Gly Lys Gly His Asp Gly Leu Tyr Gln Gly Leu Ser Thr Ala Thr Lys
    610                 615                 620

Asp Thr Tyr Asp Ala Leu His Met Gln Ala Leu Pro Pro Arg
625                 630                 635
```

<210> SEQ ID NO 14
<211> LENGTH: 47
<212> TYPE: DNA
<213> ORGANISM: Artificial Sequence
<220> FEATURE:
<223> OTHER INFORMATION: Synthetic Primer -continued

<400> SEQUENCE: 14
gacccaccag gaccagtacc tacacaaagt actggtcctg gtgggtc    47

<210> SEQ ID NO 15
<211> LENGTH: 84
<212> TYPE: RNA
<213> ORGANISM: Homo sapiens

<400> SEQUENCE: 15
cuccccaugg cccugucucc caacccuugu accagugcug ggcucagacc cugguacagg    60 ccuggggac agggaccugg ggac    84

<210> SEQ ID NO 16
<211> LENGTH: 78
<212> TYPE: RNA
<213> ORGANISM: Homo sapiens

<400> SEQUENCE: 16
cugaggagca gggcuuagcu gcuugugagc agggucacca ccaagucgug uucacagugg    60
cuaaguuccg cccccag    78

<210> SEQ ID NO 17
<211> LENGTH: 240
<212> TYPE: PRT
<213> ORGANISM: Artificial Sequence
<220> FEATURE:
<223> OTHER INFORMATION: Synthetic Peptide

<400> SEQUENCE: 17

Glu Pro Lys Ser Cys Asp Lys Thr His Thr Cys Pro Pro Cys Pro Gly
1               5                   10                  15

Ser Gly Phe Gln Lys Ala Ser Ser Ile Val Tyr Lys Lys Glu Gly Glu
            20                  25                  30

Gln Val Glu Phe Ser Phe Pro Leu Ala Phe Thr Val Glu Lys Leu Thr
        35                  40                  45

Gly Ser Gly Glu Leu Trp Trp Gln Ala Glu Arg Ala Ser Ser Ser Lys
    50                  55                  60

Ser Trp Ile Thr Phe Asp Leu Lys Asn Lys Glu Val Ser Val Lys Arg
65                  70                  75                  80

Val Thr Gln Asp Pro Lys Leu Gln Met Gly Lys Lys Leu Pro Leu His
                85                  90                  95

Leu Thr Leu Pro Gln Ala Leu Pro Gln Tyr Ala Gly Ser Gly Asn Leu
            100                 105                 110

Thr Leu Ala Leu Glu Ala Lys Thr Gly Lys Leu His Gln Glu Val Asn
        115                 120                 125

Leu Val Val Met Gly Gln Pro Arg Glu Pro Gln Val Tyr Thr Leu Pro
    130                 135                 140

Pro Ser Arg Asp Glu Leu Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Lys Leu Thr Val Asp Lys Ser Arg
        195                 200                 205

```
Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys Lys
225                 230                 235                 240
```

<210> SEQ ID NO 18
<211> LENGTH: 690
<212> TYPE: DNA
<213> ORGANISM: Artificial Sequence
<220> FEATURE:
<223> OTHER INFORMATION: Synthetic Primer

<400> SEQUENCE: 18

```
ggatccgaga gtaaatacgg gccgccatgt ccttcctgcc cagccccgcc cgtggctggc      60
ccctccgttt tcctattccc tcccaagccg aaggatacct tgatgatctc acgcacgcca     120
gaggttactt gcgtcgtcgt tgatgtttca caggaagatc ctgaggtcca atttaactgg     180
tatgtagatg gagtcgaggt gcataacgca aagacgaaac cgcgggaaga gcagttccaa     240
tcaacttaca gggtggtgag tgtcctgaca gtgttacacc aggactggct caacgggaag     300
gagtacaagt gcaaagtaag taacaaggga ctgcccagct ctatcgagaa aacaatttcc     360
aaggccaagg gtcagccacg agaaccacaa gtctacacac tccccccctc gcaggaagaa     420
atgaccaaga atcaggtaag cctgacatgt cttgtcaaag gcttctatcc aagcgacatc     480
gccgtggagt gggagtccaa tgggcagccg gaaacaacta taaaaccac ccctccagtg     540
ctggacagcg acggctcctt tttctcttat agcagactga ccgtggacaa atctcggtgg     600
caggaaggta atgtgttttc ttgtagcgtg atgcatgagg ctctgcacaa ccactacacg     660
cagaagagcc tctccctgtc tccgggtaaa                                     690
```

<210> SEQ ID NO 19
<211> LENGTH: 230
<212> TYPE: PRT
<213> ORGANISM: Artificial Sequence
<220> FEATURE:
<223> OTHER INFORMATION: Synthetic Peptide

<400> SEQUENCE: 19

```
Gly Ser Glu Ser Lys Tyr Gly Pro Pro Cys Pro Ser Cys Pro Ala Pro
1               5                   10                  15

Pro Val Ala Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Gln
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160
```

-continued

| | | | | | | | | | | | | |
|---|---|---|---|---|---|---|---|---|---|---|---|---|
|Ala|Val|Glu|Trp|Glu 165|Ser|Asn|Gly|Gln|Pro 170|Glu|Asn|Asn|Tyr|Lys 175|Thr|
|Thr|Pro|Pro|Val 180|Leu|Asp|Ser|Asp|Gly 185|Ser|Phe|Phe|Leu|Tyr 190|Ser|Arg|
|Leu|Thr|Val 195|Asp|Lys|Ser|Arg|Trp 200|Gln|Glu|Gly|Asn|Val 205|Phe|Ser|Cys|
|Ser|Val|Met 210|His|Glu|Ala|Leu 215|His|Asn|His|Tyr|Thr 220|Gln|Lys|Ser|Leu|
|Ser|Leu|Ser|Pro|Gly 225|Lys 230|